US005989832A

United States Patent [19]
Trias et al.

[11] Patent Number: 5,989,832
[45] Date of Patent: Nov. 23, 1999

[54] METHOD FOR SCREENING FOR NON-TETRACYCLINE EFFLUX PUMP INHIBITORS

[75] Inventors: Joaquim Trias, San Mateo; Suzanne Chamberland; Scott J. Hecker, both of Los Gatos; Ving J. Lee, Los Altos, all of Calif.

[73] Assignee: Microcide Pharmaceuticals, Inc., Mountain View, Calif.

[21] Appl. No.: 08/427,088

[22] Filed: Apr. 21, 1995

[51] Int. Cl.[6] .......................... G01N 33/50; G01N 33/566
[52] U.S. Cl. .......................... 435/7.2; 435/7.32; 435/29; 435/69.1; 514/2; 514/154; 514/42; 514/23; 514/183
[58] Field of Search .................... 435/7.2, 69.1; 514/154, 2, 42, 23, 183

[56] References Cited

FOREIGN PATENT DOCUMENTS

| 547403 A1 | 11/1992 | European Pat. Off. . |
|---|---|---|
| 84/018995 | 5/1984 | WIPO . |
| 9405810 | 3/1994 | WIPO . |
| 9410303 | 5/1994 | WIPO . |

OTHER PUBLICATIONS

Bertrand et al., "Construction of a Single–Copy Promoter Vector and Its Use in Analysis of Regulation of the Transposon Tn10 Tetracycline Resistance Determinant," *J. of Bacteriology* 158:910–919 (1984).
Cohen et al., "Endogeneous Active Efflux of Norfloxacin in Susceptible *Escherichia coli*," *Antimicrobial Agents and Chemotherapy* 32:1187–1191 (1988).
Fingel et al., in The Pharmacological Basis of Therapeutics, 1975, Ch. 1, p. 1.
Levy, "Active Efflux Mechanisms for Antimicrobial Resistance," *Antimicrobial Agents and Chemotherapy* 36:695–703 (1992).
Lewis, "Multidrug resistance pumps in bacteria: variations on a theme," *TIBS* 119–123 (Mar. 1994).
Li et al., "Role of Efflux Pump(s) in Intrinsic Resistance of *Pseudomonas aerugionsa:* Resistance to Tetracycline, Chloramphenicol, and Norfloxacin," *Antimicrobial Agents and Chemotherapy* 38:1732–1741 (1994).
Li et al., "Role of Efflux Pump(s) in Intrinsic Resistance of *Pseudomonas aerugionsa:* Active Efflux as a Contributing Factor to β–Lactam Resistance," *Antimicrobial Agents and Chemotherapy* 38:1742–1752 (1994).
Livermore and Davy, "Invalidity for *Pseudomonas aeruginosa* of an Accepted Model of Bacterial Permeability to β–Lactam Antibiotics," *Antimicrobial Agents and Chemotherapy* 35:916–921 (1991).
Neyfakh et al., "Fluoroquinolone Resistance Protein NorA of *Staphylococcus auerus* is a Multidrug Efflux Transporter," *Antimicrobial Agents and Chemotherapy* 38:1732–1741 (1994).
Nikaido, "Prevention of Drug Access to Bacterial Targets: Permeability Barriers and Active Efflux," *Science* 264:382–388 (1994).

Peitz et al., *Biochem. J.* 6:2561 (1967).
Poole et al., "Cloning and sequence analysis of an EnvCD homologue in *Pseudomonas aerugionsa:* regulation by iron and possible involvement in the secretion of the siderophore pyoverdine," *Molecular Microbiology* 10:529–544 (1993).
Poole et al., "Multiple Antibiotic Resistance in *Pseudomonas aerugionsa:* Evidence for Invovlement of an Efflux Operon," *J. of Bacteriology* 175:7363–7372 (1993).
Rothstein et al., "Detection of Tetracyclines and Efflux Pump Inhibitors," *Antimicrobial Agents and Chemotherapy* 37:1624–1629 (1993).
Speer et al., "Bacterial Resistance to Tetracycline: Mechanisms, Transfer, and Clinical Significance," *Clin. Microbiol. Reviews* 5:387–399 (1992).
Vogelman et al., "In Vivo Postantibiotic Effect in a Thigh Infection in Neutropenic Mice," *J. Infect. Dis.* 157:287–298 (1988).
Wolz, "Iron Release from Transferrin by Pyoverdin and Elastase from *Pseudomonas aerugionsa,*" *Infect. & Imm.* 62:4021–4027 (1994).
Woods and Iglewski, "Modulatory Effect of Iron on the Pathogenesis of *Pseudomonas aeruginosa* Mouse Corneal Infections," *Infect. & Immun.* 35:461–464 (1982).
Wooldridge and Williams, "Iron uptake mechanisms of pathogenic bacteria," *FEMS Microbiol. Rev.* 12:325–348 (1993).
Bergeron, "A Review of Models for the Therapy of Experimental Infections," *Scand. J. Infect Dis. Suppl.* 14:189–206 (1978).
Davis, "Activity of Gentamicin, Tobramycin, Polymyxin B, and Colistimethate in Mouse Protection Tests with *Pseudomonas aeruginosa,*" *Antimicrobial Agents and Chemotherapy* 8:50–53 (1975).
Day et al., "A simple method for the study in vivo of bacterial growth and accompanying host response," *J. Infect.* 2:39–51 (1980).
Dinh et al., "A Family of Extracytoplasmic Proteins That Allow Transport of Large Molecules across the Outer Membranes of Gram–Negative Bacteria," *J. Bacteriology* 176:3825–3831 (1994).
Dufresne et al., "Cloning and Expression of the Imipenem–Hydrolyzing β–Lactamase Operon from *Pseudomonas maltophilia* in *Escherichia coli,*" *Antimicrobial Agents and Chemotherapy* 32:819–826 (1988).
Benet et al., "Ch. 1—Pharmacokinetics: The Dynamics of Drug Absorption, Distribution, and Elimination," in *The Pharmacological Basis of Therapeutics*, pp. 3–32 (1975).

(List continued on next page.)

*Primary Examiner*—Lila Feisee
*Assistant Examiner*—Michael Pak
*Attorney, Agent, or Firm*—Lyon & Lyon LLP

[57] ABSTRACT

Methods are provided for screening for inhibitors of microbial efflux pumps including those which export antibiotics. The screening methods are based on the increase in the intracellular concentration of a compound, such as an antibiotic, when the bacterial cells are contacted with an efflux pump inhibitor. In addition, this invention provides pharmaceutical compositions containing such efflux pump inhibitors, and methods for treating microbial infections using those compositions.

110 Claims, 22 Drawing Sheets

OTHER PUBLICATIONS

Gensberg and Smith, "Siderophore–specific of iron uptake in *Pseudomonas aeruginosa*," *J. Gen. Microbiol.* 138:2381–2387 (1992).

Haas, "Siderophore Presence in Sputa of Cystic Fibrosis Patients," *Infect. & Imm.* 59:3997–4000 (1991).

Kelly et al., "Surface Characteristics of *Pseudomonas aeruginosa* Grown in a Chamber Implant Model in Mice and Rats," *Infect. Immun.* 57:344–350 (1989).

Kirsch et al., "The Use of β–Galactosidase Gene Fusions to Screen for Antibacterial Antibiotics," *J. Antibiotics* 44:210–217 (1991).

Malouin et al., "Outer Membrane and Porin Characteristics of *Serratia marcescens* Grown In Vitro and in Rat Intraperitoneal Diffusion Chambers," *Infect. Immun.* 58:1247–1253 (1990).

Murray, "Can Antibiotic Resistance be Controlled?" *New Engl. J. Med.* 330:1229–1230 (1994).

Reitz et al., "The Biochemical Mechanisms of Resistance by Streptococci to the Antibiotics D–Cycloserine and O–Carbamhyl–D–Serine," *Biochem. J.* 6:2561–2570 (1967).

Santoro and Levinson, "Rat Model of Experimental Endocarditis," *Infect. Immun.* 19:915–918 (1978).

Sato et al., "Antimicrobial Activity of DU–6859, a New Potent Fluoroquinolone, against Clinical Isolates," *Antimicrobial Agents and Chemotherapy* 37:1491–1498 (1992).

Seoane and Levy, "Reversal of MarR binding to the regulatory region of the marRAB operon by structurally unrelated inducers," *Abstr. of the Am. Soc. for Microbiol. Gen. Meeting*, Las Vegas, NV Abstract H–26 (1994).

Sokol, "Surface Expression of Ferripyochelin–Binding Protein is Required for Virulence of *Pseudomonas aerugionsa*," *Infect. & Imm.* 55:2021–2025 (1987).

Spratt, "Resistance to Antibiotics Mediated by Target Alterations," *Science* 264:388–393 (1994).

Sriyoshachati and Cox, "Siderophore–Mediated Iron Acquisition from Transferrin by *Pseudomonas aerugionsa*," *Infect. & Imm.* 52:885–891 (1986).

Tanaka, et al., "Antimicrobial Activity of DV–7751a, a New Fluoroquinolone," *Antimicrobial Agents and Chemotherapy* 37:2112–2218 (1993).

Trias, "Decreased Outer Membrane Permeability in Imipenem–Resistant Mutants of *Pseudomonas aeruginosa*," *Antimicrobial Agents and Chemotherapy* 33:1201–1206 (1989).

Gold man, et al. Antimicro. Agents Chemo. vol. 34(10): pp. 1973–1980. Oct. 1990.

Ahmed et al., "A Protein That Activates Expression of a Multidrug Efflux Transporter upon Binding the Transporter Substrates," *J. Biol. Chem.* 269:28506–28513 (1994).

| PROPERTY | ABC | MAJOR FACILITATOR MF1 12 TRANSMEMBRANE HELICES | MAJOR FACILITATOR MF1 14 TRANSMEMBRANE HELICES | RND (RESISTANCE-NODULATION) |
|---|---|---|---|---|
| ENERGY SOURCE | ATP | PROTON MOTIVE FORCE | PROTON MOTIVE FORCE | PROTON MOTIVE FORCE |
| CYTOPLASMIC MEMBRANE | 2 TRANSMEMBRANE DOMAINS WITH 6 HELICES EACH; 2 ATP BINDING DOMAINS | 2 TRANSMEMBRANE DOMAINS WITH 6 HELICES EACH | 2 TRANSMEMBRANE DOMAINS WITH 7 HELICES EACH | 2 TRANSMEMBRANE DOMAINS WITH 6 HELICES EACH |
| MEMBRANE FUSION PROTEIN | --- | USUALLY ABSENT, PRESENT IN Emr PUMP | --- | PRESENT IN ALL DESCRIBED PUMPS |
| OUTER MEMBRANE PROTEIN | --- | --- | --- | USUALLY ABSENT, PRESENT IN *P. aeruginosa* PUMPS |
| EFFLUX PUMPS INVOLVED IN DRUG EXPORT | P1-GLYCOPROTEIN (MAMMALIAN), MsrA | TetA-E, NorA, Bmr, CmlA, Bcr, EmrAB | TetK, TetL, QacA, QacB | AcrAB, AcrEF, (EnvCD), MexAB-OprK, MexCD-OprM |
| HOMOLOGOUS PROTEINS | MalK, HlyB, STE6, CFTR | Xyl, Ara, RELATED TO MF2 | Mmr, RELATED TO MF1 | Nod, Cya, Cnr, Czc |
|  | NO HOMOLGY WITH OTHER EFFLUX PUMP FAMILIES | NO HOMOLOGY WITH OTHER EFFLUX PUMP FAMILIES | NO HOMOLOGY WITH OTHER EFFLUX PUMP FAMILIES | NO HOMOLOGY WITH OTHER EFFLUX PUMP FAMILIES |

FIG. 1.

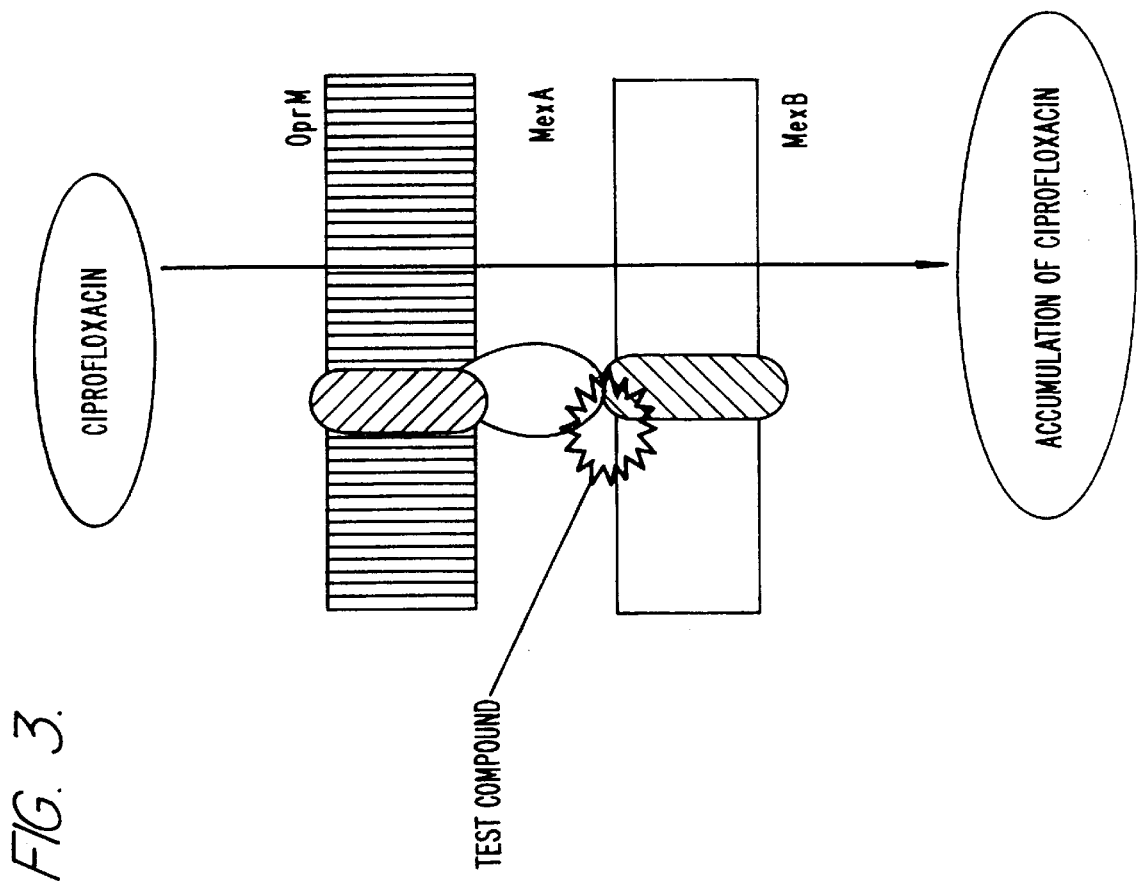
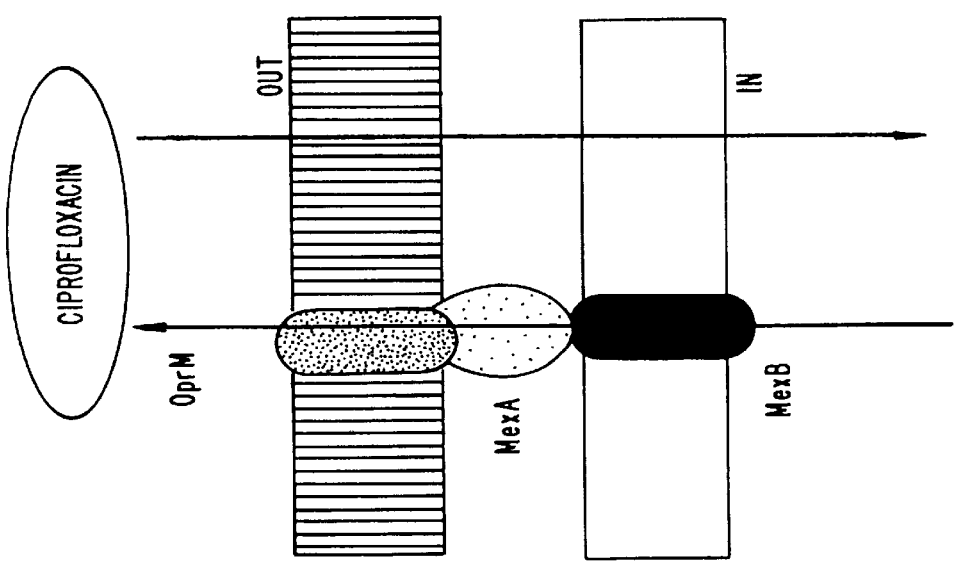
FIG. 3.

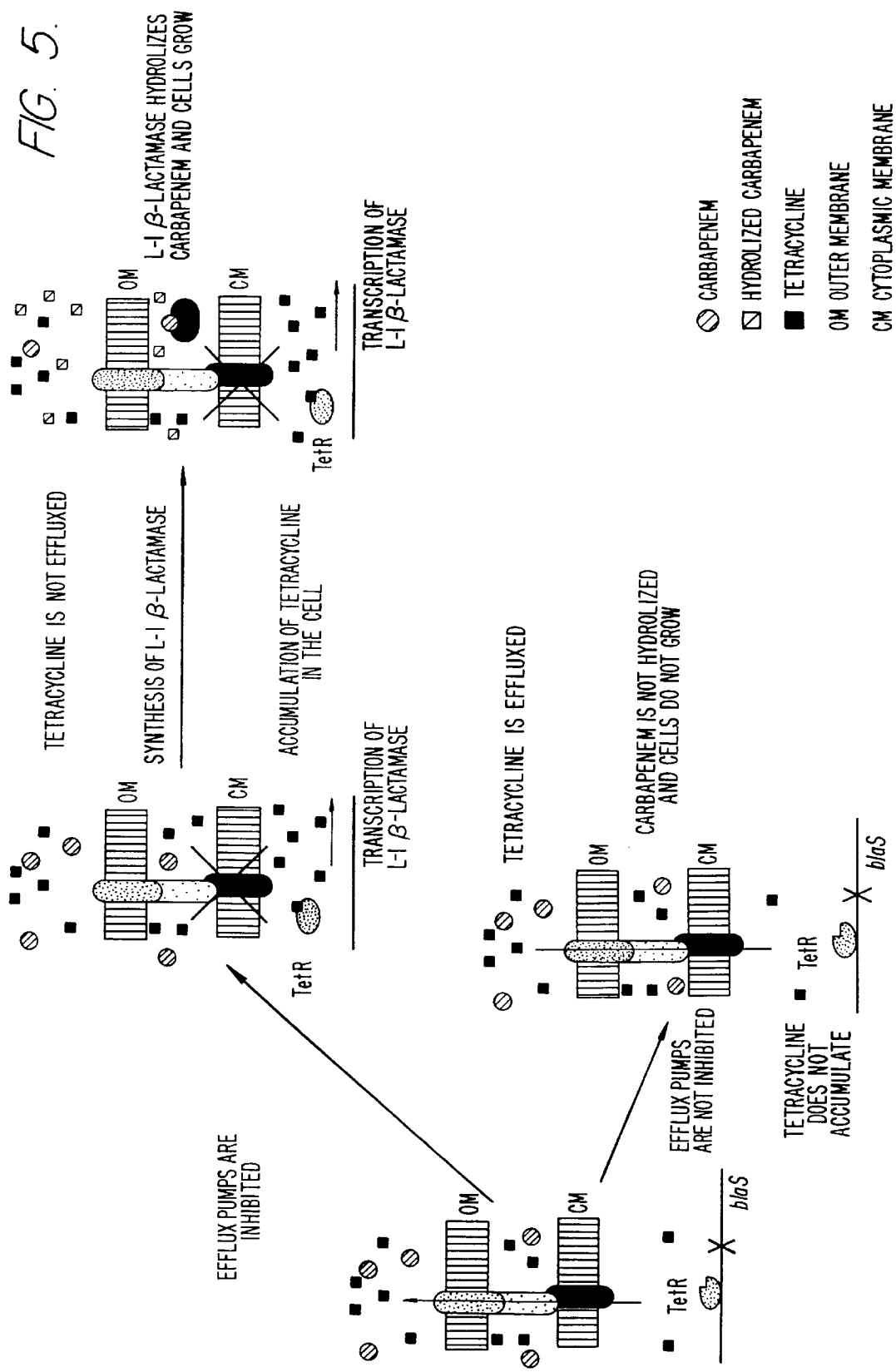

| P. Aruginosa STRAINS USED IN THIS STUDY | | | | |
|---|---|---|---|---|
| | PAO1 | K385 | PAO4O98E | K799/6 |
| EFFLUX PUMP | BASAL LEVEL | CONSTITUTIVE OVERPRODUCER | CONSTITUTIVE OVERPRODUCER | - |

1. PAO1 PRODUCES A BASAL LEVEL OF EFFLUX PUMP(S)

2. K385 OVERPRODUCES AN EFFLUX PUMP. ISOLATED FROM K372 A PYOVERDIN/PYOCHELIN DEFICIENT DERIVATIVE OF PAO1

3. PAO4O98E WAS ISOLATED FROM PAO1 AND OVERPRODUCES A PUMP DIFFEFRENT FROM THE ONE PRODUCED BY K385

4. K613 IS K372 WITH A TRANSPOSITION IN OprK - IDENTITY WAS CONFIRMED BY PLATING ON Hg-TSA.

5. 799/61 IS A PUMP DEFICIENT MUTANT, NO KNOWN PUMPS CAN BE FOUND IN THIS STRAIN

6. - INDICATE THAT THE PUMP HAS NOT BEEN DETECTED BY SDS-PAGE.

FIG. 7.

| MIC(μg/ml) of PAN | STRAIN | TETRACYCLINE[a] MIC (μg/ml) WITH PAN AT: | | | |
|---|---|---|---|---|---|
| | | 0 | 5 | 10 | 40μg/ml |
| 64 | PA01 | 8 | 1 | 0.5 | 0.25 |
| 256 | K385 | 16 | 4 | 2 | 1 |
| 256 | 4098E | 32 | 8 | 4 | 4 |
| 32 | K799/61 | 0.03 | 0.03 | 0.03 | -- |

| MIC(μg/ml) of PAN | STRAIN | CYPROFLOXCIN[b] MIC (μg/ml) WITH PAN AT: | | | |
|---|---|---|---|---|---|
| 64 | PA01 | 0.5 | 0.5 | 0.125 | 0.03 |
| 256 | K385 | 1 | 0.125 | 0.06 | 0.03 |
| 256 | 4098E | 0.5 | 0.25 | 0.06 | 0.03 |
| 32 | K799/61 | 0.008 | 0.008 | 0.008 | -- | a- NCCLS SUSCEPTABILITY BREAKPOINT FOR TETRACYCLINE IS ≤4 μg/ml.
b- NCCLS SUSCEPTABILITY BREAKPOINT FOR CYPROFLOXIN IS ≤1 μg/ml.
c- A $FIC_{index}$ ≤0.5 SHOWS THAT THE DRUG COMBINATION IS SYNERGISTIC.
d- --INDICATES THAT THE DETERMINATION COULD NOT BE DONE SINCE PAN POSSESSES INTRINSIC ACTIVITY FOR THE STRAINS AT 40 μg/ml.

| | PAO1 MIC (μg/ml) | | K385 MIC (μg/ml) | |
|---|---|---|---|---|
| | CONTROL | L-phenylalalnyl-L-arginyl-β-naphthylamide [a] | CONTROL | L-phenylalalnyl-L-arginyl-β-naphthylamide [a] |
| CHLORAMPHENICAL | 256 | 8 | 128 | 1 |
| TETRACYCLINE | 16 | 0.5 | 32 | 4 |
| OFLOXACIN | 8 | 0.06 | 8 | 0.06 |
| PEFLOXACIN | 8 | 0.03 | 8 | 0.015 |
| LOMEFLOXACIN | 4 | 0.125 | 8 | 0.125 |
| NORFLOXACIN | 2 | 0.5 | 4 | 1 |
| SPARFLOXACIN | 2 | 0.004 | 8 | 0.015 |
| TOSUFLOXACIN | 1 | 0.004 | 2 | 0.004 |
| CIPROFLOXACIN | 0.5 | 0.06 | 2 | 0.06 |
| IMIPENEM | 2 | 1 | 1 | 1 |
| PIPERACILLIN | 2 | 0.25 | 4 | 0.5 |
| CEFTAZIDIME | 1 | 0.06 | 1 | 0.06 |
| GENTAMICIN | 0.25 | 0.5 | 0.5 | 0.5 |

[a] MIC DETERMINED IN THE PRESENCE OF 20 mg/ml OF L-phenylalanyl-L-arginyl-b-naphthylamide.

FIG. 11.

| | Hydrophobicity[a] | Ionic Type | Fold-increase in susceptibility L-phenylalanyl-L-arginyl-β-naphthylamide at 20 μg/ml | |
|---|---|---|---|---|
| | | | PAO1 | K385 |
| Norfloxacin | 0.01 | Amphoteric | 4 | 4 |
| Ciprofloxacin | 0.02 | Amphoteric | 8 | 32 |
| Ofloxacin | 0.33 | Amphoteric | 128 | 128 |
| Pefloxacin | 1.32 | Amphoteric | 256 | 512 | a Partition coefficient in n-octanol-0.1M phosphate buffer, pH 7.2

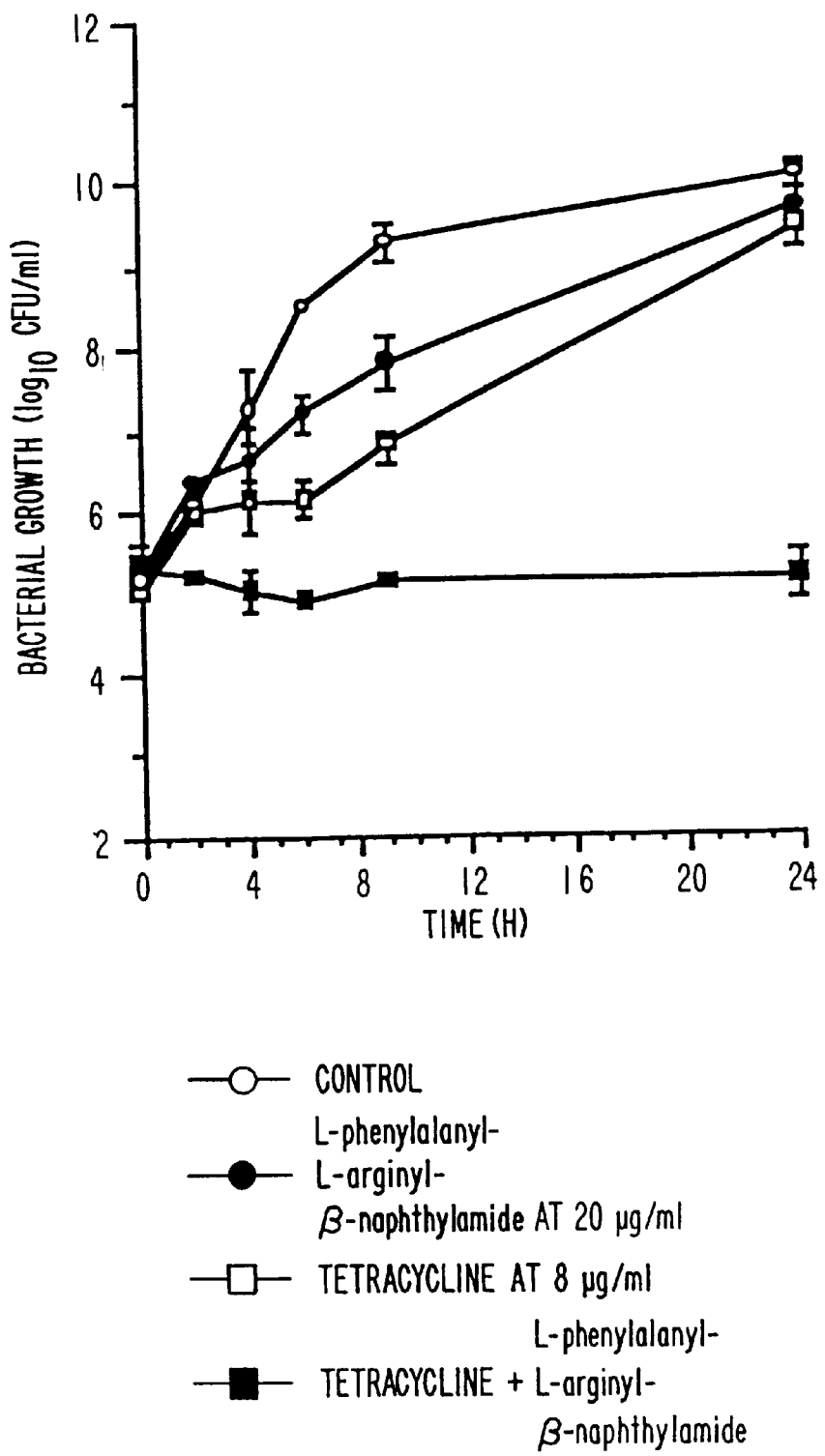

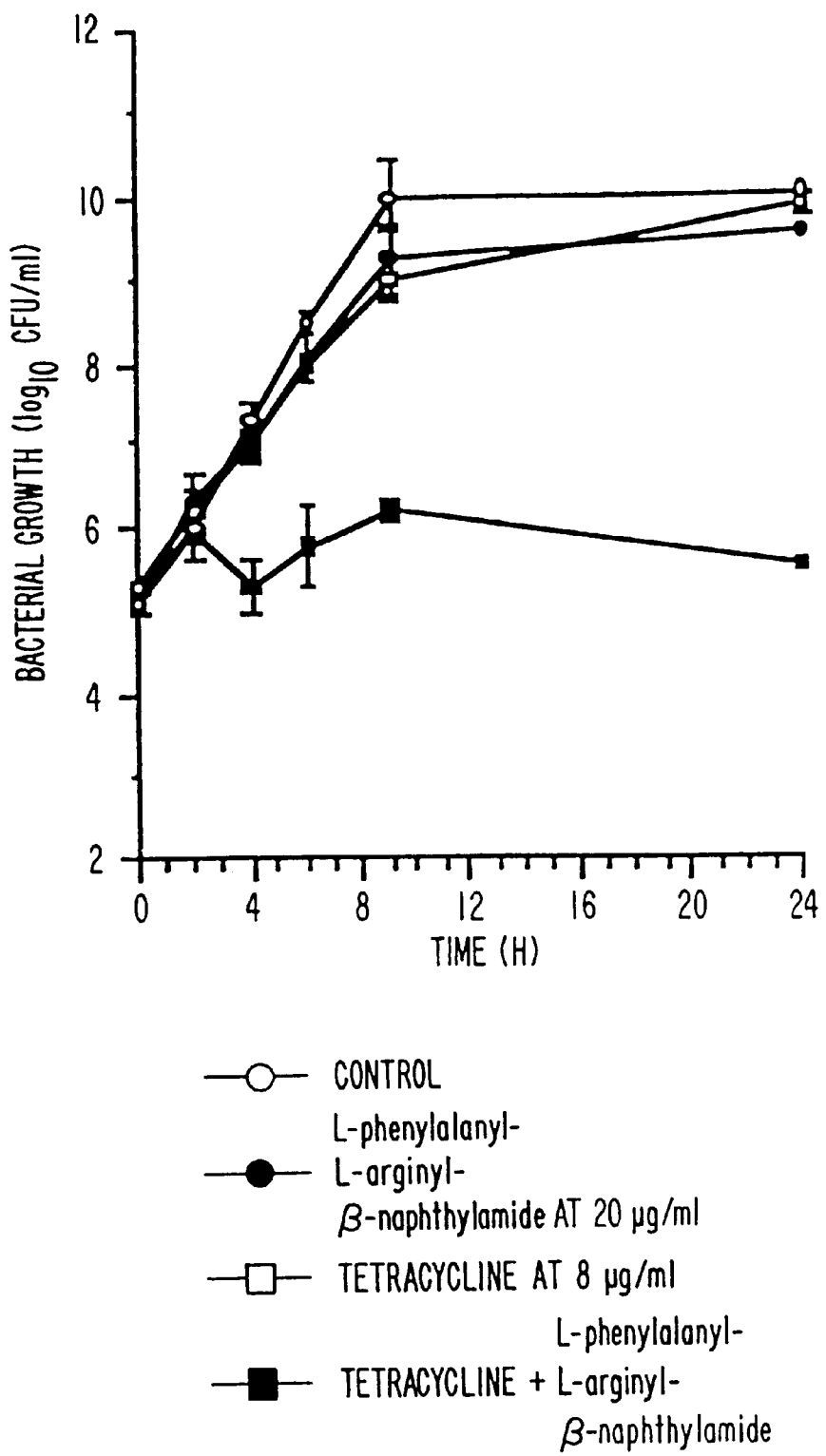

| PAN | NOT AFFECTED BY PAN $(x/n)^a$ |
|---|---|
| PSEUDOMONAS AERUGINOSA (35/36) | BURKHOLDERIA CEPACIA$^b$(3/3) |
| PSEUDOMONAS FLUORESCENS (1/1) | STENOTROPHOMONAS MALTOPHILIA (10/10) |
| ESCHERICHIA COLI (2/9) | CITROBACTER FREUNDII (2/2) |
| SALMONELLA TYPHIMURIUM (2/2) | AEROMONAS HYDROPHILIA (1/1) |
| ENTEROBACTER CLOACAE (2/2) | ENTEROCOCCUS FAECIUM (7/7) |
| KLEBSIELLA PNEUMONIAE (2/3) | ENTEROCOCCUS FAECALIS (9/9) |
| KLEBSIELLA OXYTOCA (2/4) | STAPHYLOCOCCUS HAEMOLYTICUS $(1/1)^c$ |
| SERRATIA MARCESCENS (1/1) | |
| STAPHYLOCOCCUS AUREUS (1/7) | | a  x/n INDICATES THE NUMBER OF STRAINS POTENTIATED OVER THE NUMBER OF STRAINS TESTED OF A GIVEN SPECIES.

b  CIPROFLOXACIN MICs WERE NOT CHANGE FOR 3 STRAINS OF BURKHOLDERIA CEPACIA, HOWEVER, ONE OF THOSE STRAINS WAS SUSCEPTIBLE TO PAN ALONE WITH AN MIC OF 10 μg/ml.

c  THIS STRAIN WAS SUSCEPTIBLE TO 40 μg/ml OF PAN AND A SLIGHT DECREASE IN MIC WAS NOTED AT 20, AND 10 μg/ml OF PAN SHOWING AN ADDITIVE EFFECT BETWEEN CIPROFLOXACIN AND PAN.

FIG. 16.

—□— 0
·····◇····· 250 μM CCCP
······○······ 0.1 mM L-phenylalanyl-L-arginyl-β-naphthylamide
-----△----- 1.0 mM L-phenylalanyl-L-arginyl-β-naphthylamide L-phenylalanyl-L-arginyl- β–naphthylamide

METHOD FOR SCREENING FOR NON-TETRACYCLINE EFFLUX PUMP INHIBITORS

FIELD OF THE INVENTION

This invention relates to the field of antimicrobial agents and to methods for identification and characterization of potential antimicrobial agents. More particularly, this invention relates to antimicrobial agents for which the mode of action involves cellular efflux pumps and the regulation of efflux pumps.

BACKGROUND

The following background material is not admitted to be prior art to the pending claims, but is provided only to aid the understanding of the reader.

Antibiotics have been effective tools in the treatment of infectious diseases during the last half century. From the development of antibiotic therapy to the late 1980s there was almost complete control over bacterial infections in developed countries. The emergence of resistant bacteria, especially during the late 1980s and early 1990s, is changing this situation. The increase in antibiotic resistant strains has been particularly common in major hospitals and care centers. The consequences of the increase in resistant strains include higher morbidity and mortality, longer patient hospitalization, and an increase in treatment costs. (B. Murray, 1994, *New Engl. J. Med.* 330: 1229–1230.)

The constant use of antibiotics in the hospital environment has selected bacterial populations that are resistant to many antibiotics. These populations include opportunistic pathogens that may not be strongly virulent but that are intrinsically resistant to a number of antibiotics. Such bacteria often infect debilitated or immunocompromised patients. The emerging resistant populations also include strains of bacterial species that are well known pathogens, which previously were susceptible to antibiotics. The newly acquired resistance is generally due to DNA mutations, or to resistance plasmids (R plasmids) or resistance-conferring transposons transferred from another organism. Infections by either type of bacterial population, naturally resistant opportunistic pathogens or antibiotic-resistant pathogenic bacteria, are difficult to treat with current antibiotics. New antibiotic molecules which can override the mechanisms of resistance are needed.

Bacteria have developed several different mechanisms to overcome the action of antibiotics. These mechanisms of resistance can be specific for a molecule or a family of antibiotics, or can be non-specific and be involved in resistance to unrelated antibiotics. Several mechanisms of resistance can exist in a single bacterial strain, and those mechanisms may act independently or they may act synergistically to overcome the action of an antibiotic or a combination of antibiotics. Specific mechanisms include degradation of the drug, inactivation of the drug by enzymatic modification, and alteration of the drug target (B. G. Spratt, *Science* 264:388 (1994)). There are, however, more general mechanisms of drug resistance, in which access of the antibiotic to the target is prevented or reduced by decreasing the transport of the antibiotic into the cell or by increasing the efflux of the drug from the cell to the outside medium. Both mechanisms can lower the concentration of drug at the target site and allow bacterial survival in the presence of one or more antibiotics which would otherwise inhibit or kill the bacterial cells. Some bacteria utilize both mechanisms, combining a low permeability of the cell wall (including membranes) with an active efflux of antibiotics. (H. Nikaido, *Science* 264:382–388 (1994)).

In some cases, antibiotic resistance due to low permeability is related to the structure of the bacterial membranes. In general, bacteria can be divided into two major groups based on the structure of the membranes surrounding the cytoplasm. Gram-positive (G+) bacteria have one membrane, a cytoplasmic membrane. In contrast, Gram-negative (G−) bacteria have two membranes, a cytoplasmic membrane and an outer membrane. These bacterial membranes are lipid bilayers which contain proteins and may be associated with other molecules. The permeability of bacterial membranes affects susceptibility/resistance to antibiotics because, while there are a few molecular targets of antibiotics, e.g., penicillin-binding proteins, that are accessible from the outer leaflet of the cytoplasmic membranes, the principal targets for antibiotics are in the cytoplasm or in the inner leaflet of the cytoplasmic membrane. Therefore for an antibiotic which has a target in the cytoplasmic membrane, in Gram-negative bacteria that antibiotic will first need to cross the outer membrane. For a target in the cytoplasm, an antibiotic will need to cross the cytoplasmic membrane in Gram-positive bacteria, and both the outer and cytoplasmic membranes in Gram-negative bacteria. For both membranes, an antibiotic may diffuse through the membrane, or may cross using a membrane transport system.

For Gram-negative bacteria, the lipid composition of the outer membrane constitutes a significant permeability barrier. The outer layer of this outer membrane contains a lipid, lipopolysaccharide (LPS), which is only found in the outer membrane of Gram-negative bacteria. The lipid layer of the outer membrane is highly organized in a quasi-crystalline fashion and has a very low fluidity. Because of the low fluidity of the lipid layer of the outer membrane, even lipophilic antibiotics will not diffuse rapidly through the lipid layer. This has been shown experimentally, hydrophobic probe molecules have been shown to partition poorly into the hydrophobic portion of LPS and to permeate across the outer membrane bilayer at about one-fiftieth to one-hundredth the rate through the usual phospholipid bilayers (like the cytoplasmic membrane bilayer).

Some antibiotics may permeate through water-filled porin channels or through specific transport systems. Many of the porin channels, however, provide only narrow diameter channels which do not allow efficient diffusion of the larger antibiotic molecules. In addition, many porin channels are highly hydrophilic environments, and so do not efficiently allow the passage of hydrophobic molecules. Thus, the outer membrane acts as a molecular sieve for small molecules. This explains, in part, why Gram-negative bacteria are generally less susceptible to antibiotics than Gram-positive bacteria, and why Gram-negative bacteria are generally more resistant to large antibiotics, such as glycopeptides, that cannot cross the outer membrane.

The cytoplasmic membrane also provides a diffusion barrier for some antibiotics. However, since the fluidity of the lipid layer of the cytoplasmic membrane is higher than that of the outer membrane of Gram-negative bacteria, drugs that show some lipophilicity will be able to permeate through the lipid layer. Other drugs, such as phosphonomycin or D-cycloserine that have very low solubility in a lipophilic environment will cross the cytoplasmic membrane by using a transport system. In this case, though, if the transport system is not synthesized, the bacteria will become resistant to the drug (Peitz et al., 1967, *Biochem. J.* 6: 2561).

Decreasing the permeability of the outer membrane, by reducing either the number of porins or by reducing the number of a certain porin species, can decrease the susceptibility of a strain to a wide range of antibiotics due to the decreased rate of entry of the antibiotics into the cells. However, for most antibiotics, the half-equilibration times are sufficiently short that the antibiotic could exert its effect unless another mechanism is present. Efflux pumps are an example of such other mechanism. Once in the cytoplasm or periplasm a drug can be transported back to the outer medium. This transport is mediated by efflux pumps, which are constituted of proteins. Different pumps can efflux specifically a drug or group of drugs, such as the NorA system that transports quinolones, or Tet A that transports tetracyclines, or they can efflux a large variety of molecules, such as certain efflux pumps of *Pseudomonas aeruginosa*. In general, efflux pumps have a cytoplasmic component and energy is required to transport molecules out of the cell. Some efflux pumps have a second cytoplasmic membrane protein that extends into the periplasm. At least some efflux pumps of *P. aeruginosa* have a third protein located in the outer membrane.

Efflux pumps are involved in antibiotic resistance since, in some cases, they can remove a significant fraction of the antibiotic molecules which manage to enter the cells, thereby maintaining a very low intracellular antibiotic concentration. To illustrate, *P. aeruginosa* laboratory-derived mutant strain 799/61, which does not produce any measurable amounts of efflux pump is 8 to 10 fold more susceptible to tetracycline and ciprofloxacin than the parent strain *P. aeruginosa* 799, which synthesizes efflux pumps. Also, null mutants of mexA, the cytoplasmic component of a *P. aeruginosa* efflux pump, are more susceptible to antibiotics than the wild type.

The physiological role of efflux pumps has not been clearly defined yet. They are involved in drug resistance but they also are involved in the normal physiology of the bacterial cell. The efflux pump coded in the mexA operon of *P. aeruginosa* has been shown to be regulated by the iron content of the medium, and it is co-regulated with the synthesis of the receptors of siderophores. Siderophores are molecules that are needed for bacterial growth under iron starvation conditions, such as during infection of an animal. They are synthesized in the cytoplasm and exported when the bacterial cell needs iron. Siderophores scavenge iron within the infected animal and return the iron to the microbe to be used for essential microbial processes. Since there is essentially no free iron in the bodies of animals, including the human body, the production of siderophores by infecting bacteria is an important virulence factor for the progress of the infection.

Even organisms normally surrounded by a cell envelope of relatively high permeability can develop resistance by decreasing the permeability of the envelope. When an agent mainly diffuses across the barrier through a specific channel, mutational loss of the channel can be an efficient mechanism for resistance. A "nonclassical" β-lactam compound, imipenem, shows an exceptional activity against *P. aeruginosa*, mainly because this agent diffuses though a specific channel, OprD, whose physiological function appears to be that of the transport of basic amino acids. However, *P. aeruginosa* could become resistant to imipenem by simply losing the oprD channel, and currently a large fraction of *P. aeruginosa* strains isolated from the hospital environment are resistant as a result of this modification. In a similar manner, β-lactam compounds designed to mimic iron-chelating compounds (siderophores) during their transport through the outer membranes are known to select mutants that are defective in the specific transport of these siderophores.

In summary, the above discussion indicates that cellular factors affecting transport (both active and passive transport) of antibiotics into bacterial cells are important components of antibiotic resistance for many bacterial species.

SUMMARY

This invention provides methods for screening compounds to identify efflux pump inhibitors, which are compounds which inhibit cellular efflux pumps of bacteria or other microbes. Such efflux pumps export substrate molecules from the cytoplasm in an energy-dependent manner, and the exported substrate molecules can include antibacterial agents. Such efflux pump inhibitors are useful, for example, for treating microbial infections by reducing the export of a co-administered antimicrobial agent or by preventing the export of a compound synthesized by microbes (e.g., bacteria) to allow or improve their growth. An example of reducing the export of such a compound is inhibiting iron availability for the microbe by reducing the export of siderophores. Thus, this invention also provides compositions which include such efflux pump inhibitors and methods for treating microbial infections using those compositions. Consequently, this invention discloses a therapeutic approach which is appropriate for many pathogenic organisms which are resistant to antimicrobial agents. A particularly appropriate example of such a microbe is a pathogenic bacterial species, *Pseudomonas aeruginosa*, which is intrinsically resistant to many of the commonly used antibacterial agents. Exposing this bacterium to an efflux pump inhibitor can significantly slow the export of an antibacterial agent from the interior of the cell or the export of siderophores. Therefore, if another antibacterial agent is administered in conjunction with the efflux pump inhibitor, the antibacterial agent, which would otherwise be maintained at a very low intracellular concentration by the export process, can accumulate to a concentration which will inhibit the growth of the bacterial cells. This growth inhibition can be due to either bacteriostatic or bactericidal activity, depending on the specific antibacterial agent used. While *P. aeruginosa* is an example of an appropriate bacterium, other bacterial and microbial species may contain similar broad substrate pumps, which actively export a variety of antimicrobial agents, and thus can also be appropriate targets. In addition as suggested above, for some bacterial species, efflux pump inhibitors can decrease the virulence of the bacterium, for example, by inhibiting the transport of factors important for pathogenicity. Again using *P. aeruginosa* as an example, inhibition of an efflux pump in this bacterium inhibits the uptake of iron, which is important for pathogenicity. The mechanism of bacterial iron transport involves molecules called siderophores, which are synthesized and exported by bacterial cells via efflux pumps. These siderophores bind tightly to iron scavenged from the host, and are then taken up by the bacteria. In this way, the iron needed for bacterial metabolism is obtained, and an infection can be maintained.

Therefore, illustrating the utility of efflux pump inhibitors, inhibiting the efflux pump of *P. aeruginosa* allows obtaining one or more of the following biological effects:

1. *P. aeruginosa* strains will become susceptible to antibiotics that could not be used for treatment of pseudomonad infections, or become more susceptible to antibiotics which do inhibit pseudomonal growth.

2. *P. aeruginosa* strains will become more susceptible to antibiotics currently used for treatment of pseudomonad infections.

3. Virulence of *P. aeruginosa* will be attenuated because the availability of iron will be hampered.

4. The inhibition of one of the components of the pump may be lethal.

Obtaining even one of these effects provides a potential therapeutic treatment for infections by this bacterium. Also, as previously mentioned, similar pumps are found in other microorganisms. Some or all of the above effects can also be obtained with those microbes, and they are therefore also appropriate targets for detecting or using efflux pump inhibitors.

Thus, in a first aspect this invention provides a method for screening for a non-tetracycline-specific efflux pump inhibitor. The method involves determining the growth of a bacterium which produces a non-tetracycline-specific efflux pump, when the bacterium is grown in the presence of a non-zero subinhibitory concentration of an antibacterial agent normally effluxed by a non-tetracycline-specific efflux pump in the bacterium. The efflux pump will, if not inhibited, maintain the intracellular concentration of the antibacterial agent at a low level, so that the antibacterial agent does not inhibit the cell. However, if there is also present a compound which significantly slows or stops the export of the antibacterial agent, that agent can accumulate in the cell to a higher concentration, so that the antibacterial agent can inhibit growth of the cell at the higher intracellular concentration.

In certain preferred embodiments, a component of the efflux pump has at least 50% amino acid sequence similarity with a polypeptide which is part of the *Pseudomonas aeruginosa* mexA/mexB/oprM efflux pump or the efflux pump overexpressed by *P. aeruginosa* Strain K385, or the efflux pump overexpressed by *P. aeruginosa* Strain PAO4098E. Due to the described sequence similarity of a component polypeptide of the efflux pump, such an efflux pump is termed a *Pseudomonas aeruginosa*-type efflux pump. Such a pump will efflux one or more non-tetracycline compounds (but may also efflux tetracycline), which may include, for example, other classes of antimicrobial agents and virulence factors. In particular preferred embodiments, the efflux pump is a *Pseudomonas aeruginosa* efflux pump, which is an efflux pump naturally found in *Pseudomonas aeruginosa*. Some such *Pseudomonas aeruginosa* efflux pumps were indicated above. Also in particular preferred embodiments, the bacterium is *Pseudomonas aeruginosa*, for example, Strain K385 or Strain PAO4098E.

Also in certain preferred embodiments, the bacterium is from other bacterial species, such as any of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Gardnerella vaginalis, Bacteroides fragilis, Bacteroides distasonis,* Bacteroides 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis, Staphylococcus saccharolyticus.*

The term "efflux pump," refers to a protein assembly which exports substrate molecules from the cytoplasm or periplasm of a cell, in an energy dependent fashion. Thus an efflux pump will typically be located in the cytoplasmic membrane of the cell (spanning the cytoplasmic membrane). In Gram-negative bacteria the pump may span the periplasmic space and there may also be portion of the efflux pump which spans the outer membrane. Certain efflux pumps will include a polypeptide which has at least 50% amino acid sequence similarity with a polypeptide which is part of the *Pseudomonas aeruginosa* mexA/mexB/oprM efflux pump or the efflux pump overexpressed by *P. aeruginosa* Strain K385, or the efflux pump overexpressed by *P. aeruginosa* Strain PAO4098E. Due to the described sequence similarity of a component polypeptide of the efflux pump, such an efflux pump is termed a *Pseudomonas aeruginosa*-type efflux pump.

The term "non-tetracycline-specific efflux pump" refers to an efflux pump which is not highly specific for tetracycline (relative to other antibiotics) and thus is not a tetracycline (tetracycline-specific) efflux pump. The term thus includes broad substrate pumps (efflux a number of compounds with varying structural characteristics) and pumps which are highly specific for compounds (including antibiotics) other than tetracyclines. Tetracycline efflux pumps are involved in specific resistance to tetracycline in bacteria. (Speer et al., 1992, *Clin. Microbiol. Rev.* 5: 387–399.) As noted, these pumps are highly specific for tetracyclines, and their presence confers high tetracycline resistance to the cell. However, they do not confer resistance to other antibiotics. The genes for the tetracycline pump components are found in plasmids in Gram-negative as well as in Gram-positive bacteria and can be divided in two main groups, tetA(A-E), and tetK and tetL. TetA-E tetracycline resistance determinants contain a structural gene, tetA, which is a tetracycline specific pump, and a repressor gene, tetR, that mediates inducible resistance to tetracyclines. Tetracycline efflux pumps belonging to this group are designated tetA(A), tetA(B), tetA(D), and tetA(E), and are found in Enterobacteriaceae and other Gram-negative bacteria. TetK and TetL are pumps involved in tetracycline resistance in Gram-positive bacteria. The genes are regulated via translational attenuation and are not homologous to tetA group.

Use of the term "a method for screening" indicates that the method is appropriate for evaluating the effects of a number of compounds, often simultaneously. In this invention, such screening is directed to determining the ability of a compound to inhibit an efflux pump. In this context, "screening" is distinguished from testing, in which a method is suitable for evaluating one or only a few compounds.

An "efflux pump inhibitor" is a compound which specifically interferes with the ability of an efflux pump to export its normal substrate, or other compounds such as an antibiotic. The inhibitor may have intrinsic antimicrobial (e.g., antibacterial) activity of its own, but at least a significant portion of the relevant activity is due to the efflux pump inhibiting activity. Of particular interest in this invention, are compounds which inhibit the export or activity of efflux pumps which have a broad substrate range which includes antibacterial agents. The term "non-tetracycline-specific efflux pump inhibitor" refers to an efflux pump inhibitor which inhibits a non-tetracycline-specific efflux pump. The term "*Pseudomonas aeruginosa*-type efflux pump inhibitor" refers to an efflux pump inhibitor which inhibits a *Pseudomonas aeruginosa*-type efflux pump. A "*Pseudomonas aeruginosa* efflux pump inhibitor" is an efflux pump inhibitor which inhibits the export activity of an efflux pump found in *Pseudomonas aeruginosa*.

A "potential" efflux pump inhibitor refers to a compound which is to be or is being tested for activity as an efflux pump inhibitor, and is therefore a "test compound" or a "putative efflux pump inhibitor."

As used herein in reference to the growth of a bacterium or other microbe, the term "growth" or "grow" denotes primarily the reproduction of the microbe, i.e., an increase in numbers, rather than an increase in size. Thus, this term is applicable to both a single cell and to a population of cells of one or more types. However, these terms also imply that the cell(s) undergoing growth are maintaining on-going metabolic processes, and not merely undergoing a round of reproduction, such as cell division. These terms also, however, apply to the increase in size of a multinucleate form of an organism, such as some fungi, with the accompanying increase in the number of nuclei present.

In the context of bacterial (similarly for other microbes) cell growth, the term "inhibit" means that the rate of growth of the bacterial population is decreased. Such inhibition can be monitored, for example, by the difference in turbidity of liquid cultures in the presence or absence of the inhibiting agent, or by the difference in plaque size for cultures on solid media in the presence or absence of the inhibiting agent.

In reference to the presence of a specific efflux pump in a bacterium, the term "overproduces" refers to the presence in that bacterium of a significantly larger number of the specific efflux pump than is found in most naturally occurring (usually non-hospital varieties) isolates of that bacterial species. The term does not refer merely to the production of a large number of the component polypeptides of an efflux pump, but rather to the presence of a larger number of functional efflux pumps in the membranes of the cell. Consequently, a cell which overproduces an efflux pump, will export the substrate molecules more efficiently than a strain of that bacterium which does not overproduce the efflux pump.

A bacterial strain which overproduces an efflux pump, is thus in contrast to a "wild-type strain". A wild-type strain produces a specific efflux pump at a level which is typical of natural isolates of that bacterial species. More importantly, however, a wild-type strain produces a specific efflux pump at a level which is significantly lower than a related strain which overproduces that specific efflux pump.

As used herein, the term "antibacterial agent" refers to a compound which specifically inhibits the growth of a bacterium. More generally, the term "antimicrobial agent" refers to a compound which specifically inhibits the growth of a microbe, thus the explanation of this term applies also to other microbes and antimicrobial agents. Thus the term includes naturally occurring antibiotics, as well as synthetic and semi-synthetic compounds. Such agents may have either bactericidal or bacteriostatic activity. In general, if an antibacterial agent is bacteriostatic, it means that the agent essentially stops bacterial cell growth (but does not kill the bacteria); if the agent is bactericidal, it means that the agent kills the bacterial cells (and may stop growth before killing the bacteria). However the term is specifically distinguished from compounds which are generally toxic to cells. Some examples of classes of antibacterial agents are quinolones (gyrase inhibitors), aminoglycosides, glycopeptides, sulfonamides, macrolides, β-lactams, and tetracyclines. The efflux pump inhibitors of this invention may be antimicrobial (e.g., antibacterial) agents when used alone, and/or they may potentiate the activity of another antimicrobial agent (increase the susceptibility of the microbe for that other antimicrobial agent), and/or they may reduce the virulence of a pathogen.

A "sub-inhibitory concentration" of an antibacterial agent is a concentration which is greater than zero, but less than the concentration which would inhibit the majority of the cells in a bacterial population of that specific bacterial strain. (Similarly for other microbes.) Thus, while a sub-population of highly sensitive cells may be inhibited, the growth of the majority of the cells will be unaffected or only partially reduced, therefore, the growth of the population of the specific bacteria should preferably be reduced by less than 50%, more preferably less than 30%, and still more preferably less than 10%, in an appropriate medium in the presence of a sub-inhibitory concentration of a specific antibacterial agent. However, in the screening methods of Examples 1 and 3 below, the sub-inhibitory concentration must be high enough so that inhibition of an efflux pump can result in inhibition of growth, and induction of the inactivator of the antibacterial agent respectively. In general, a sub-inhibitory concentration of an antibacterial agent (or antimicrobial agent) is a concentration less than the Minimum Inhibitory Concentration (MIC).

By "comprising" it is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

In another aspect, the invention provides a method for screening for non-tetracycline-specific efflux pump inhibitors. In this method, bacteria expressing a non-tetracycline-specific efflux pump are cultured in an appropriate medium in the presence of a test compound and a second compound. The method involves determining whether the intracellular concentration of the second compound (such as an antimicrobial agent) is elevated in the presence of the test compound. The second compound is one which is normally exported by that pump. Determining whether the intracellular concentration of the second compound is elevated involves detecting the expression of a reporter gene which is transcriptionally linked with a regulatory sequence (a promoter) inducible by an elevated intracellular concentration of the second compound. The second compound is present in the medium at a non-zero concentration which is sub-inhibitory for the bacteria, and which results in an intracellular concentration which is too low to induce expression of the reporter gene unless a pump exporting that compound is inhibited. A test compound is an efflux pump inhibitor if expression of the reporter is higher in the presence of that test compound than in its absence. The second compound is preferably, but not necessarily, an antibacterial agent. In certain embodiments, it is useful if the reporter gene is chromosomally inserted in a single copy, such as in a non-essential gene.

In preferred embodiments, the second compound is an antibacterial agent. In particular embodiments, the recombinant bacterium may be derived from any of a large number of species, including those listed above for the first aspect.

In certain preferred embodiments, expression of the reporter gene from the inducible regulatory sequence is inducible by an elevated concentration of tetracycline. In those embodiments, the regulatory sequence can be a tetA regulatory sequence (such as tetA(A)), which will contain an operator site which can bind the TetR repressor molecule. The bacteria will also express that repressor. In the absence of tetracycline (or with tetracycline at a very low level), the repressor will bind to the operator and the reporter will not be expressed. Thus, if tetracycline is present in the medium at a subinhibitory level with bacteria which express a non-tetracycline-specific efflux pump, the intracellular concentration of tetracycline is maintained at a level low enough that the reporter gene is not expressed (or expressed at a very low level). If a compound (a test compound) is present which inhibits the activity of the efflux pump, the intracellular concentration of tetracycline will rise, releasing TetR from the operator, and the reporter will be expressed. The reporter gene and regulatory sequence are preferably, but not necessarily, inserted in the bacterial chromosome in a single copy. In general, the gene would be inserted in a non-essential gene.

In particular embodiments the efflux pump is a *Pseudomonas aeruginosa* efflux pump, e.g., the mexA/mexB/oprM efflux pump or the efflux pump overexpressed by *P. aeruginosa* Strain K385. In other particular embodiments the efflux pump is a *Pseudomonas aeruginosa*-type efflux pump. In specific embodiments the reporter gene codes for an enzyme, such as the β-galactosidase gene, or other gene with a readily detectable expression product, several of which are well-known to those skilled in the art. Likewise, in a specific embodiment, the cell utilized may be a *Pseudomonas aeruginosa* strain, but other embodiments may utilize other cells, specifically including the bacteria listed in the first aspect above.

Also in particular embodiments, the reporter gene encodes an enzyme, e.g., a β-galactosidase; several appropriate reporters are known to those in the art. In some cases the reporter can provide a calorimetric report, but other reports are also useful. A colorimetric report can be either light absorbing or light emitting. Thus, a colorimetric report may include detection of a molecule which has distinctive light absorption characteristics (a colored molecule), or detection of a light emitting molecule (e.g., a fluorescent molecule).

For a microbe exposed to an antimicrobial agent (including bacteria), the "intracellular concentration" of an antimicrobial agent is the concentration of the agent inside the outermost membrane of the cell. For most microbial species, that membrane is the cytoplasmic membrane, but for Gram-negative bacteria the concentration of the agent in the periplasmic space may be the significant intracellular concentration (e.g., for β-lactams). For Gram-negative bacteria, the relevant intracellular concentration of an antibacterial agent is the concentration in the cellular space which provides access to the primary target of the antibacterial agent.

The term "recombinant microbe" refers to a microbial strain in which has been inserted, through the actions of a person, a DNA construct or sequence which was not previously found in that microbe, or which has been inserted at a different location within the cell or chromosome of that microbe. The term does not include natural genetic exchange such as conjugation between naturally occurring organisms. The term specifically includes recombinant bacteria. For most purposes it is preferable that the inserted DNA sequence should be a stable insertion, meaning that the sequence should be consistently replicated and transmitted to progeny microbes as growth occurs. Such progeny are also "recombinant" as used herein.

The term "expression" of a gene refers to the cellular processes of transcription and translation to produce a polypeptide product. In this context, the term further implies that the expression product is functional, in the sense that it is readily detectable by the means appropriate for that specific reporter. Thus, for an enzymatic reporter, the product exhibits the normal enzymatic activity.

The term "an elevated concentration" refers to an intracellular concentration, indicating that the compound, generally an antibacterial agent, is at a higher concentration than in the absence of another compound, generally a test compound or an efflux pump inhibitor. Thus, in the description of the screening methods, an elevated intracellular concentration of an antibacterial agent is a concentration higher than that existing in the absence of the test compound or of a known efflux pump inhibitor. This elevated concentration may be lower, the same as, or higher, than the concentration existing in the medium.

The term "single copy" indicates that the nucleotide sequence to which the term refers is present in only a single copy in each chromosome set. This is specifically distinguished from the presence of the nucleotide sequence in multi-copy plasmids, where the sequence would be present in a single cell in varying numbers greater than one.

Also in reference to the nucleotide sequence inserted in a cell, the term "chromosomally inserted" indicates that the sequence is inserted and covalently linked in a chromosome of the cell in question. This implies that the sequence will be replicated, along with the rest of the chromosome, in the normal cellular replication process. Again, this is specifically distinguished from having a nucleotide sequence present in a plasmid within the cell which is independent of the cellular chromosome.

A "reporter gene" is a nucleotide sequence which codes for a product which is readily detectable. Some such reporters are enzymes which are detected by the enzymatic activity of the product. A specific example is the β-galactosidase gene. However, numerous other reporter genes exist and are known to those skilled in the art.

A "regulatory sequence" is a nucleotide sequence which controls when and at what level the associated coding sequence will be expressed. In the context of the expression of a gene, the term "inducible" means that the translation of a coding sequence from a regulatory sequence is increased in the presence of a certain set of conditions. So, for the case of a regulatory sequence which is inducible by an antibacterial agent, the expression of the associated coding sequence is increased when the antibacterial agent is present to a sufficiently high concentration. Such induction may occur by a variety of mechanisms, specifically including a derepression mechanism, where a repressor molecule is inactivated by the presence of an antibacterial agent at a sufficiently high concentration.

In another aspect, the invention provides a method of screening for an efflux pump inhibitor, including the steps of contacting recombinant microbial cells with a test compound and determining whether the recombinant microbial cells grow in the presence of the test compound. The recombinant microbe is constructed so that the microbial cells will grow if an efflux pump is inhibited, but will not grow if an efflux pump is not inhibited. The test compound is an efflux pump inhibitor if the recombinant microbial cells grow in the presence of test compound but not in the absence of test compound. This method is a positive growth screen for efflux pump inhibitors.

In particular preferred embodiments this method involves contacting the recombinant microbial cells with a test compound, an inducing agent, and a concentration of an antimicrobial agent above the MIC of the recombinant microbial cells. The antimicrobial agent is not effluxed or specifically inactivated by the recombinant microbial cells in the absence of induction of an inactivator, and the inducing agent induces an inactivator of the antimicrobial agent. Also in particular embodiments, the recombinant microbe is a recombinant bacteria. The inactivator can be a β-lactamase and the antibacterial agent a β-lactam cleaveable by that β-lactamase. Specifically, in one embodiment, the β-lactamase gene can be the blaS gene, and the β-lactam a cleaveable carbapenem. The blaS gene was identified and suitable sources reported in J. Dufresne et al., 1988, *Antimicrob. Agents Chemother.* 32: 819–826. Further, in particular embodiments, the promoter is a tetA promoter, and the recombinant bacterial cells produce functional repressor from a tetR gene which will bind to that promoter. Preferably, but not necessarily, that promoter and β-lactamase gene are inserted in the bacterial chromosome in a single copy.

In another aspect, this invention provides a method for treating a microbial infection, e.g., a bacterial infection, in an animal by administering to an animal suffering from such an infection an efflux pump inhibitor in an amount sufficient to reduce efflux pump activity, where the inhibitor is one which decreases the pathogenicity of the microbe. Such a decrease in pathogenicity can be obtained, for example, by interfering with bacterial iron acquisition by inhibiting the transport of siderophores. The pathogenicity may also be reduced by reducing or eliminating the microbial products which cause tissue-damaging effects to the host. Other methods of reducing pathogenicity are, however, also within this aspect. The animal may be, for example, chickens and turkeys, and in certain preferred embodiments is a mammal.

In certain preferred embodiments the microbial infection may be due to bacteria, which may, for example, be any of the bacterial species indicated in the first aspect above.

In a related aspect, this invention provides a method of treating an animal suffering from a microbial infection by administering to the animal an efflux pump inhibitor in an amount sufficient to reduce efflux pump activity. In this aspect, the efflux pump inhibitor in one which reduces the in vivo viability of a microbe involved in the infection. By reducing the in vivo viability, the infected animal can more readily clear its body of the infection, or the microbes may even be killed. In particular embodiments the animal is a mammal. Also in particular embodiments, the microbe may be from one of a variety of pathogenic bacterial species, specifically including those listed above in the first aspect.

The term "in vivo viability" refers to the ability of a microbe, e.g., a bacterium, to survive or grow in a host, such as an animal. Therefore, an efflux pump inhibitor which reduces the in vivo viability of a microbe may stop the growth of the microbe and/or kill the microbe. Such efflux pump inhibitors, therefore are antimicrobial agents.

In a further related aspect, this invention includes a method for prophylactic treatment of a mammal. In this method, an efflux pump inhibitor which reduces the pathogenicity of a microbe is administered to a mammal at risk of a microbial infection, e.g., a bacterial infection.

In a related aspect, the invention provides a method for treating a microbial infection in an animal, specifically including in a mammal, by treating an animal suffering from such an infection with an antimicrobial agent and an efflux pump inhibitor which increase the susceptibility of the microbe for that antimicrobial agent. In this way a microbe involved in the infection can be treated using the antimicrobial agent in smaller quantities, or can be treated with an antimicrobial agent which is not therapeutically effective when used in the absence of the efflux pump inhibitor. Thus, this method of treatment is especially appropriate for the treatment of infections involving microbial strains which are difficult to treat using an antimicrobial agent alone due to a need for high dosage levels (which can cause undesirable side effects), or due to lack of any clinically effective antimicrobial agents. However, it is also appropriate for treating infections involving microbes which are susceptible to particular antimicrobial agents as a way to reduce the dosage of those particular agents. This can reduce the risk of side effects, but can also reduce the selection effect for highly resistant microbes resulting from the consistent high level use of a particular antimicrobial agent. In particular embodiments the microbe is a bacterium, which may, for example, be from any of the species indicated in the first aspect above. Also in particular embodiments various antibacterial agents can be used. These include quinolones, tetracyclines, glycopeptides, aminoglycosides, β-lactams, rifamycins, coumermycins, macrolides, and chloramphenicol. In particular embodiments an antibiotic of the above classes can be, for example, one of the following:

b-Lactam Antibiotics imipenem, meropenem, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefmetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, LY206763

Macrolides azithromycin, clarithromycin, erythromycin, oleandomycin, rokitamycin, rosaramicin, roxithromycin, troleandomycin Ouinolones amifloxacin, cinoxacin, ciprofloxacin, enoxacin, fleroxacin, flumequine, lomefloxacin, nalidixic acid, norfloxacin, ofloxacin, levofloxacin, oxolinic acid, pefloxacin, rosoxacin, temafloxacin, tosufloxacin, sparfloxacin, clinafloxacin, PD131628, PD138312, PD140248, Q-35, AM-1155, NM394, T-3761, rufloxacin, OPC-17116, DU-6859a (identified in Sato, K. et al., 1992, *Antimicrob Agents Chemother.* 37:1491–98), DV-7751a (identified in Tanaka, M. et al., 1992, *Antimicrob. Agents Chemother.* 37:2212–18)

Tetracyclines chlortetracycline, demeclocycline, doxycycline, lymecycline, methacycline, minocycline, oxytetracycline, tetracycline Aminoglycosides amikacin, arbekacin, butirosin, dibekacin, fortimicins, gentamicin, kanamycin, meomycin, netilmicin, ribostamycin, sisomicin, spectinomycin, streptomycin, tobramycin, clindamycin, lincomycin In a further related aspect, this invention includes a method for prophylactic treatment of a mammal. In this method, an antimicrobial agent and an efflux pump inhibitor is administered to a mammal at risk of a microbial infection, e.g., a bacterial infection.

In the context of the response of a microbe, such as a bacterium, to an antimicrobial agent, the term "susceptibility" refers to the sensitivity of the microbe for the presence of the antimicrobial agent. So, to increase the susceptibility means that the microbe will be inhibited by a lower concentration of the antimicrobial agent in the medium surrounding the microbial cells. This is equivalent to saying that the microbe is more sensitive to the antimicrobial agent. In most cases the minimum inhibitory concentration (MIC) of that antimicrobial agent will have been reduced.

As used herein, the term "treating" refers to administering a pharmaceutical composition for prophylactic and/or therapeutic purposes. The term "prophylactic treatment" refers to treating a patient who is not yet infected, but who is susceptible to, or otherwise at risk of, a particular infection. The term "therapeutic treatment" refers to administering treatment to a patient already suffering from an infection. Thus, in preferred embodiments, treating is the administration to a mammal (either for therapeutic or prophylactic purposes) of therapeutically effective amounts of a potentiator and an antibacterial (or antimicrobial) agent in combination (either simultaneously or serially).

By "therapeutically effective amount" or "pharmaceutically effective amount" is meant an amount of an efflux pump inhibitor, or amounts individually of an efflux pump inhibitor and an antimicrobial agent, as disclosed for this invention, which have a therapeutic effect, which generally refers to the inhibition to some extent of the normal metabolism of microbial cells causing or contributing to a microbial infection. The doses of efflux pump inhibitor and antimicrobial agent which are useful in combination as a treatment are therapeutically effective amounts. Thus, as used herein, a therapeutically effective amount means those amounts of efflux pump inhibitor and antimicrobial agent which, when used in combination, produce the desired therapeutic effect as judged by clinical trial results and/or model animal infection studies. In particular embodiments, the efflux pump inhibitor and antimicrobial agent are combined in pre-determined proportions and thus a therapeutically effective amount would be an amount of the combination. This amount and the amount of the efflux pump inhibitor and antimicrobial agent individually can be routinely determined by one of skill in the art, and will vary, depending on several factors, such as the particular microbial strain involved and the particular efflux pump inhibitor and antimicrobial agent used. This amount can further depend upon the patient's height, weight, sex, age and medical history. For prophylactic treatments, a therapeutically effective amount is that amount which would be effective if a microbial infection existed.

A therapeutic effect relieves, to some extent, one or more of the symptoms of the infection, and includes curing an infection. "Curing" means that the symptoms of active infection are eliminated, including the elimination of excessive members of viable microbe of those involved in the infection. However, certain long-term or permanent effects of the infection may exist even after a cure is obtained (such as extensive tissue damage).

The term "microbial infection" refers to the invasion of the host mammal by pathogenic microbes. This includes the excessive growth of microbes which are normally present in or on the body of a mammal. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection.

The term "administration" or "administering" refers to a method of giving a dosage of an antimicrobial pharmaceutical composition to a mammal, where the method is, e.g., topical, oral, intravenous, intraperitoneal, or intramuscular. The preferred method of administration can vary depending on various factors, e.g., the components of the pharmaceutical composition, the site of the potential or actual bacterial infection, the microbe involved, and the severity of an actual microbial infection.

The term "mammal" is used in its usual biological sense. Thus, it specifically includes humans, dogs, and cats, but also includes many other species.

In another aspect, this invention also features a method of inhibiting a membrane channel in a cellular membrane, involving contacting the membrane channel with a membrane channel inhibitor, where the inhibitor reduces the effluxing capacity of the membrane channel. In specific embodiments, at least one polypeptide of the membrane channel has at least 50% amino acid sequence similarity with a polypeptide of the mexA/mexB/oprM efflux pump, or of the efflux pump overexpressed by *Pseudomonas aeruginosa* Strain K385.

As used herein, the term "membrane channel" refers to a protein assembly located in the cellular membrane of a cell which allows the transport of one or more types of molecules across the membrane. Such transport may be either passive transport in response to concentration gradients, or may be active transport which depends upon a cellular energy source.

A "membrane channel inhibitor" then is, similar to an efflux pump inhibitor, a compound which slows or prevents the transport of molecules across the cellular membrane using the corresponding membrane channel.

This invention also features a method of enhancing the antimicrobial activity of an antimicrobial agent against a microbe, in which such a microbe is contacted with a non-tetracycline specific efflux pump inhibitor to an efflux pump in the cell, and an antibacterial agent. Thus, this method makes an antimicrobial agent more effective against a cell which expresses an efflux pump when the cell is treated with the combination of an antimicrobial agent and a non-tetracycline-specific efflux pump inhibitor. In particular embodiments the microbe is a bacterium, such as any of those indicated in the first aspect above; the antibacterial agent can be selected from a number of structural classes of antibiotics including, e.g., β-lactams, glycopeptides, aminoglycosides, quinolones, tetracyclines, rifamycins, coumermycins, macrolides, and chloramphenicol. In particular embodiments an antibiotic of the above classes can be as stated above.

In a further aspect this invention provides pharmaceutical compositions effective for treatment of an infection of a mammal by a bacterium, which include a pharmaceutically acceptable carrier and an efflux pump inhibitor. Such compositions may contain ef flux pump inhibitors which are effective antibacterial agents without another antibacterial agent present. Such compositions may be used alone to treat an infection. In other compositions the efflux pump inhibitor increases the susceptibility of a bacterium for another antibacterial agent, so such compositions would be used in combination with such other antibacterial agent. The invention also provides pharmaceutical compositions similarly effective for treatment of an infection of a mammal which include an efflux pump inhibitor and an antibacterial agent. Similarly, the invention provides antibacterial formulations which include an antibacterial agent, an efflux pump inhibitor, and a carrier.

In certain preferred embodiments an efflux pump inhibitor has a structure which is shown by one of the generic structures 1–4 below:

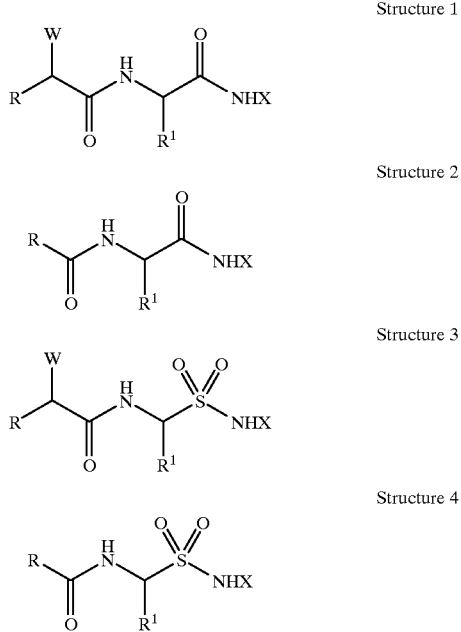

Structure 1

Structure 2

Structure 3

Structure 4 wherein
R=alkyl ($C_1$–$C_4$), fluoroalkyl ($C_1$–$C_4$), perfluoroalkyl ($C_1$–$C_4$), alkoxy ($C_1$–$C_4$), alkylthio ($C_1$–$C_4$), halogen (Br, Cl, F or I), aryl ($C_6$–$C_{10}$), monosubstituted aryl ($C_6$–$C_{10}$) [optionally substituted with alkyl ($C_1$–$C_4$), alkoxy ($C_1$–$C_4$), alkylthio ($C_1$–$C_4$), halogen (Br, Cl, F or I), amino, monosubstituted amino [optionally substituted with alkyl ($C_1$–$C_4$)], disubstituted amino [optionally substituted with any combination of alkyl ($C_1$–$C_4$)], or hydroxyl]], disubstituted aryl ($C_6$–$C_{10}$) [any combination of alkyl ($C_1$–$C_4$), alkoxy ($C_1$–$C_4$), alkylthio ($C_1$–$C_4$), halogen (Br, Cl, F or I) and amino], 2-(or 3-)-thienyl, 2-(or 3-)-furanyl, or 2-(3- or 4-)-pyridyl, W=H, $NH_2$, monosubstituted amino [optionally substituted with alkyl ($C_1$–$C_4$)], disubstituted amino [optionally substituted with any combination of alkyl ($C_1$–$C_4$)], azaheterocycles [such as N-morpholinyl, N-piperazinyl, N-pyrrolidinyl, N-imidazolyl, N-pyrrolyl, N-pyrazolyl, N-triazolyl, or N-tetrazolyl], halogen (Br, Cl, F, I), hydroxyl, alkoxy ($C_1$–$C_4$), alkylthio ($C_1$–$C_4$), $R^1$=$(CH_2)_n NR^b R^c$, $(CH_2)_n NHC=(NR^a)NR^b R^c$, $(CH_2)_n SNHC=(NR^a)NR^b R^c$, $(CH_2)_n C=(NR^a)NR^b R^c$, $(CH_2)_n N=CNR^b R^c$, (n=2–4); $R^a$ ($R^b$ or $R^c$)=H, alkyl ($C_1$–$C_4$), aryl ($C_6$), substituted aryl, benzyl, substituted benzy [optionally substituted with alkyl ($C_1$–$C_4$), alkoxy ($C_1$–$C_4$), alkylthio ($C_1$–$C_4$) , halogen (Br, Cl, F or I), or amino], or alternatively $R^a+R^b=(CH_2)_{2-3}$ or —CH=CH—, X=aryl ($C_6$–$C_{10}$), —$(CH_2)_{0-2}$aryl ($C_6$–$C_{10}$), substituted aryl ($C_6$–$C_{10}$) [optionally substituted with with alkyl ($C_1$–$C_4$), alkoxy ($C_1$–$C_4$), alkylthio ($C_1$–$C_4$), halogen (Br, Cl, F or I), or amino], substituted —$(CH_2)_{0-2}$aryl ($C_6$–$C_{10}$) [substitution on aryl unit with alkyl ($C_1$–$C_4$), alkoxy ($C_1$–$C_4$), alkylthio ($C_1$–$C_4$), halogen (Br, Cl, F or I), or amino], 2-(or 3-)-thienyl, 2-(or 3-)-furyl, 2-(3- or 4-)-pyridyl, benzofuranyl [at any position on the benzofuran ring], benzothienyl [at any position on the benzothiophene ring].

Where there are centers of asymmetry, the absolute stereochemistry can be either R or S configuration, or there can be a racemic mixture, all within the generic structural description.

Compounds within the generic description above can be obtained by synthetic chemistry methods known to those skilled in the chemical arts.

A "carrier" or "excipient" is a compound or material used to facilitate administration of the compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants such as are commonly used in the art may be included. These and other such compounds are described in the literature, e.g., in the *Merck Index,* Merck & Company, Rahway, N.J. Considerations for the inclusion of various components in pharmaceutical compositions are described, e.g., in Gilman et al. (Eds.) (1990); *Goodman and Gilman's: The Pharmacological Basis of Therapeutics,* 8th Ed., Pergamon Press.

In yet another aspect, the invention provides a method of suppressing growth of a bacterium expressing a non-tetracycline-specific efflux pump, by contacting that bacterium with a non-tetracycline-specific efflux pump inhibitor in the presence of a concentration of antibacterial agent below the MIC of the bacterium. This method is useful, for example, to prevent or cure contamination of a cell culture by a bacterium possessing an efflux pump. However, it applies to any situation where such growth suppression is desirable.

In a related aspect, the invention provides a method of suppressing growth of a bacterium which involves contacting the bacterium with an efflux pump inhibitor which reduces the expression of a component of an efflux pump. Such an inhibitor can act on the regulation of that expression in number of different ways. It may, for example, enhance the production of a repressor molecule which prevents expression of an efflux pump component. Another possible mechanism is if the inhibitor blocks the release of a repressor molecule. Examples of such a repressor is MarR in *E. coli* (Seoane and Levy, 1994, *Abstr. of the Am. Soc. for Microbiol. Gen. Meeting,* Las Vegas, Nev., Abstr. H-26). An example of a positive regulator is BmrR in *Bacillus subtilis* (Ahmed et al., 1994, *J. Biol. Chem.*).

In another related aspect, the invention provides a method for reducing a population of a bacterial strain, involving contacting the population with an efflux pump inhibitor which inhibits a component of an efflux pump expressed in the bacteria in that population, which is essential for the growth of the bacteria expressing that efflux pump. In particular embodiments, that component is a cytoplasmic membrane component. As indicated above, such efflux pump inhibitors may act in various ways, including, but not limited to, acting directly on the essential component, or acting to inhibit the expression of that component.

The term "reducing a population" means that the bacteria of that population are being killed. This is distinguished from a bacteriostatic agent which prevents the bacteria from growing and multiplying. Accordingly, in the context of this aspect, an "essential component" of an efflux pump is one which is essential to the in vivo survival of the bacteria, i.e., the survival in a host.

In yet another aspect, this invention provides a method for enhancing growth of am animal by administering an efflux pump inhibitor to the animal, which inhibits an efflux pump expressed in a bacterial strain in the animal, and which inhibits the growth of that bacterial strain. Such a growth enhancing effect may result from the reduced energy consumption by the bacteria, which increases the food energy available to the animal. This method is appropriate, for example, for use with cattle, swine, and fowl such as chickens and turkeys.

Other features and advantages of the invention will be apparent from the following description of the preferred embodiments, and from the claims.

BRIEF DESCRIPTION OF THE FIGURES

FIG. 1 shows the categorization of efflux pumps into three major families.

FIG. 3 shows the expected results from the screen described in Example 1 (Growth Inhibition Screen) using a bacterial strain which overproduces an efflux pump which will transport ciprofloxacin, and a strain which does not produce such a pump. The overproducing strain, in the presence of an efflux pump inhibitor, plus a sub-MIC concentration of ciprofloxacin, will exhibit no growth.

FIG. 5 shows the components and their relationships of the positive growth screen from Example 3.

FIG. 7 indicates the efflux pump characteristics of the four strains of *Pseudomonas aeruginosa* used in the in vitro characterization of L-phenylalanyl-L-arginyl-β-naphthylamide.

FIG. 8 shows the synergistic effect of L-phenylalanyl-L-arginyl-β-naphthylamide with, respectively, tetracycline and ciprofloxacin for each of the four strains of *Pseudomonas aeruginosa* identified in FIG. 4.

FIG. 10 indicates the antibiotic susceptibility (MICs) of *Pseudomonas aeruginosa* strains PAO1 and K385 for 13 antibiotics in the presence and absence of 20 μg/ml L-phenylalanyl-L-arginyl-β-naphthylamide.

FIG. 11 relates the degree of hydrophobicity of four amphoteric fluoroquinolones with the fold increase in susceptibility caused by L-phenylalanyl-L-arginyl-β-naphthylamide, showing a direct relationship.

FIG. 16 shows the species from which strains were tested for the potentiation of ciprofloxacin by L-phenylalanyl-L-arginyl-β-naphthylamide, indicating the fraction of tested strains from each species which showed such potentiation.

DESCRIPTION OF THE PREFERRED EMBODIMENTS

Physiological Role for Efflux Pumps

Figure 2:
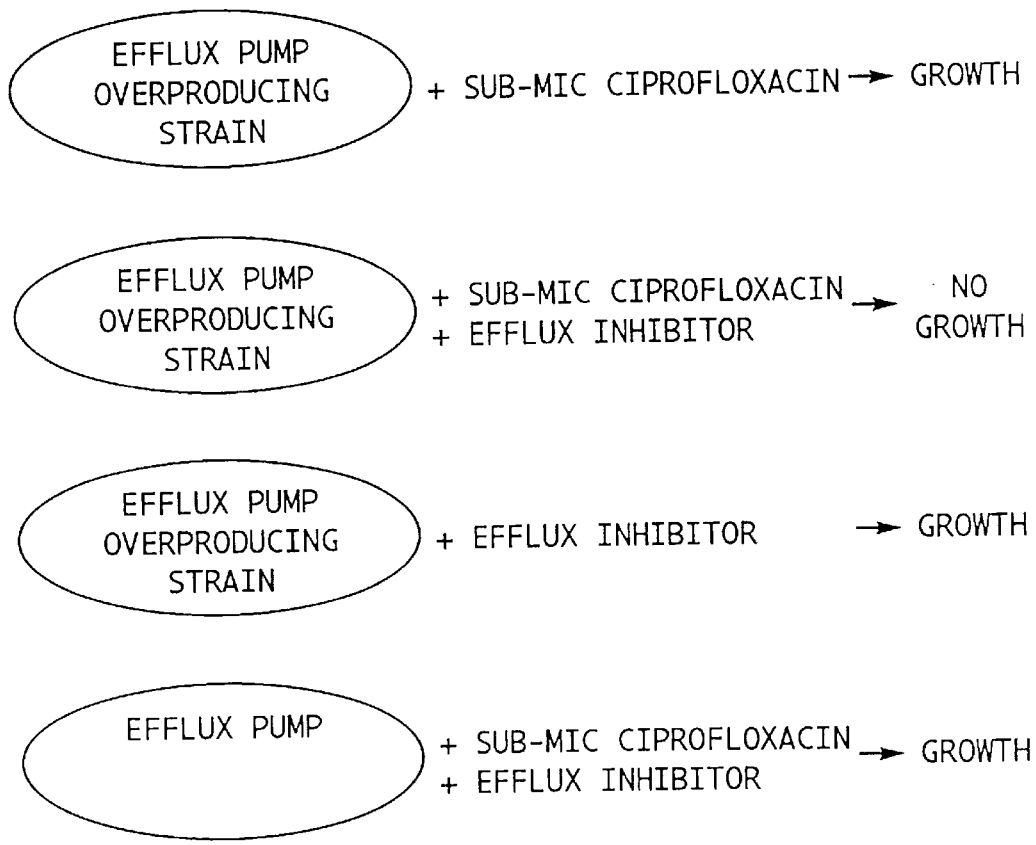
FIG. 2 is a schematic representation of the *Pseudomonas aeruginosa* efflux pump, MexA/MexB/OprM, showing the expected spatial relationship of the three components. In this depiction, MexE spans the cytoplasmic membrane, MexA bridges the periplasmic space, and OprM spans the outer membrane. The right hand figure shows that if a test compound inhibits efflux (such as by inhibiting a component of the pump) an antibiotic which is normally effluxed (such as ciprofloxacin) will accumulate in the cytoplasm of the bacteria.
Figure 4:
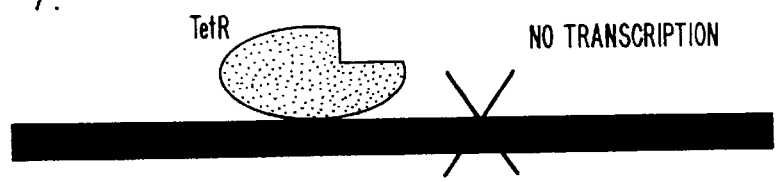
FIG. 4 is a general schematic depiction of the reporter method described in Example 2.

Bacteria use transporters to export molecules from the cytoplasm to the outer medium. Most of the known transporters are involved in transport of molecules that otherwise could not diffuse through the membranes or would diffuse very slowly. Molecules exported to the outside medium include proteins, peptides, capsular polysaccharides, oligosaccharides, siderophores and drugs. Transporters allow the passage of molecules through the cytoplasmic membrane and through the outer membrane in Gram-negative bacteria and can be divided in three main families according to their sequence homology and energy source (H. Nikaido, 1994, *Science* 264: 382–388; Dinh et al., 1994, *J.*

*Bacteriol.* 176: 3825–3831). (See FIG. 1.) The ABC (ATP-binding cassette) family includes drug and enzyme transporters, this family include transporters involved in the secretion of proteins. For example HlyD is involved in the export of hemolysin in *E. coli,* and in *P. aeruginosa* alkaline proteases are exported by the AprE system. The multidrug efflux pump found in mammalian cells, P-1 glycoprotein and MsrA of *Staphylococcus aureus* belong to this group. The major facilitator superfamily includes specific efflux pumps such as Tet efflux pump and are related to transport systems involved in uptake of nutrient from the outside medium such as Xyl system. The major facilitator family uses proton motive force as the energy source. The third family, heavy metal resistance/nodulation factor family, includes transporters involved in the secretion of siderophores, for example MexA in *P. aeruginosa,* the export of nodulation factors in *Rhizobium meliloti,* and efflux pumps with broad substrate specificity involved in the export of antibiotics, such as mex pumps in *P. aeruginosa* or Acr in *E. coli.*

Iron Metabolism and Efflux Pumps

Iron is the most common transition metal in living organisms, and is an essential nutrient in all pathogenic bacteria (Wooldridge and Williams, 1993, *FEMS Microbiol. Rev.* 12: 325–348). Iron availability plays a crucial role in the establishment and progress of infection. Extracellular iron in the human body is bound to high affinity iron-binding proteins transferrin and lactoferrin. Transferrin and lactoferrin contribute to host defense against infection by limiting the iron available for a microbial pathogen. Bacteria need iron to survive and replicate in the body and they have developed different strategies to obtain iron. Bacteria synthesize and export to the external medium molecules that have high affinity for iron and when these molecules chelate iron, they are transported back to the cell (Wooldridge and Williams, 1993). These molecules are called generically siderophores and are needed for the bacterial infection to proceed. The synthesis of siderophores and their efflux and uptake related systems are tightly regulated by iron availability in the external medium. Two main siderophores are synthesized by *P. aeruginosa,* pyoverdin and pyochelin. Both siderophores can remove transferrin-bound iron (Sriyosachati and Cox, 1986, *Infect. & Imm.* 52: 885–891; C. Wolz, 1994, *Infect. & Imm.* 62: 4021–4027). Pyoverdin is the more effective iron scavenger and has a higher affinity for iron than pyochelin; it can effectively remove iron from transferrin-iron complexes. Pyoverdin is a large, ca.1.5 KDa, water soluble molecule. It cannot diffuse through the lipid layer of membranes and needs transport systems to cross the plasma membrane. While siderophore uptake systems have been described in the literature (Gensberg and Smith, 1992, *J. Gen. Microbiol.* 138: 2381–2387), it is only now that the identity of the secretion pathway has been inferred. Efflux pumps are involved in siderophore export because they are needed by bacteria to secrete siderophores that otherwise could not cross the outer and inner membranes due to their large size and hydrophilic nature. In *P. aeruginosa,* the expression of mexAB, oprM operon is regulated by the iron content of the medium and is co-regulated with the production and uptake of components of the major siderophore pyoverdin (Poole et al., 1993a). Since iron transport is essential for successful *P. aeruginosa* infections (P. Sokol, 1987, *Infect. & Imm.* 55: 2021–2025; B. Haas, 1991, *Infect. & Imm.* 59: 3997–4000; Woods and Iglewski, 1982, *Infect. & Imm.* 35: 461–464), the inhibition of the pumps will interfere with bacterial iron metabolism and thus yield attenuated virulence.

Active Efflux as a Mechanism of Drug Resistance

Resistance caused by the active pumping out, or transmembrane efflux, of noxious agents began to attract the attention of scientists around 1980, when S. B. Levy and co-workers showed that plasmid-coded tetracycline resistance of *E. coli* is based on energy-dependant efflux. This was followed shortly afterward by the demonstration that the plasmid-coded cadmium resistance of *Staphylococcus aureus* was also based on an efflux mechanism.

It is increasingly recognized that active efflux plays a major role in the resistance of many organisms to many agents; among the three clinically relevant resistance mechanisms listed by Neu as involving reduced permeability, two, and possibly all three, are mainly due to efflux. (i) Beginning with the demonstration, by Neal and Chater in 1987, that *Streptomyces coelicolor* protects itself from the methylenomycin it produces, a number of antibiotic efflux genes have been identified in antibiotic-producing Streptomyces species. Some of them belong to the MF family and others to the ABC family. (ii) A new type of plasmid-mediated macrolide resistance in *S. aureus,* which was originally thought to be due to decreased permeability, was shown to involve active efflux. (iii) The most common mechanism of chloramphenicol resistance involves the enzymatic acetylation of the drug. The "nonenzymatic mechanism of chloramphenicol resistance," again originally thought to be due to decreased influx of chloramphenicol, was shown to be caused by active efflux, because the cmLA gene from transposon Tn1696 appears to be an active efflux transporter of MF family. Furthermore, *Haemophilus influenzae* contains a homologous chromosomal gene, and some of the nonenzymatic resistance of this (and perhaps many other) species is very likely due to active efflux. (iv) Plasmid-coded resistance to quaternary ammonium antiseptics in staphylococci was shown to involve efflux, through the QasA-QacB transporter of MF type and the QacC transporter of Smr type. These proteins also pump out some basic dyes. (v) Active efflux of norfloxacin, a fluoroquinolone, was first discovered in wild-type *E. coli.* A gene (norA) involved in a similar active efflux process was later sequenced from the chromosome of a resistant mutant of *S. aureus* and was shown to code for an efflux transporter of the MF family. NorA pumps out a variety of fluoroquinolones.

Identification of Efflux Pumps

The existence of an efflux pump in a cell can be detected when de-energized cells accumulate more of a substance than do energized cells. (S. B. Levy, 1992, *Antimicrob. Agents Chemother.* 36:695–703.) The de-energizing involves making energy unavailable to an energy dependent efflux pump. This is accomplished, for example, by depolarizing an energized membrane, eliminating the proton motive force (PMF). This is appropriate since a number of identified efflux pumps are driven by PMF. The concentration difference can be determined directly, by the accumulation of the substance in the cell, or, alternatively, cells which have accumulated a substance may be placed into a medium without that substance and the rate of loss from the cells or the rate of gain by the medium, can be measured in the presence and absence of energy. For different efflux systems, various energy blockers can be used, for example, cyanide, 2,4-dinitrophenol (dnp), and carbonyl cyanide m-chlorophenylhydrazone (cccp). For some efflux pumps, the efflux activity can also be studied using everted vesicles with membrane proteins in those vesicles. (S. B. Levy, 1992.)

Figure 6:
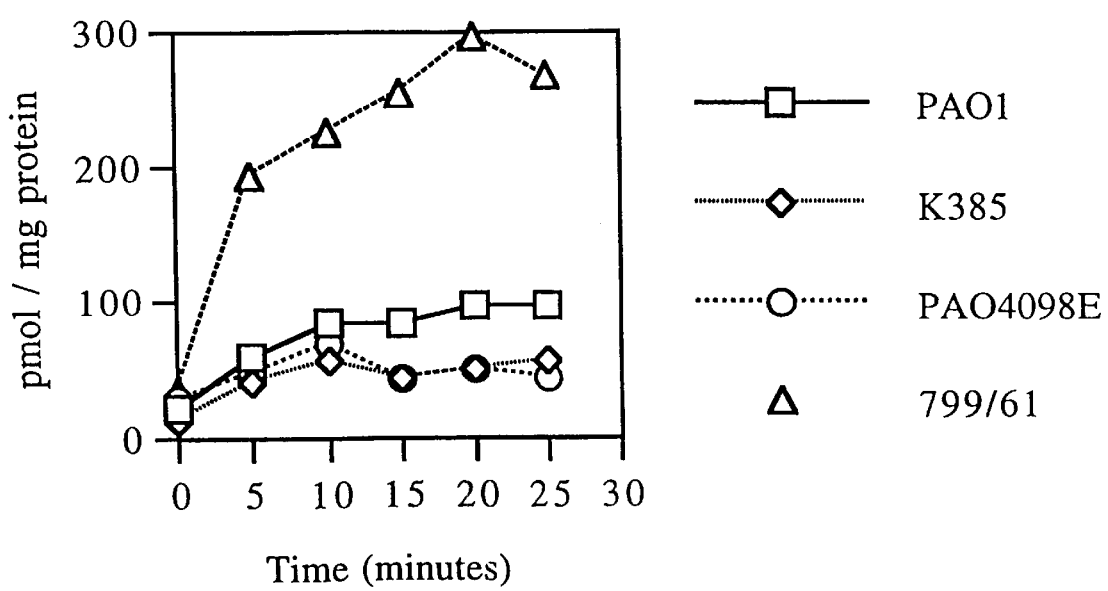
FIG. 6 shows the intracellular accumulation of tetracycline in four strains of *Pseudomonas aeruginosa*. The hyper-susceptible strain 799/61 showed the highest internal concentration.

Alternatively, efflux pumps are identified by their ability to lower the accumulation of a substrate in a cell. Efflux pumps involved in drug resistance can be identified because they confer resistance to antibiotics. Efflux pumps involved in multidrug resistance in bacteria usually give an intermediate level of resistance to a broad range of antibiotics. Specific mechanism of resistance, including specific efflux pumps, give a much higher level of resistance to one antibiotic or a group of structurally related antibiotics. A strain that shows low level of resistance to a large number of unrelated antibiotics is likely to express a pump involved in the active export of the antibiotics. To identify whether an efflux pump is involved in antibiotic resistance in a given strain, accumulation experiments should be performed using antibiotics that it is suspected are exported by the efflux pump. The protein pattern in electrophoresis of cytoplasmic membrane proteins should be studied to identify the overexpression of a protein or the appearance of a new band in the protein pattern using gel electrophoresis. For Gram-negative bacteria, the outer membrane proteins should also be studied. Since efflux pumps are a common occurrence in most bacteria, the basal level of antibiotic susceptibility of a wild type might be caused by naturally occurring efflux pumps. Accumulation experiments with such a strain can demonstrate the presence of a pump. Mutants that overexpress the pumps can be isolated using antibiotic-containing media. These mutants will be more resistant to antibiotics and will accumulate lower levels of antibiotics. Also, they could overexpress protein in the cytoplasmic and/or outer membrane. Similarly mutants that are hypersusceptible to antibiotics can be isolated and studied as described above. These mutants should accumulate antibiotic to a higher levels and could have lower expression of proteins in membranes. As an example of antibiotic accumulation in *P. aeruginosa*, tetracycline accumulation was measured in four different *P. aeruginosa* strains: 1) wild type strain PAO1 that produces basal levels of efflux pumps, 2) & 3) strains PAO4098E and K385 derived from PAO1 and overproducers of two different efflux pumps and 4) strain 799/61, a strain that does not produce measurable amounts of any efflux pumps and is hypersusceptible to antibiotics. The basal level of tetracycline accumulation correlated with the amount of efflux pumps produced by these strains. Strain 799/61 accumulated more tetracycline than the wild type PAO1, and the two efflux pump overproducers strains accumulated lower amounts of tetracycline. (See FIG. 6.)

Multidrug Efflux Systems in Bacteria

A significant development in this field has been the discovery of bacterial efflux systems that can handle a wide variety of drugs, reminiscent of the mdr system in mammalian cells. Systems such as QacA, Smr, QacE, or MyrC pump out quaternary amine compounds as well as basic dyes and are often called multidrug efflux systems. However, the substrates of these systems are at least physically similar, being amphophilic molecules with positive charges. In contrast, the Bmr transporter, found in rhodamine-6G-resistant mutant of *Bacillus subtilis*, catalyzed the active efflux not only of cationic dyes such as rhodamine-6G and ethidium bromide, antibiotics puromycin (basic) and netropsin (strongly basic), and an organic cation, tetraphenylphosphonium, but also chloramphenicol (uncharged). It was later shown to pump out fluoroquinolones, most of which should exist as zwitterions at a neutral pH. NorA in *S. aureus* turned out to be a Bmr homolog and was indeed shown to pump out cationic dyes, puromycin, and chloramphenicol, solutes that are unrelated not only in chemical structure but also in physical properties.

Another multidrug efflux system was identified in an *E. coli* mutant resistant to an uncoupler, carbonyl cyanide m-chlorophenylhydrazone (CCCP). This transporter, EmrB, also pumps out such unrelated compounds as phenylmercuric acetate, nalidixic acid (a weak acid), and thiolactomycin (uncharged).

The acrA mutation of *E. coli* K12, which had been thought to produce drug hypersusceptibility by increasing the outer membranes permeability, was shown to inactivate a multidrug efflux complex, AcrAE. In the wild-type acrA$^+$ strain, the steady-state accumulation of acriflavine is extremely low. Because cationic dyes should be concentrated in the cytoplasm in response to the interior-negative potential across the cytoplasmic membrane, this indicates that acriflavine must be pumped out very actively. In an acrA mutant, the steady-state accumulation increases at least fivefold, indicating that the AcrAE efflux system participates in the extrusion of this dye. This solves a long-standing mystery, because no defect has been found in the outer membrane of acrA mutants despite much research, and their outer membrane permeability was shown to be normal at least to one probe. The substrate range of the AcrAE system appears to be very broad and includes hydrophilic antibiotics such as novobiocin, erythromycin (a macrolide), fusidic acid, mitomycin C, and tetracycline, as well as a detergent, sodium dodecylsulfate (SDS).

An alteration at a chromosomal gene cluster of *E. coli*, marRAB, also produces significant resistance to a wide range of antibiotics, including fluoroquinolones, chloramphenicol, tetracycline, and β-lactams. (At least the resistance to fluoroquinolones and tetracycline appears to involve efflux.) MarA, however, is a regulatory protein that affects many processes, and the nature and number of pumps affected by this protein are presently unknown.

Most recently, the well-known intrinsic resistance of *P. aeruginosa* to a large variety of antimicrobials was shown to be due as much to an efflux system as to its low permeability outer membrane. Clinical isolates of *P. aeruginosa*, even when they are free of R plasmids, show widely different levels of "intrinsic" resistance to antimicrobial agents. Furthermore, there is a good correlation among resistance levels to different agents, such as β-lactams, chloramphenicol, tetracycline, and fluoroquinolones. Different levels of intrinsic resistance were thus thought to be caused by corresponding differences in outer membrane permeability. Experiments, however, ruled out this hypothesis. When the accumulation of various drugs was tested, it was discovered that even wild-type strains of *P. aeruginosa* pump out tetracycline, chloramphenicol, and norfloxacin very effectively, and this activity was correlated with the intrinsic resistance level of the strain.

The genetic identity of this efflux system was suggested by the study of K. Poole and associates. (Poole et al., 1993a, *Mol. Microbiol.* 10: 529–544, and Poole et al., 1993b) *J. Bacteriol.* 175: 7363–7372.) These references are hereby incorporated herein, in their entirety, by reference. In that study of Fe$^{3+}$ uptake in *P. aeruginosa*, they cloned an operon, mexA-mexB-oprM, which is believed to function in the export of the siderophore pyoverdine. (The product of ORFC, identified in the above Poole et al. references as OprK, is currently identified as OprM (Poole et al., unpublished information), and is so referenced herein.) MexB has a typical sequence for an RND family transporter. When this operon was inactivated by insertion mutagenesis, the *P. aeruginosa* strain became almost as susceptible as *E. coli* to both chloramphenicol and tetracycline. This suggests that this single efflux system is the major reason that this species displays the generally drug-resistant phenotype.

Active efflux also appears to have a role in the β-lactam resistance of some *Pseudomonas aeruginosa*. *Pseudomonas aeruginosa* produce a chromosomally coded, inducible β-lactamase, and the synergy between this enzyme and the outer membrane barrier explains its resistance to some compounds that act as strong inducers of this enzyme. However, strains with a high intrinsic resistance are also highly resistant to compounds that do not induce much β-lactamase and are quite stable to enzymatic hydrolysis. Further, these strains are unaltered in their target of β-lactam action or in the levels or properties of the β-lactamase. The results suggest that their β-lactam resistance is also caused by active efflux. Unlike other hydrophobic agents, however, some β-lactams cannot cross the cytoplasmic membrane barrier, and their targets are on the periplasmic side of the cytoplasmic membrane. It is useful here to recall that the mammalian mdr protein apparently intercepts its substrate during its transit through the lipid bilayer. Observations on bilayer-impermeant β-lactams gives strong support to this idea.

While the apparently wide substrate specificity of the *P. aeruginosa* efflux system is somewhat surprising, such broad specificity is previously known. For example, the mammalian mdr pump extrudes not only basic compounds, such as doxorubicin, but also neutral compounds, such as taxol, and weakly acidic compounds, such as mithramycin. Indeed, the mammalian mdr pump is inhibited by hydrophobic cephalosporins, which presumably act as substrate analogs.

The Efflux System and the Outer Membrane Barrier

Efflux transporters are located in the cytoplasmic membrane, and thus in Gram-negative bacteria the agents may be assumed to be pumped out into the periplasm (see FIG. 2). If so, the efflux is less likely to make these bacteria more resistant, without additional factors, because the antimicrobial agents will not be able to leave the cells easily owing to the presence of the outer membrane barrier. One way to overcome this barrier was suggested by the presence of accessory proteins that occur together with many efflux transporters of both MF and RND families in Gram-negative cells. These proteins are thought to "bridge" the cytoplasmic transporter and an outer membrane channel so that the drugs can be extruded directly into the surrounding medium rather than into the periplasm (FIG. 2), as they are related to a group of proteins in Gram-negative bacteria, including HlyD, LktD, CyaD, AprE, and CvaA, which similarly act as bridges and help extrude their substrates, proteins, directly into external media. It is thus likely that the accessory proteins form complexes with some channel proteins in the outer membrane, for example, TolC. This model was supported recently by the discovery of the mexA-mexB-oprM system of *P. aeruginosa*. This presumed operon codes not only for an accessory protein MexA but also for an outer membrane protein OprM, and this gene organization suggests that the three proteins form a complex that likely forms a continuous channel opening into the external medium (FIG. 2). Indeed, OprM shows sequence homology with CyaE and PrtF, outer membrane proteins that are presumably involved in the formation of three component export complexes containing a transporter in the cytoplasmic protein, a periplasmic accessory protein, and an outer membrane channel, which function in the direct export of cytolysin and proteases B and C into the medium in *Bordatella pertussis* and *Erwinia chrysanthemi*, respectively. Furthermore, inactivation of OprM led to hypersusceptibility to many agents, just like the inactivation of MexA. It is not yet known how the systems that do not contain accessory proteins extrude the agents efficiently into the medium. However, for those bacteria which do express such an outer membrane protein, such as OprM and the 50-kDa protein overexpressed by *P. aeruginosa* K385, that outer membrane provides another target for efflux pump inhibitors as described herein.

As mentioned, the low permeability of the outer membrane alone may not produce clinically significant levels of resistance, and a second contributor would then be required for such high-level resistance. In many systems, the active efflux system appears to be this second factor. But this does not mean that the outer membrane barrier is not important. Because the intracellular concentration of any drug is the result of a balance between influx and efflux, it is likely that the slow influx of various agents through the low permeability outer membrane makes efflux an especially effective mechanism for resistance in organisms such as *P. aeruginosa*. That is, even if organisms with a high-permeability outer membrane, such as *E. coli*, had an efflux machinery of comparable efficiency, it would not produce as significant a level of resistance unless the agent has a size or structure that slows down its permeation through the outer membrane.

In this connection, it is important that *E. coli* mutants at the marRAB cluster produce smaller amounts of OmpF porin, which produces a larger channel among the two nonspecific porins of *E. coli* and therefore plays a predominant role in the penetration of most antibiotics. With the influx thus decreased, active efflux can create a much higher resistance. Some plasmid-coded efflux transporters in Gram-negative bacteria may also use a similar mechanism. An R plasmid repressing the synthesis of OmpF porin was reported as early as 1978. The gene for nonenzymatic chloramphenicol resistance in *Haemophilus influenzae*, most likely a homolog of CmlA efflux transporter (see above), represses the synthesis of the major porin in this organism. Cloned CmlA gene represses porin synthesis in *E. coli*. A clinical isolate of *Salmonella typhi* with nonenzymatic chloramphenicol resistance, probably with a transposon containing OmpF. This ability of some plasmid- or transposon-based efflux genes to decrease outer membrane permeability has been seen so far only with resistance determinants of a narrow range. It would create a major health-care problem if such an activity were to become combined with broad substrate profile efflux transporters.

Increased expression of efflux transporters, often accompanied by the repression of OmpF porin synthesis, may occur without any genetic alternation. Thus, chloramphenicol and tetracycline increase the transcription of MarA regulatory protein, thereby presumably increasing the synthesis of the efflux transporter or transporters. Interestingly, oxygen stress, to which pathogenic bacteria are exposed in host tissues, is known to produce OmpF repression with increased resistance to several agents, possibly as a result of increased efflux. Similarly, salicylate, which is produced in plant tissues in response to the invasion by microorganisms, is known to repress the synthesis of PmpF porin and to make *E. coli* transiently more resistant to chloramphenicol, tetracycline, quinolones, and ampicillin. This range of agents is again suggestive of the involvement of an efflux system or systems.

Because specific mechanisms of antibiotic resistance were thought to be more important, efforts to produce more effective antibiotics have usually involved modification of specific groups on antibiotic molecules in order to make them inert as potential substrates for commonly occurring antibiotic-inactivating enzymes. The presence of the more general mechanisms of resistance forces a reevaluation of this strategy. These mechanisms produce clinically significant resistance: The intrinsic resistance to a wide variety of antibiotics seen in the important opportunistic pathogen, *P. aeruginosa*, is indeed due to a combination of a multidrug efflux transporter and an effective permeability barrier, and increased expression of the efflux transporter is the most probable cause of resistance in most of the clinical isolates from the British Isles showing increased levels of carbenicillin resistance. It will be a major challenge for the pharmaceutical industry to produce compounds that are able to overcome mechanisms of this type, because some of the multidrug efflux system seems to pump out almost any amphiphilic compound. Obviously, more information is needed about the substrate-binding process of these transporters. Another possible approach would be to increase the spontaneous influx of drugs—for example, by making the drug sufficiently lipophilic so that efflux can be counterbalanced by rapid influx. Indeed, more lipophilic derivatives of tetracycline and fluoroquinolones are more active on resistant strains of Gram-positive bacteria that pump out these agents. In Gram-negative bacteria, however, more lipophilic agents will be slower in traversing the porin channel, and increased lipophilicity may not increase the efficacy of the agents.

Siderophore-related *Pseudomonas aeruginosa*
Efflux Pump

As was discussed above, a multi-drug efflux pump is present in *P. aeruginosa*. This bacterium is a clinically significant pathogen exhibiting intrinsic resistance to a number of antibacterial agents. Moreover, problems with the development of resistance to agents generally exhibiting potent antibacterial activity against this organism (e.g., carbepenems and fluoroquinolones) are encountered with increasing frequency. In addition, cross-resistance to chemically unrelated antibiotics can be associated with fluoroquinolone resistance. In vitro studies of fluoroquinolone-resistant strains exhibiting cross-resistance have indicated that resistance is attributable to decreased drug accumulation resulting from alterations in outer membrane permeability. In some instances, this conclusion stems from the identification of novel outer membrane proteins in these mutants.

The production of a 50-kDa outer membrane protein in *P. aeruginosa* K385 was associated with decreased susceptibility to 2,2'-dipyridyl as well as to a number of antimicrobial agents. (K385 is a siderophore-deficient mutant of *P. aeruginosa* capable of growth on iron-deficient minimal medium containing 2,2'-dipyridyl (0.5 mM).) (Poole et al., 1993a.) The previously described norfloxacin-resistant *P. aeruginosa* nfxB and nfxC strains also showed decreased susceptibility to several antimicrobial agents concomitant with the production of 54- and 50-kDa outer membrane proteins, respectively. Unlike the nfxC mutants, however, K385 and the nfxB mutants did not show a decrease in the level of OprD. A ciprofloxacin-resistant mutant of *P. aeruginosa* exhibiting cross-resistance to non-quinolone antibiotics also expressed a novel outer membrane protein of 54 kDa. Finally, an outer membrane protein estimated at 49 kDa (OprM) was identified in multiple antibiotic resistance mutants of *P. aeruginosa* selected by meropenem or a combination of lomefloxacin or ofloxacin and cefsulodin. Despite some subtle differences in the resistance phenotypes of the aforementioned mutants, the outer membrane protein identified in all cases may be the same. If so, it is likely that decreased drug accumulation leading to resistance in the nfxB, nfxC, OprM-producing, and ciprofloxacin-resistant mutants was due not to altered outer membrane permeability, as originally suggested, but to antibiotic efflux, given the homology between OprM (i.e., the ORFC product) and several bacterial outer membrane efflux proteins. Interestingly, quinolone resistance and multiple antibiotic resistance in *E. coli* have also been attributed, in part, to an efflux mechanism.

In addition to OprM, the ORFA-ORFB-oprM (ORFC) operon encodes two proteins, of 40 and 108 kDa, predicted to occur in the cytoplasmic membrane. In light of the homology between the ORFAB products and cytoplasmic membrane efflux proteins, it seems likely that the ORFAB products function, in antibiotic resistance, in the efflux of antimicrobial agents across the cytoplasmic membrane. For this reason, ORFAB is designated mexAB (multiple efflux).

The ORFABC (mexA-mexB-oprM) operon is regulated by iron and indeed, OprM was inducible under certain conditions of iron limitation. The failure to observe induction of the protein during growth in iron-deficient BM2 minimal medium is probably attributable to substantial iron contamination of the phosphate component of BM2, rendering the medium less iron deficient than other minimal media. This suggests that substantial OprM (and therefore ORFABC [mexA-mexB-oprM)] expression requires more severe iron limitation. OprM was, for example, readily induced during growth in an iron-deficient HEPES-buffered minimal medium, which may be contaminated to a lesser extent with iron. Certainly, siderophore yields are three-to fourfold higher in this medium than in iron-deficient BM2 minimal medium, consistent with a lower iron content. Similarly, growth in the presence of the iron chelator 2,2'-dipyridyl, which would be expected to reduce available iron, resulted in the induction of OprM. The observed induction of OprM by $Zn^{2+}$ is also consistent with iron regulation of this protein, since $Zn^{2+}$ is known to enhance the expression of iron-regulated constituents in *P. aeruginosa*, including siderophores and their receptors. A similar effect of $Zn^{2+}$ on siderophore production has been noted for *Pseudomonas fluorescens* and *Azotobacter vinelandii*. In the latter instance, $Zn^{2+}$-enhanced siderophore production was attributable to a reduction in cytoplasmic ferrous iron levels resulting from the inhibition of ferric reductase activity by $Zn^{2+}$.

In addition to the iron regulation of ORFABC (mexA-mexB-oprM), this operon is also co-regulated with components of pyoverdine production and uptake, and it is suggested that it functions in pyoverdine secretion. The observed homology between the ORFABC (mexA-mexB-oprM) products and a number of bacterial export proteins is certainly consistent with such a conclusion. Moreover, while antibiotics purported to be substrates of an ORFABC (mexA-mexB-oprM) efflux system are structurally quite distinct, they do retain some common features (an aromatic ring), and most exhibit an ability to bind cations, including iron. In this regard, they resemble the catechol-containing chromophore of pyoverdine. This suggests, then, that ORFABC (mexA-mexB-oprM)-dependant drug resistance results from similarities between certain antimicrobial agent and pyoverdine, which may be the true substrate for the ORFABC (mexA-mexB-oprM) efflux system. Obviously, the ORFABC (mexA-mexB-oprM) products exhibit a very broad substrate specificity, and it may be that not only pyoverdine but also metabolites thereof are the natural substrates for this efflux system. Thus, ORFABC (mexA-mexB-oprM) may function not only in de novo pyoverdine secretion, but also in the secretion of recycled pyoverdine and metabolites resulting from that process.

Precedence for broad substrate specificity in components of iron transport can be found in studies of the *E. coli* iron-regulated outer membrane proteins Fiu and Cir, reportedly involved in the uptake of hydrolytic product of the siderophore enterobactin. These proteins also facilitate the uptake of antibiotics containing iron-chelating moieties, including catechol-substituted β-lactams.

The strikingly high degree of homology between the ORFAB (mexABC) products and proteins AcrA and AcrB is a strong indication of a common function. While AcrA and AcrB are putative efflux proteins involved in resistance to acriflavine and other antimicrobial agents, it is unlikely that acriflavine is the normal cellular substrate for these proteins. It is interesting to note, however, that like pyoverdine, the *E. coli* siderophore enterobactin is a catechol-containing molecule. Thus, AcrA and AcrB may function in the secretion of enterobactin and/or its metabolites. The previously identified homology between the ORFAB (mexAB) products and EnvCD (which is also highly homologous to AcrAB) suggests that *E. coli* may possess multiple systems for enterobactin export.

β-lactam-related *Pseudomonas aeruginosa* Efflux Pump

In addition to the mexAB-oprM pump discussed above, another *P. aeruginosa* efflux pump is involved in resistance to β-lactams. Active efflux, as an important factor in β-lactam resistance, is surprising since the site of action for β-lactams is on the outer surface of the cytoplasmic membrane and the β-lactams therefore do not need to enter the cytoplasm to exert their effect. In addition, the presence of carboxyl groups on many β-lactams means that they cannot rapidly diffuse across the cytoplasmic membrane. However, the resistance is shown not to be due to reduced permeability of the outer membrane or to changes in the level of β-lactamases (Li et al., 1994, *Antimicrob. Agents Chemother.* 38:1742–1752).

Experiments showed that in highly resistant *Pseudomonas aeruginosa*, two proteins which were cytoplasmic membrane proteins were highly expressed, along with one outer membrane protein. The level of expression of these proteins was significantly higher than in a related strain which was not highly resistant. In addition, it was shown that a hyper-susceptible mutant strain, k799/61, appeared to lack an active efflux system, since it was essentially incapable of pumping out tetracycline and chloramphenicol. This implies that the three overproduced proteins in the highly resistant strain are components of an efflux pump system in *Pseudomonas aeruginosa*. Typical materials and methods for this work are described in Li et al., *Antimicrob. Agents Chemother.* 38:1732–1741 (1994) and Li et al., *Antimicrob. Agents Chemother.* 38:1742–1752 (1994). The whole of these references is hereby incorporated by reference.

The amino acid sequence of these proteins can be readily determined by techniques well known to those skilled in the art. For example, each of the proteins can be isolated and purified from the identified strain which produces this efflux pump at a high level. The amino acid sequence of each of these purified proteins can then be determined using standard amino acid sequencing techniques. The nucleotide sequence coding for each of these proteins can likewise be readily determined by any of a number of different techniques. In one approach, the amino acid sequence of a portion of a protein can be converted into a degenerate set of oligonucleotide probes (preferably using a sequence with low coding degeneracy), each of which would have approximately eight to twenty nucleotides. Such a degenerate set of probes is then used to probe for the full coding sequence for that polypeptide. Once so identified, the coding sequence can be manipulated by normal recombinant techniques and can be sequenced to verify its identity as a gene for a given polypeptide. In another approach, the coding sequence corresponding to an efflux component missing or defective in an efflux pump deficient strain can be identified and again isolated and sequenced. While these approaches are exemplary, other approaches can also be used effectively and may be preferable in specific situations.

Efflux Pump Essential Gene

Efflux pumps can be essential for *P. aeruginosa* cells. There is already good circumstantial evidence that the inhibition of the cytoplasmic component of the pump could be lethal to the cell. The only way to raise null mexB mutants is to use strains that are deficient in pyoverdin production or strains that cannot grow in iron deficient medium and have impaired iron metabolism. (Poole et al., 1993, *Mol. Microbiol.* 10: 529–544.) If mexB mutants are, in fact, lethal, an inhibitor of the cytoplasmic component of the efflux pump could be bactericidal

Inhibition of Efflux Pumps

The invention shows that the existence of efflux pumps in pathogenic bacteria, especially multi-substrate efflux pumps, can be used in methods of screening compounds to find efflux pump inhibitors. As the term suggests, and as described in the Summary, such inhibitors reduce the ability of an efflux pump to export antibacterial agents from the cytoplasm. The invention shows that such screening methods can be designed for bacteria with multi-drug efflux pumps, and in particular for *Pseudomonas aeruginosa* efflux pumps, such as the mexA/mexB/opr and the pumps overexpressed in strains K385 and PAO4098E.

One method is based on the ability of an efflux pump inhibitor to slow the export of antibacterial agents from a bacterial cell. When bacteria containing an efflux pump are grown in the presence of an antibacterial agent which the efflux pump can export, but which is at too low a concentration to significantly inhibit cell growth, the efflux pump maintains the intracellular concentration of the agent at a very low concentration. However, when an efflux pump inhibitor is also present at a concentration high enough to significantly inhibit the activity of that efflux pump, it allows the intracellular concentration of the antibacterial agent to rise. The resulting elevated concentration of the antibacterial agent can then inhibit cell growth. The ability of the antibacterial agent to inhibit growth can be demonstrated by using two related bacterial strains, one of which produces the efflux pump of a high level while the other does not. Thus, the concentration of antibacterial agent used should be set high enough to inhibit the growth of the strain which does not produce the efflux pump of high level, but low enough so that growth of the strain which produces the efflux pump at a high level is not significantly inhibited. Then, compounds which inhibit the growth of the high level efflux pump strain are identified as putative efflux inhibitors. That the growth inhibition is due to efflux pump inhibition can be further indicated by comparing the growth of the same strain in the presence of the putative efflux pump inhibitor, but without the antibacterial agent. If the growth in the presence of both the putative inhibitor and the antibacterial agent is significantly less than the growth in the presence of the putative inhibitor only, then the growth inhibition is probably due to efflux pump inhibition, at least in significant part. In certain embodiments of this screen, it is useful if a microbial strain is used which overproduces the efflux pump. Then the subinhibitory concentration of antibacterial agent should be high enough to inhibit the growth of a wild-type strain of that bacterium.

Another method to screen for inhibitors of broad substrate efflux pumps, such as in *Pseudomonas aeruginosa*, is based on the use of a reporter gene whose expression is controlled by a regulatory sequence inducible by an adequately high concentration of a compound, such as an antibacterial agent (or an inactive analog). In this method the reporter gene, with the inducible regulatory sequence, is inserted as a single copy in a non-essential gene in the bacterial chromosome. Thus, when a bacterium containing the reporter gene construct insert is grown in the presence of a compound which is an efflux pump inhibitor and an antibacterial agent (which is at a concentration which would not significantly inhibit growth in the absence of some additional factor) the intracellular concentration of the antibacterial agent will rise. The rise in the intracellular concentration of the antibacterial agent is due to the reduction of the export rate, as described in the method above. However, before the antibacterial agent can reach a growth inhibitory intracellular concentration, the increasing concentration induces the expression of the reporter gene. Detection of that expression thus implies that the action of the efflux pump has been inhibited, i.e., that a compound being screened is an efflux pump inhibitor.

One design for this method uses the well-known regulatory mechanism in which expression of a reporter gene is induced by the presence of tetracycline. In this mechanism, tetracycline binds strongly to the tetR repressor molecule, preventing the binding of tetR to the operator sites of tetA. Without tetR bound to the tetA operator sites, the reporter gene coding sequence downstream of that operator is transcribed and the subsequent translation produces detected. (Kirsch et al. *J. Antibiotics* 44:210–217 (1991)). As described above, a construct containing the tetR gene, the tetA regulatory sequence, and the coding sequence of a reporter gene is inserted in a non-essential gene in *Pseudomonas aeruginosa*. These recombinant cells can then be used to screen compounds for efflux pump inhibitor activity as described above.

The method above is in contrast to the work described by Rothstein et al., *Antimicrob. Agents Chemother.* 37:1624–1629. That report described a screen for inhibitors of a tetracycline-specific pump in *E. coli* with the tetR gene on a plasmid, in conjunction with a technique for identifying new tetracyclines.

A third screen uses positive growth as the report of efflux pump inhibition. This screen is based on the induction of an inactivator of an antibiotic in response to the inhibition of an efflux pump which. Thus the microbe is grown in the presence of an inhibitory concentration of an antibiotic. An inactivator of that antibiotic is inducible by an elevated intracellular concentration of a compound exported by an efflux pump. If the efflux pump exporting that compound is inhibited (such as by a test compound) the inactivator will be expressed (or activated), reducing the intracellular concentration of the previously inhibiting antibiotic. This results in detectable growth.

One embodiment of this screen uses a tetracycline-sensitive tetA promoter as in the second screen above. However, that promoter is linked with a gene that allows growth only when the tetA promoter is induced. An example of such a gene is the blaS gene, which encodes the L-1 β-lactamase of *Stenotrophomonas maltophilia* (*Xanthomonas maltophilia*). The product of this gene can provide the positive selection required for this screen. This fusion will be placed into the chromosome, to provide genetic stability. The L-1 β-lactamase is fully functional when introduced in *P. aeruginosa*, and carbapenems are not secreted by the efflux pumps of *P. aeruginosa*. Chromosomal β-lactamases of Pseudomonas cannot hydrolyze carbapenems (J. Trias, 1989, *Antimicrob. Agents Chemother.* 33: 1201–1206).

The screening strain will be grown in the presence of low tetracycline concentration, the test compound and a carbapenem. If an efflux pump is inhibited, the intracellular concentration of tetracycline will increase, inducing the expression of the tetA promoter, and thus blaS. L-1 β-lactamase will hydrolyze the carbapenem and cells will grow. If the pumps are not inhibited, intracellular concentration of tetracycline will not rise, cells will not synthesize L-1 β-lactamase and will not grow in the presence of the carbapenem.

Screens of this type also provide the ability to titrate that requirement simply by changing the concentration of the carbapenem in the medium providing a highly flexible system to search for compounds with varying inhibition capabilities. Blocking the efflux pump should not interfere with changes in imipenem resistance because this substrate is not recognized by efflux pumps and, if the pump is inhibited, it should not make any difference.

Mechanism of Action—Regulation of the Pump

An efflux pump inhibitor could inhibit efflux pumps by inhibiting the normal function of the pump, the normal expression of the pumps, or a combination of both. To study the regulation of pumps, the presence of the pumps in the membranes will be monitored. For example it can be monitored using standard electrophoresis techniques, where the bands corresponding to the pump components can be visualized by conventional protein staining techniques (Coomassie blue or silver stain) or by standard Western analysis using antibodies against efflux pump components. The mechanism of action of the inhibitor will be further studied at the transcription level, for example by using probes obtained from the sequence of the genes coding for the components of the efflux pumps by standard Northern analysis using known sequences from the genes, or by putting a reporter gene under control of the efflux pump promoter and measuring the activity of the protein coded by the reporter gene.

Description of Compound Screening Sources and Sub-structure Search Method

The methods of this invention are suitable and useful for screening a variety of sources for possible activity as efflux pump inhibitors. Initial screens have been performed using a diverse library of compounds, but the methods are also suitable for other compound libraries. Such libraries can be natural product libraries, combinatorial libraries, or other small molecule libraries. In addition, compounds from commercial sources can be tested, this testing is particularly appropriate for commercially available analogs of identified efflux pump inhibitors.

Compounds with identified structures from commercial sources can be efficiently screened for efflux pump activity by first restricting the compounds to be screened to those with preferred structural characteristics. As an example, an effort was initiated to generate a sub-library for screening which would be enhanced in structures capable of inhibiting efflux pumps. The strategy for this effort consisted of obtaining commercially available compounds containing structural features commonly found in inhibitors of mammalian efflux pumps. In order to expedite this effort, the ISIS computer program (MDL Information Systems, Inc.) was used to perform a 2D-substructure search of the Available Chemicals Directory database (MDL Information Systems, Inc.). This database contains structural and ordering information on approximately 175,000 commercially available chemical compounds. Other publicly accessible chemical databases may similarly be used.

Generic Description of a Hit Compound

An example compound identified as an efflux pump inhibitor using the screening methods of this invention is L-phenylalanyl-L-arginyl-β-naphthylamide. Some in vitro characterization of this compound is described in Example 7 below.

This compound can be regarded as having a generic structure represented by Structures 1–4 below:

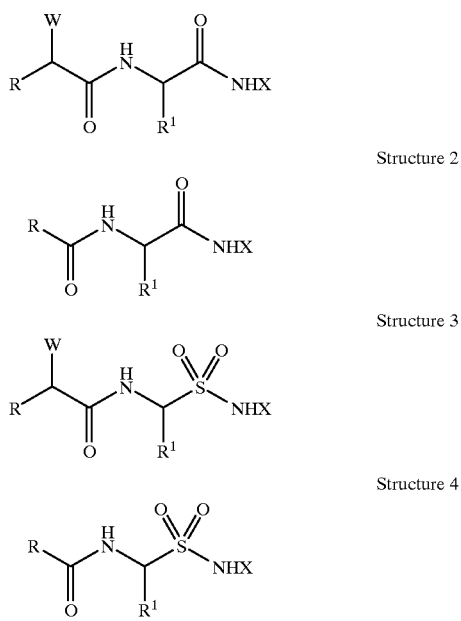

Structure 1

Structure 2

Structure 3

Structure 4 wherein

R=alkyl ($C_1$–$C_4$), fluoroalkyl ($C_1$–$C_4$), perfluoroalkyl ($C_1$–$C_4$), alkoxy ($C_1$–$C_4$), alkylthio ($C_1$–$C_4$), halogen (Br, Cl, F or I), aryl ($C_6$–$C_{10}$), monosubstituted aryl ($C_6$–$C_{10}$) [optionally substituted with alkyl ($C_1$–$C_4$), alkoxy ($C_1$–$C_4$), alkylthio ($C_1$–$C_4$), halogen (Br, Cl, F or I), amino, monosubstituted amino [optionally substituted with alkyl ($C_1$–$C_4$)], disubstituted amino [optionally substituted with any combination of alkyl ($C_1$–$C_4$)], or hydroxyl]], disubstituted aryl ($C_6$–$C_{10}$) [any combination of alkyl ($C_1$–$C_4$), alkoxy ($C_1$–$C_4$), alkylthio ($C_1$–$C_4$), halogen (Br, Cl, F or I) and amino], 2-(or 3-)-thienyl, 2-(or 3-)-furanyl, or 2-(3- or 4-)-pyridyl, W=H, $NH_2$, monosubstituted amino [optionally substituted with alkyl ($C_1$–$C_4$)], disubstituted amino [optionally substituted with any combination of alkyl ($C_1$–$C_4$)], azaheterocycles [such as N-morpholinyl, N-piperazinyl, N-pyrrolidinyl, N-imidazolyl, N-pyrrolyl, N-pyrazolyl, N-triazolyl, or N-tetrazolyl], halogen (Br, Cl, F, I), hydroxyl, alkoxy ($C_1$–$C_4$), alkylthio ($C_1$–$C_4$), $R^1$=$(CH_2)_n NR^b R^c$, $(CH_2)_n NHC$=$(NR^a)NR^b R^c$, $(CH_2)_n SNHC$=$(NR^a)NR^b R^c$, $(CH_2)_n C$=$(NR^a)NR^b R^c$, $(CH_2)_n N$=$CNR^b R^c$, (n=2–4); $R^a$ ($R^b$ or $R^c$)=H, alkyl ($C_1$–$C_4$), aryl ($C_6$), substituted aryl, benzyl, substituted benzy [optionally substituted with alkyl ($C_1$–$C_4$), alkoxy ($C_1$–$C_4$), alkylthio ($C_1$–$C_4$), halogen (Br, Cl, F or I), or amino], or alternatively $R^a$+$R^b$=$(CH_2)_{2-3}$ or —CH=CH—, X=aryl ($C_6$–$C_{10}$), —$(CH_2)_{0-2}$aryl ($C_6$–$C_{10}$), substituted aryl ($C_6$–$C_{10}$) [optionally substituted with alkyl ($C_1$–$C_4$), alkoxy ($C_1$–$C_4$), alkylthio ($C_1$–$C_4$), halogen (Br, Cl, F or I), or amino], substituted —$(CH_2)_{0-2}$aryl ($C_6$–$C_{10}$) [substitution on aryl unit with alkyl ($C_1$–$C_4$), alkoxy ($C_1$–$C_4$), alkylthio ($C_1$–$C_4$), halogen (Br, Cl, F or I), or amino], 2-(or 3-)-thienyl, 2-(or 3-)-furyl, 2-(3- or 4-)-pyridyl, benzofuranyl [at any position on the benzofuran ring], benzothienyl [at any position on the benzothiophene ring].

Where there are centers of asymmetry, the absolute stereochemistry can be either R or S configuration, or there can be a racemic mixture, all within the generic structural description.

While L-phenylalanyl-L-arginyl-β-naphthylamide is an efflux pump inhibitor, it is desirable to attempt to find related compounds with enhanced physiological profiles and efflux-inhibitory activity. In general, the usual approach to identifying related compounds with better medicinal characteristics is to prepare or obtain a number of analogs of the initial compound which each have a defined structural difference from each other. These analogs are then tested to determine whether they retain activity, and characterized with respect to factors such as resistance to degradation, serum binding, gross toxicity, and solubility. Based on the results of such analyses, a preliminary structure activity relationship (SAR) can be determined relating specific structural features or substituents with the level of activity and other factors relevant to the intended use (e.g., as a therapeutic compound). This information can then be used to direct further preparation and testing of analogs to find a compound with an improved combination of characteristics. For L-phenylalanyl-L-arginyl-β-naphthylamide, referring to the generic structures above, a reasonable initial approach to preparing analogs would be to prepare a set of analogs modified at W to search for compounds which are more stable in serum. Thus, as indicated above, such a set of analogs would be screened for activity and analyzed for improved medicinal characteristics.

Pharmaceutical Compositions and Modes of Administration

The particular compound that is an efflux pump inhibitor can be administered to a patient either by itself, or in combination with an antibacterial agent, or in pharmaceutical compositions where it is mixed with suitable carriers or excipient(s). A combination of an efflux pump inhibitor with an antimicrobial agent can be of at least two different types. In one, a quantity of an efflux pump inhibitor is combined with a quantity of an antimicrobial agent in a mixture, e.g., in a solution or powder mixture. In such mixtures, the relative quantities of the inhibitor and the antimicrobial agent may be varied as appropriate for the specific combination and expected treatment. In a second type of combination an inhibitor and an antimicrobial agent can be covalently linked in such manner that the linked molecule can be cleaved within the cell. However, the term "in combination" can also refer to other possibilities, including serial administration of an inhibitor and another antimicrobial agent. In addition, an efflux pump inhibitor and/or another antimicrobial agent may be administered in pro-drug forms, i.e. the compound is administered in a form which is modified within the cell to produce the functional form. In treating a patient exhibiting a disorder of interest, a therapeutically effective amount of an agent or agents such as these is administered. A therapeutically effective dose refers to that amount of the compound(s) that results in amelioration of symptoms or a prolongation of survival in a patient, and may include elimination of a microbial infection.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. It is preferable that the therapeutic serum concentration of an efflux pump inhibitor should be in the range of 0.1–100 μg/ml.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture Such information can be used to more accurately determine useful doses in humans. Levels in plasma may be measured, for example, by HPLC.

In particular preferred embodiments, the efflux inhibitor in a pharmaceutical composition has a structure as shown by the generic structures described above.

The exact formulation, route of administration and dosage can be chosen by the individual physician in view of the patient's condition. (See e.g. Fingl et al., in THE PHARMACOLOGICAL BASIS OF THERAPEUTICS, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific infection being treated, such agents may be formulated and administered systemically or locally. Techniques for formulation and administration may be found in *Remington's Pharmaceutical Sciences,* 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art, into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers including excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

EXAMPLES

Example 1

Efflux Pump Inhibitor Screen—Growth Inhibition Screen

The assay is based on the screening for molecules that will potentiate the action of an antibacterial agent. Two *P. aeruginosa* strains were used in the screen. Strain K385, a multi-drug resistant mutant isolated by K. Poole which overexpresses an efflux pump, and strain K613, a susceptible oprM::Hg mutant (Poole et al., 1993a; Poole et al., 1993b). The unknown molecule to be tested is included in the medium and the medium inoculated with strain K385. If the tested molecule inhibits the efflux pump it will potentiate the action of the antibacterial agent and will inhibit growth. Compounds are also tested in the absence of the antibacterial agent to test their intrinsic inhibitory activity.

Screen

A fresh inoculum of strain K385 was grown overnight at 35° C. in Mueller-Hinton broth and then diluted 1/50 in the same medium. After incubating for approximately 60 minutes the culture reached an OD of 0.2–0.3 at 600 nm and was diluted 1/50 in fresh Mueller-Hinton broth. Microtiter plates containing 50 µl per well of Mueller-Hinton with 20 µg/ml of test compound and 0.5 µg/ml of ciprofloxacin were inoculated with 50 µl of the diluted culture. A second set of microtiter plates containing the same volume of Mueller-Hinton broth and test compound but no ciprofloxacin were inoculated with 50 µl of the diluted culture. The starting growth conditions were in 100 µl of Mueller-Hinton broth with 10 µg/ml of test compound and 0.25 µg/ml of ciprofloxacin. Plates were placed in a 35° C. incubator and incubated for 20 hours. Growth was measured at 600 nm using a plate reader (Thermomax microplate reader, Molecular Devices). The following controls were included, uninoculated Mueller-Hinton broth, strain K385 grown in Mueller-Hinton broth with 0.25 µg/ml of ciprofloxacin and in the absence of ciprofloxacin, strain K613 grown in Mueller-Hinton broth with 0.25 µg/ml of ciprofloxacin and in the absence of ciprofloxacin. Uninoculated Mueller-Hinton broth was used to establish the base line for growth. Test compounds in the presence of ciprofloxacin were run in duplicates. The addition of 10 µg/ml of L-phenylalanyl-L-arginyl-β-naphthylamide potentiated the action of ciprofloxacin and growth was inhibited by 99% as measured OD600 and compared to the growth of strain K385 with 0.25 µg/ml of ciprofloxacin. Growth inhibition by 10 µg/ml L-phenylalanyl-L-arginyl-β-naphthylamide in the absence of ciprofloxacin was 1%.

A similar screen can be run with strain PAO4098E that overproduces an efflux pump different than the K385 one. In this screen the ciprofloxacin concentration to test for potentiators is 0.2 µg/ml instead of 0.25 µg/ml.

If a tested molecule inhibits the efflux pump, the intracellular concentration of ciprofloxacin will increase and cellular growth will be inhibited. Compounds that potentiate the action of ciprofloxacin are identified and further evaluated.

As discussed above in the Preferred Embodiments, similar screens can also be performed using other species expressing efflux pumps, and with other antibiotics which are exported by those pumps.

Example 2

Second Screen—Measuring the Intracellular Concentration of Tetracycline

A more specific screen is based on the use of tetR regulatory domain to control the expression of a reporter gene. tetR is a very well known regulatory system that senses the concentration of tetracycline, and it induces the synthesis of TetA when the concentration of tetracycline increases in the cell. If the efflux pump is blocked, the intracellular concentration of tetracycline will increase and proteins under TetR control will be induced.

tetR and the regulatory domain have been cloned and a tetA-lacZ gene fusion has been put under TetR control. The construct will be put in *P. aeruginosa* by insertion in a non-essential chromosomal gene and a screen based on the use of this strain will be set up. This construct is different from the one published by Rothstein et al., i) the gene fusion is made at a different place in teta, ii) it is not designed to find inhibitors of tetracycline-specific pumps, but rather to find inhibitors of a multi-substrate efflux pump and iii) the construct will be inserted in the chromosome instead of a plasmid.

Strain PAO1 will be used for the screen. It will contain the construct described above in a non-essential gene. PAO1 will be grown in a medium containing sub-inhibitory concentrations of tetracycline, a substrate of β-galactosidase. Compounds to be tested will be added to the medium before the inoculation of the strain or after the culture has grown. If the tested compound inhibits the efflux pump, the intracellular concentration of tetracycline will increase, and LacZ will be synthesized. The presence of LacZ will be detected by the β-galactosidase substrate.

Example 3

Third Screen—Positive Growth Screen

This assay is a positive growth screen; that is, the presence of an efflux pump inhibitor is indicated by growth of the bacterial cells. The assay utilizes a β-lactamase gene under the control of an inducible regulatory region. For this screen a construct containing the tetR gene, the teta promoter and the blaS gene is inserted in a non-essential gene in the chromosome of *Pseudomonas aeruginosa* strain PAO1. The blaS gene encodes the L-1 β-lactamase from *Xanthomonas maltophilia;* carbapenems are efficient substrates of this β-lactamase. Strain PAO1 does not produce β-lactamases which can utilize carbapenems effectively as substrates and, in addition, carbapenems are not transported by the efflux pumps of *Pseudomonas aeruginosa.* In the absence of a β-lactamase which can efficiently utilize carbapenems as substrates, the low permeability of the *Pseudomonas aeruginosa* outer membrane can be overcome by high concentration of a carbapenem, which will then inhibit growth of the bacteria. Thus, if expression of the blaS gene is not induced, the Pseudomonas cells will die due to the presence of the carbapenem. However, if, in addition, tetracycline is present in the medium at a very low concentration, and an efflux inhibitor is present at a concentration effective to inhibit an efflux pump which transports tetracycline, the intracellular concentration of tetracycline will rise, thereby inducing the expression of the blaS gene which will hydrolyze the carbapenem allowing growth of the bacteria.

This assay further allows titration of the activity of weak efflux pump inhibitors. This titration can be accomplished by utilizing various concentrations of the carbapenem in the medium. Inefficient inhibitors which do not fully induce the expression of the blaS gene will not result in positive cell growth at high carbapenem concentrations because not enough of the carbapenem will be hydrolyzed by the small amount of β-lactamase induced, while at low carbapenem concentrations there will be sufficient β-lactamase induced to hydrolyze enough of the carbapenem to allow cell growth. Thus this assay provides a method for detecting weak as well as strong efflux pump inhibitors.

Example 4

Evaluation of the Targets

To assess the influence of the efflux pump in pathogenesis, we obtained mexA and oprK coding for efflux pump components in PAO1. The strains were constructed using standard procedures of gene replacement. Null mutants of mexB were not obtained, probably because the mutation is lethal. MexA and oprK null mutants are more susceptible to antibiotics and will be used for animal model to test the virulence of the mutants in neutropenic mice.

Example 5

Evaluation of Hit Compounds

Compounds identified as efflux pump inhibitors based on screening with one or more of the above screening methods (growth inhibition, reporter induction, or positive growth screens) are tested for their ability to enhance the susceptibility of *P. aeruginosa* to unrelated antibiotics, norfloxacin and tetracycline. Subsequently, the potentiation effect of these molecules using a range of antibiotics, such as tetracycline, fluoroquinolones, β-lactams, and aminoglycosides is determined. The antibacterial activity of efflux pump inhibitors compounds will also be tested.

Further, compounds will be tested for the inhibition of other pumps (e.g., MexC-MexD-OprL system, NorA, TetA, MDR). The identified compounds will also be tested for their ability to inhibit the efflux pump at the molecular level.

Example 6

Identification of a Hit Compound—L-phenylalanyl-L-arginyl-β-naphthylamide

Figure 21:
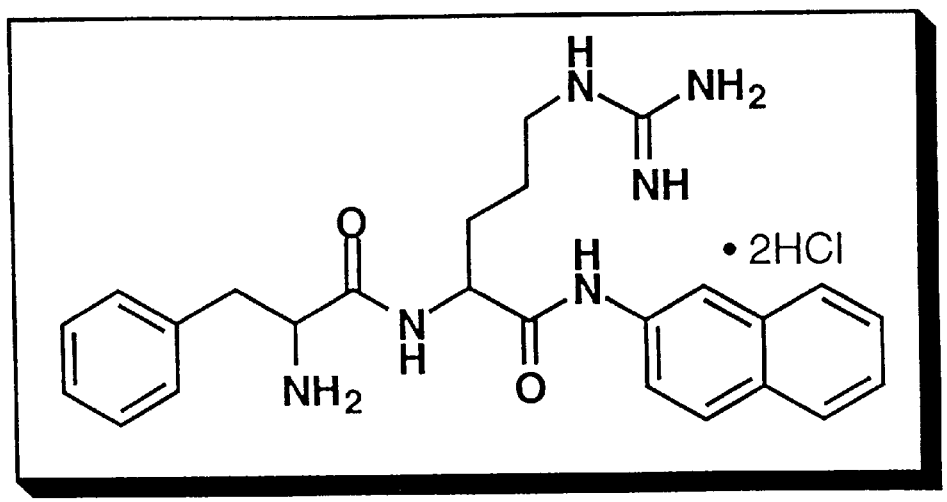
FIG. 21 provides a structural representation of L-phenylalanyl-L-arginyl-β-naphthylamide.

The compound, L-phenylalanyl-L-arginyl-β-naphthylamide, was identified as an efflux pump inhibitor using the growth inhibition screen described in Example 1. The screening was performed on a group of compounds preselected on the basis of structures and expected suitability for therapeutic use. The structure of this compound is shown in FIG. 21. Following this identification, this compound was subjected to in vitro characterization as described in Example 7.

Example 7

Characterization of Hit Compound—L-phenylalanyl-L-arginyl-β-naphthylamide

A. Use of L-phenylalanyl-L-arginyl-β-naphthylamide to identify the presence of pumps L-phenylalanyl-L-arginyl-β-naphthylamide can be used to identify the presence of pumps inhibited by this product. The identification will be based on the potentiation of antibiotics effluxed by pumps inhibited by L-phenylalanyl-L-arginyl-β-naphthylamide or by monitoring the secretion of a substrate of the pumps, for example a protein.

B. In Vitro Profile.

L-phenylalanyl-L-arginyl-β-naphthylamide increased the susceptibility of the wild type PAO1 strain of *P. aeruginosa* as well as that of two efflux pump overproducer strains K385 and PAO4098E to both tetracycline and ciprofloxacin (FIGS. 7 & 8). Using a checkerboard assay, synergism was also clearly demonstrated for these 3 strains for the combination of L-phenylalanyl-L-arginyl-β-naphthylamide and tetracycline or ciprofloxacin. L-phenylalanyl-L-arginyl-β-naphthylamide had no effect on the susceptibility to tetracycline and ciprofloxacin of the pump deficient mutant, K799/61 (FIG. 8). L-phenylalanyl-L-arginyl-β-naphthylamide also showed intrinsic antibacterial activity at elevated concentrations (32 μg/ml) and the MICs for the four strains of *P. aeruginosa* are shown in Table 2. It is important to note that both efflux pump hyperproducers were much less susceptible to L-phenylalanyl-L-arginyl-β-naphthylamide than the wild type or the pump deficient mutant (FIG. 8).

Using *P. aeruginosa* PAO1 and K385 we have shown that L-phenylalanyl-L-arginyl-β-naphthylamide also has the ability to potentiate the activity of a variety of antibiotics shown to be specifically pumped out of *P. aeruginosa* (tetracycline, chloramphenicol, piperacillin, ceftazidime and seven fluoroquinolones including ciprofloxacin and norfloxacin), however, the MIC of drugs such as imipenem, and gentamicin which are not substrates of the MDR/pyoverdin efflux pump of *P. aeruginosa* (Li et al, 1994a; Li et al , 1994b) remained unchanged in the presence of L-phenylalanyl-L-arginyl-β-naphthylamide.

Figure 9B:
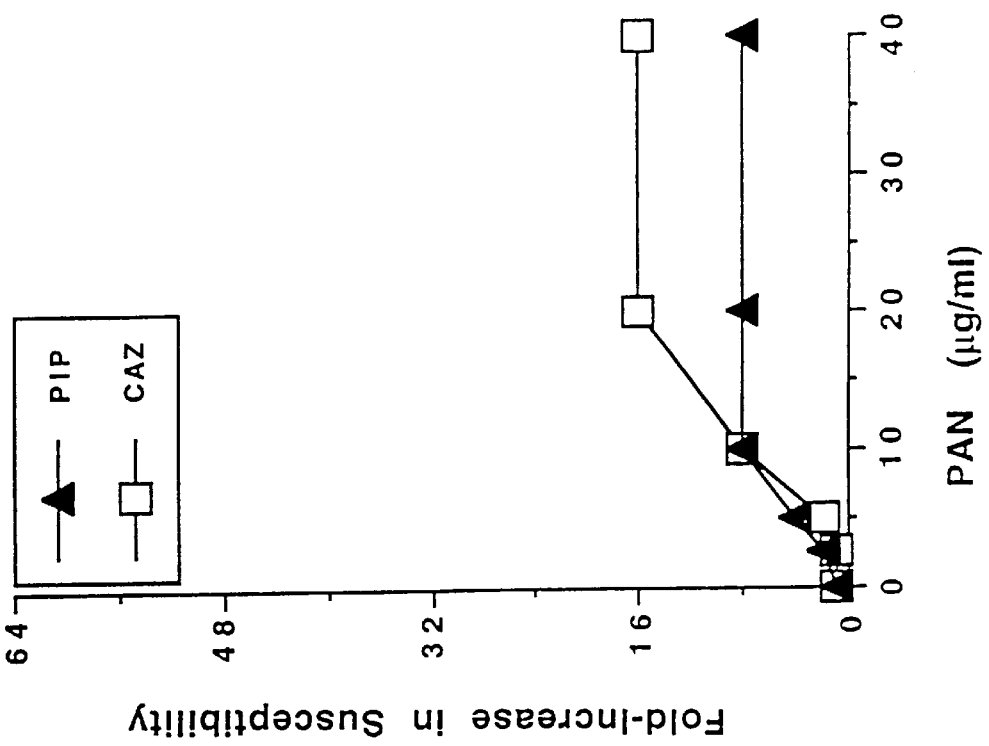
FIG. 9 graphically shows the fold increase in susceptibility of *Pseudomonas aeruginosa* PAO1 for 13 antibiotics after 24 hours at various concentrations of L-phenylalanyl-L-arginyl-β-naphthylamide.
Figure 9A:
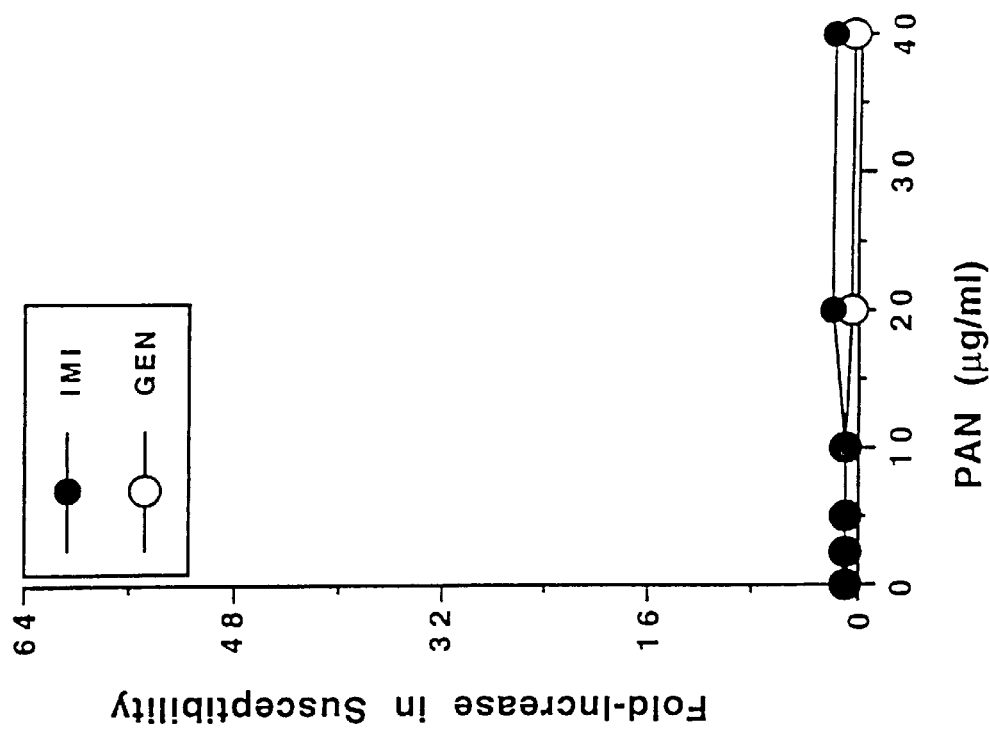

The fold-increase in susceptibility for each antibiotic tested against *P. aeruginosa* PAO1 is graphically represented in FIG. 9 and MICs are given in FIG. 10. A direct relationship was also established between the relative hydrophobicity of four amphoteric fluoroquinolones and the degree of reduction of the MIC for *P. aeruginosa* PAO1 and K385 caused by L-phenylalanyl-L-arginyl-β-naphthylamide (FIG. 11) .

Figure 12:
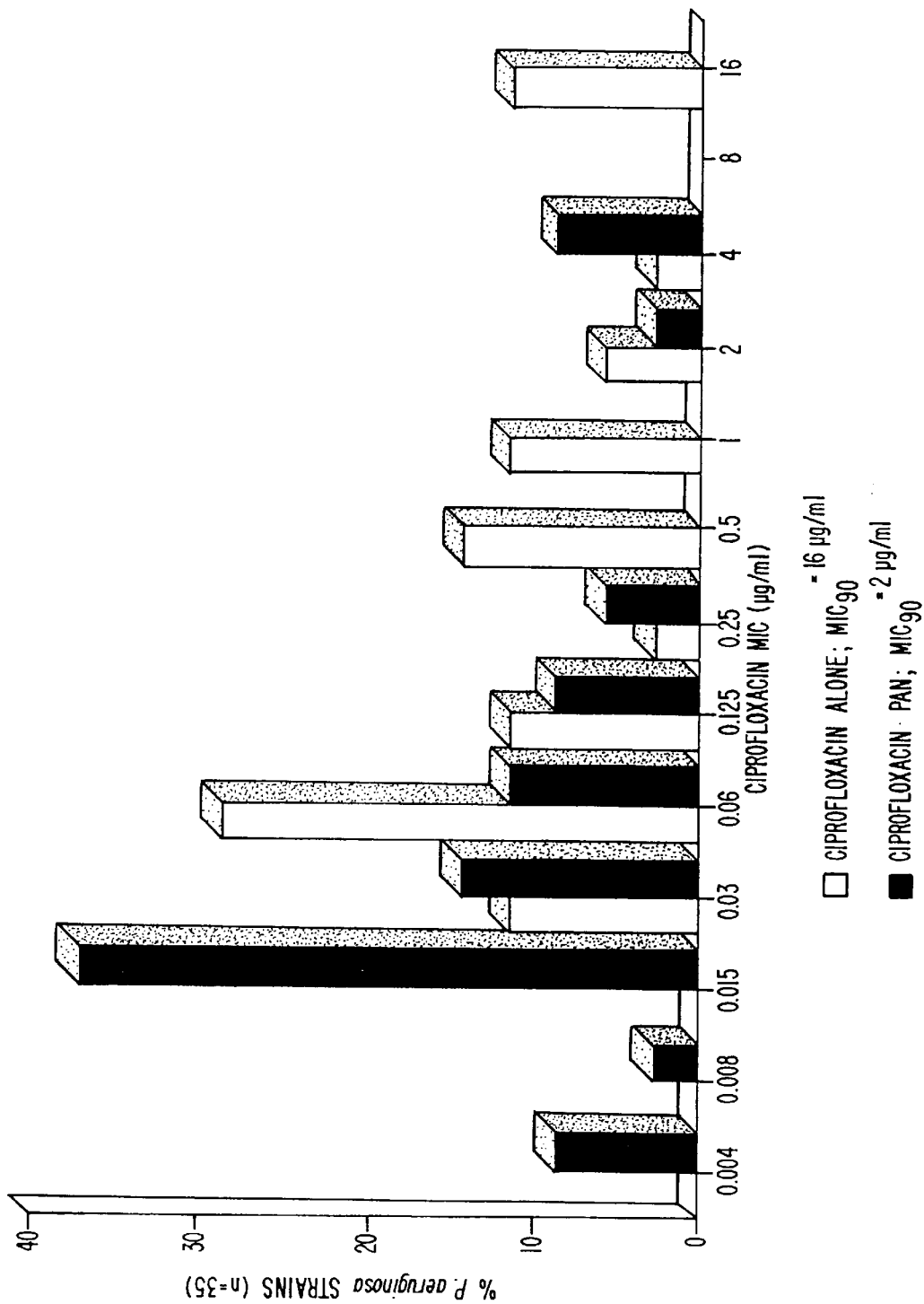
FIG. 12 shows the reduction in MIC for ciprofloxacin for 26 strains of *Pseudomonas aeruginosa*, including both clinical isolates and laboratory strains.

L-phenylalanyl-L-arginyl-β-naphthylamide reduced ciprofloxacin MICs for all laboratory strains and clinical isolates of *P. aeruginosa* so far tested (n=26). This strain population represents 18 clinical isolates and 8 laboratory strains. Using a broth microdilution method, the susceptibility of this strain population to ciprofloxacin and the combination of ciprofloxacin and L-phenylalanyl-L-arginyl-β-naphthylamide was studied. The MIC90 of ciprofloxacin for this population of strains was 2 μg/ml and addition of L-phenylalanyl-L-arginyl-β-naphthylamide, at a final concentration of 20 μg/ml, lowered it to 0.125 μg/ml (FIG. 12).

Figure 13B:
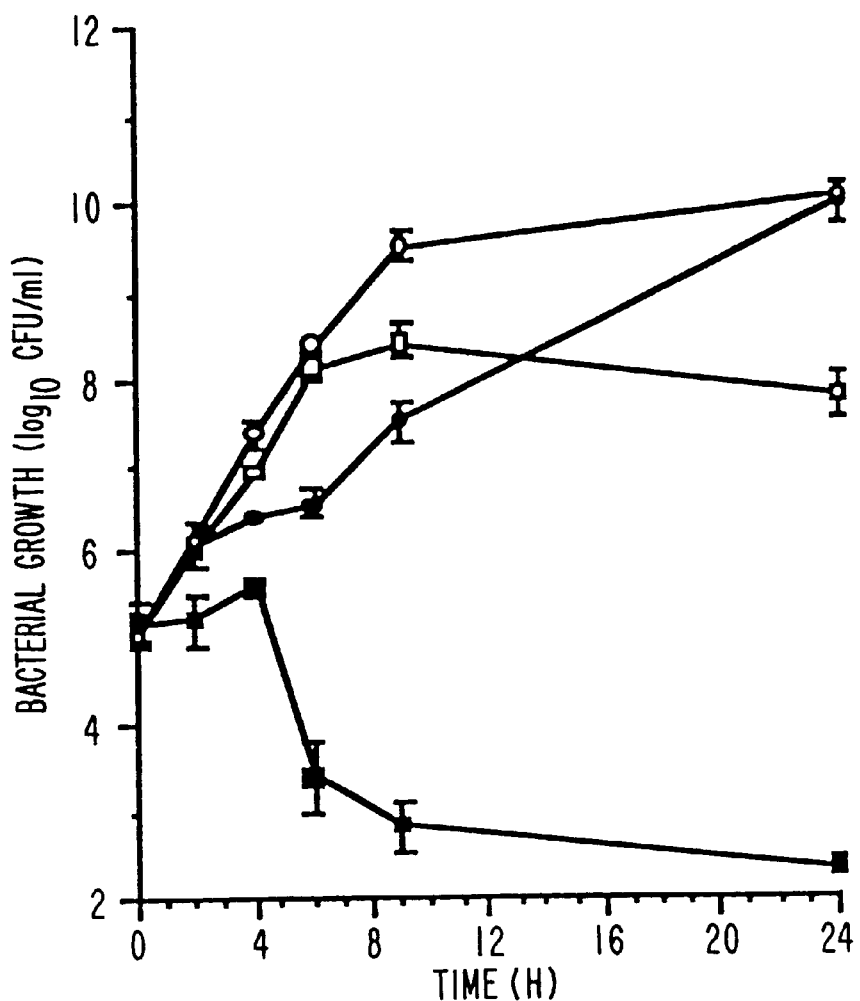
FIGS. 13–15 show the results of time-kill studies for 3 strains of *Pseudomonas aeruginosa*. Each strain was tested against tetracycline and ciprofloxacin in the presence and absence of each antibiotic, with and without L-phenylalanyl-L-arginyl-β-naphthylamide.
Figure 14A:
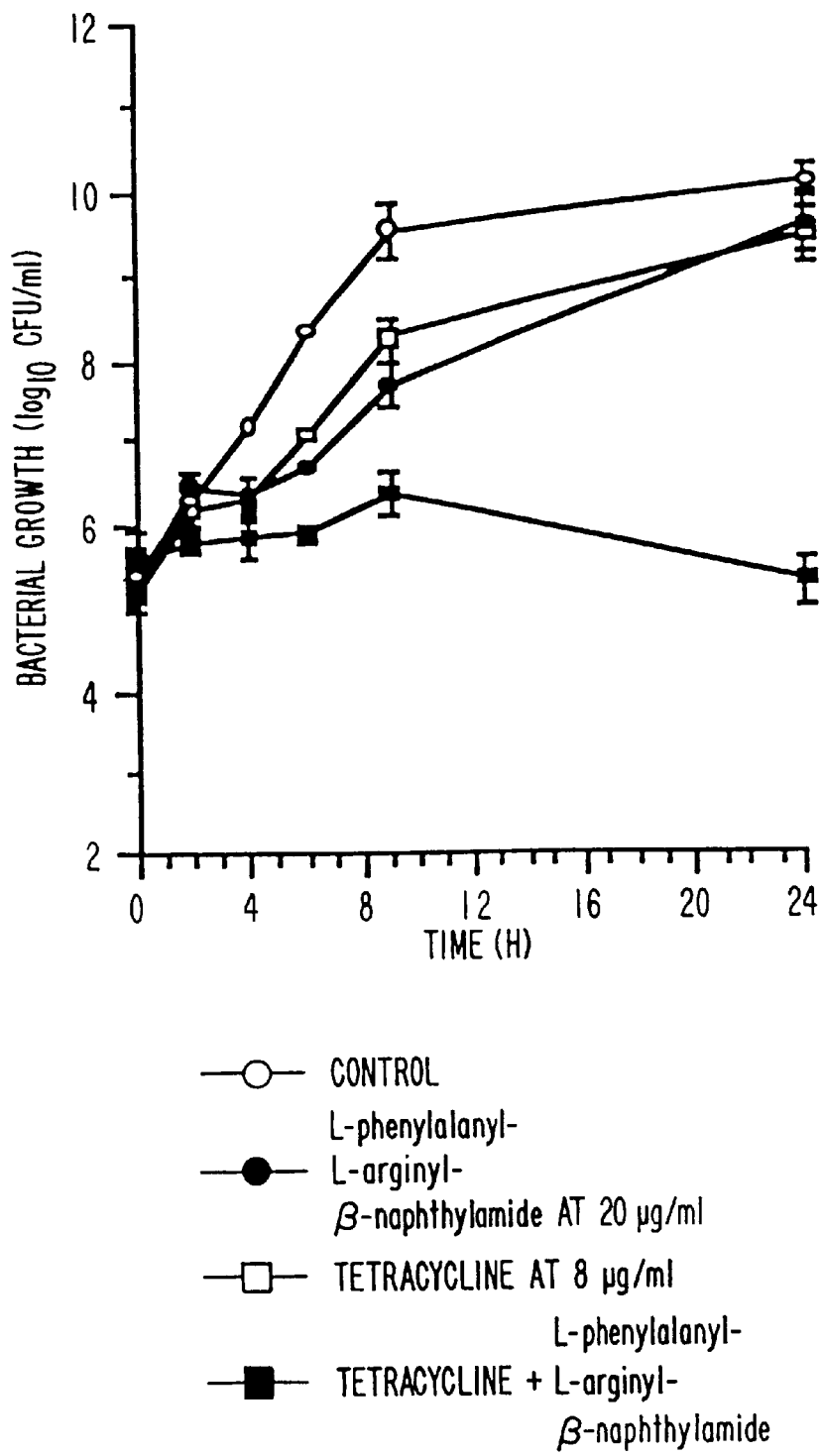
Figure 14B:
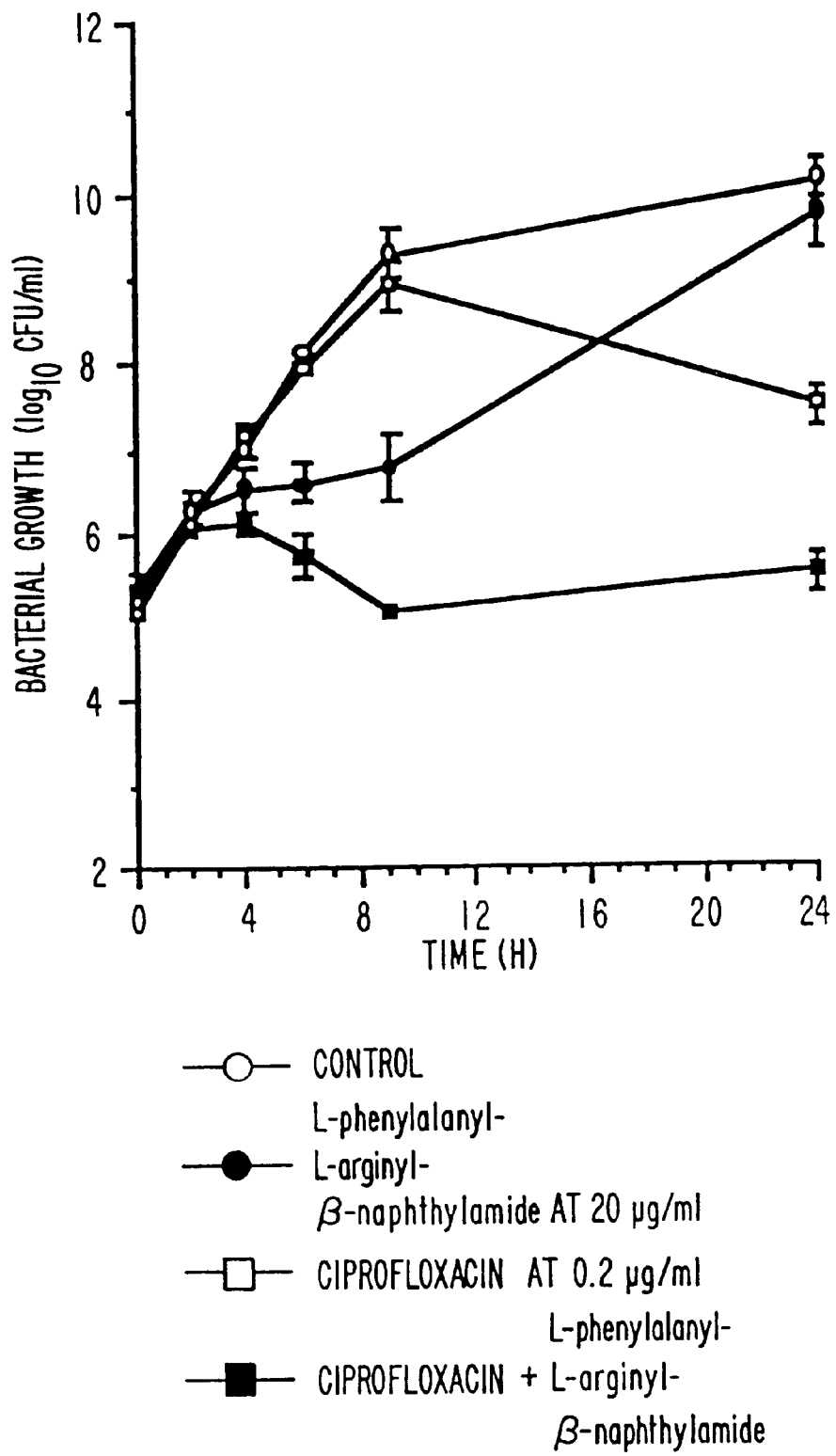
Figure 15B:
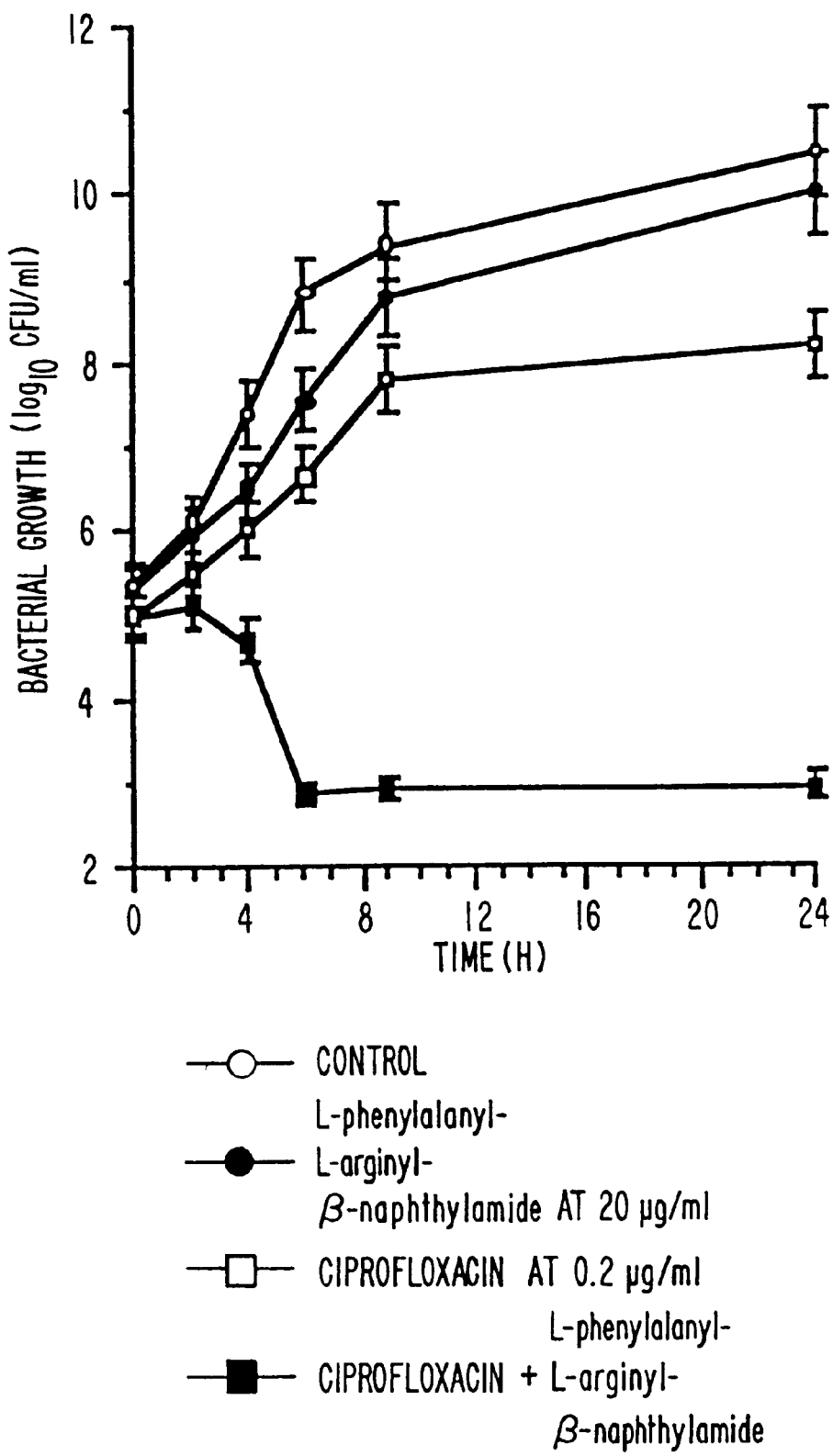

Time-kill studies with the combinations of -L-phenylalanyl-L-arginyl-β-naphthylamide and sub-inhibitory concentrations of tetracycline or ciprofloxacin were performed with three strains of P. aeruginosa, PAO1, K385 and PAO4098E. It was shown that the addition of L-phenylalanyl-L-arginyl-β-naphthylamide, at a final concentration of 20 µg/ml, restored completely the bacteriostatic activity of tetracycline against those three strains. Also, in the presence of 20 µg/ml of L-phenylalanyl-L-arginyl-β-naphthylamide a concentration as low as 0.2 µg/ml was bactericidal for all strains tested (FIGS. 13–15).

We have also shown that the susceptibility to ciprofloxacin for most enterobacteriaceae and Pseudomonas species can be augmented by L-phenylalanyl-L-arginyl-β-naphthylamide. Ciprofloxacin was potentiated by L-phenylalanyl-L-arginyl-β-naphthylamide for one clinical isolate of S. aureus and its MIC was reduced from 16 µg/ml to 4 µg/ml (FIG. 16).

Figure 17:
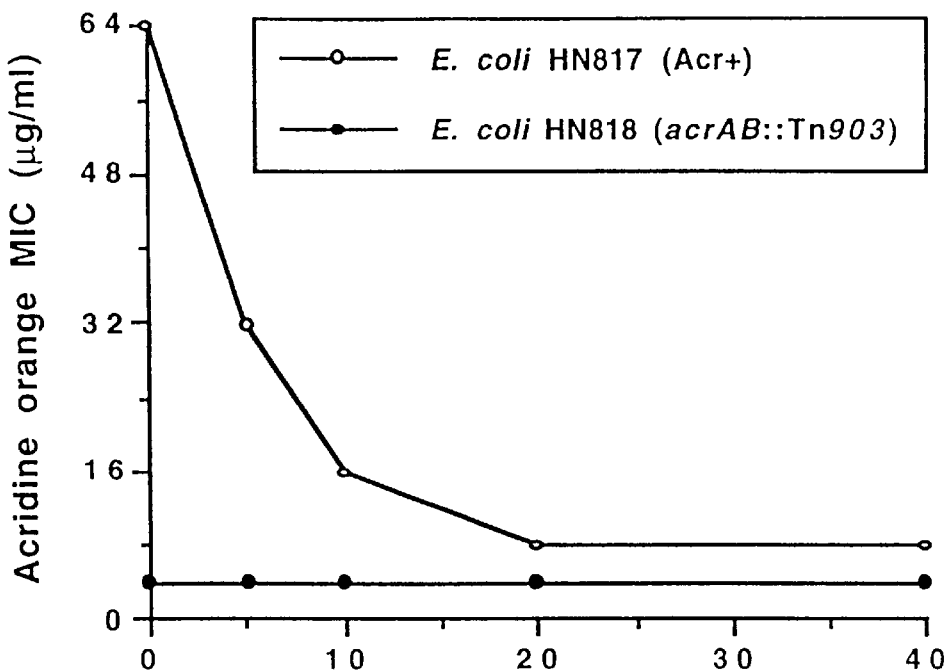
FIG. 17 shows a comparison of the effects of L-phenylalanly-L-arginyl-β-naphthylamide on the susceptibility of *E. coli* Acr+ and Acr− strains to acridine orange.

The effect of L-phenylalanyl-L-arginyl-β-naphthylamide was also studied on an AcrAB pump deficient mutant of E. coli which was obtained by transposon mutagenesis in the laboratory of H. Nikaido. We have shown that L-phenylalanyl-L-arginyl-β-naphthylamide increase the susceptibility to acridine orange of the parent strain HN817, an E. coli K12 with the Acr positive phenotype. The AcrAB pump deficient strain, HN818, was more susceptible to acridine orange than the parent strain and its level of susceptibility was not affected by L-phenylalanyl-L-arginyl-β-naphthylamide (FIG. 17).

Figure 18:
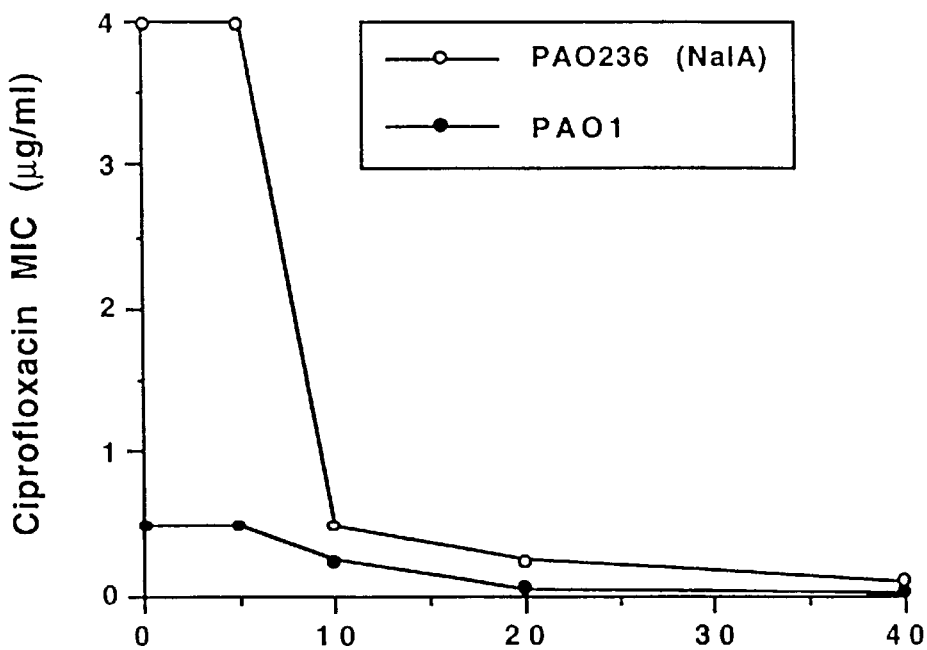
FIG. 18 shows a comparison between *P. aeruginosa* strain PAO1 and a DNA gyrase mutant strain, of the effects of L-phenylalanyl-L-arginyl-β-naphthylamide on susceptibility to ciprofloxacin.

L-phenylalanyl-L-arginyl-β-naphthylamide was shown to potentiate ciprofloxacin against a P. aeruginosa strain with a known DNA gyrase mutation (PAO236 NalA). The overall susceptibility of Gram-negative bacteria to antimicrobial agents is determined by the relative contribution of both the outer membrane permeability (including efflux) and the affinity of the target for the drug. If the efflux of quinolones is affected in a NalA strain, the apparent concentration of quinolone necessary to cause inhibition of growth will be decreased resulting in an augmentation of susceptibility to the drug (FIG. 18).

A tetracycline accumulation assay was set up to measure the activity of efflux pumps in P. aeruginosa. The assay measures the accumulation of [3H]-tetracycline in bacteria and was optimized for measuring tetracycline accumulation in P. aeruginosa. Tetracycline accumulation was measured in four different P. aeruginosa strains: 1) wild type strain PAO1 that produces basal levels of efflux pumps, 2) strains PAO4098E and K385 derived from PAO1 and overproducers of two different efflux pumps and 3) strain 799/61, a strain that does not produce measurable amounts of any efflux pumps and is hypersusceptible to antibiotics.

Figure 19A:
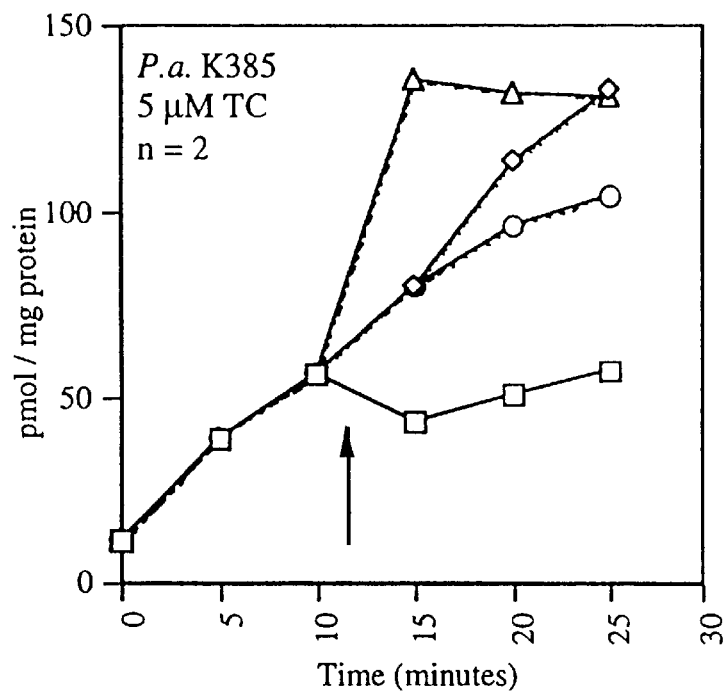
FIG. 19 shows the change in tetracycline accumulation in response to the presence of CCCP or L-phenylalanyl-L-arginyl-β-naphthylamide in three *P. aeruginosa* strains which produce efflux pumps.
Figure 19B:
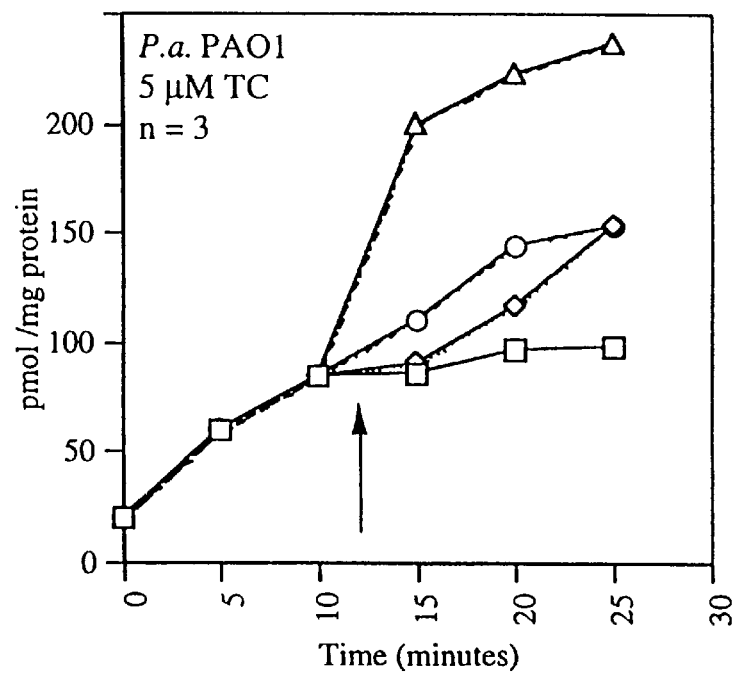
Figure 19C:
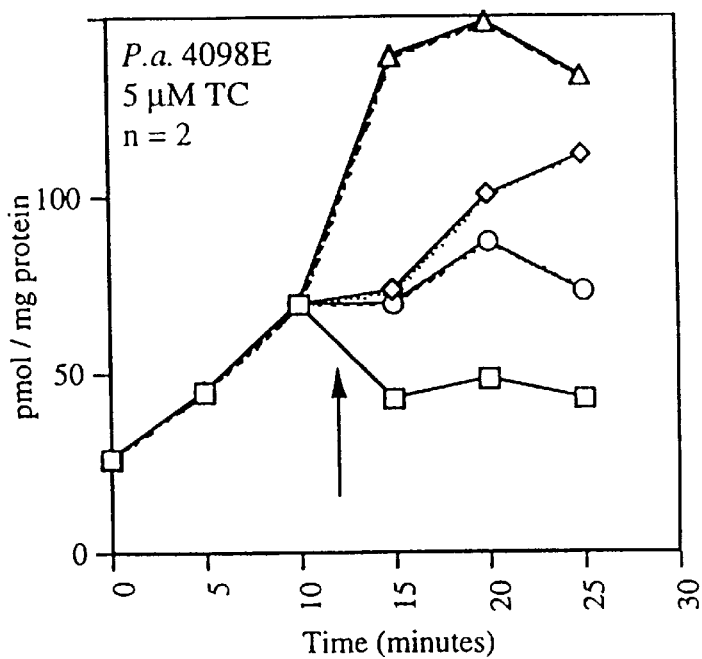

The addition of L-phenylalanyl-L-arginyl-β-naphthylamide in cell suspensions of bacteria that synthesized efflux pumps, PAO1, PAO4098E or K385, inhibited the normal function of the efflux pumps and tetracycline accumulation increased dramatically at 1 mM or 0.1 mM of L-phenylalanyl-L-arginyl-β-naphthylamide. A similar pattern of inhibition happened when CCCP, a proton conductor that destroys the proton gradient used by the efflux pumps as source energy, was added to the cell suspension (FIG. 19).

Figure 20:
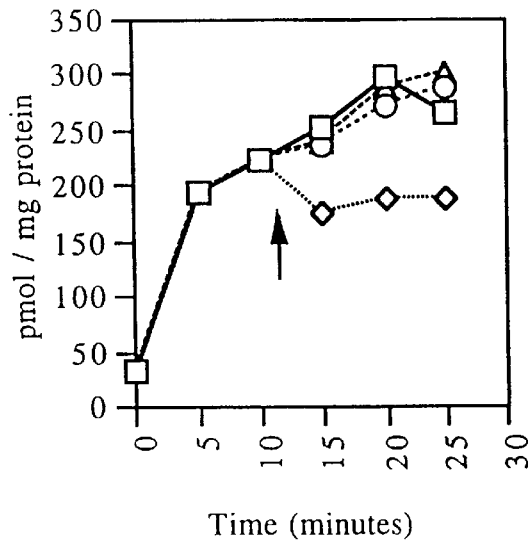
FIG. 20 shows the difference in the effects of CCCP and L-phenylalanyl-L-arginyl-β-naphthylamide on the accumulation of tetracycline in *P. aeruginosa* strain 799/61.

When tetracycline accumulation was measured in a strain that does not produce efflux pumps, strain 799/61, the addition of L-phenylalanyl-L-arginyl-β-naphthylamide did not change the steady-state level of tetracycline accumulation. The addition of the proton conductor, CCCP, lowered the tetracycline accumulation in 799/61. A new tetracycline steady state equilibrium is reached when CCCP is added to the cell suspension and pH equilibrates in both sides of the membrane. The addition of L-phenylalanyl-L-arginyl-β-naphthylamide to the cell suspension did not change the steady state level of tetracycline accumulation in the presence of CCCP, as expected for a specific inhibitor of efflux pumps that does not interfere with the proton gradient (FIG. 20).

The results clearly showed that L-phenylalanyl-L-arginyl-β-naphthylamide inhibited the function of the efflux pumps in P. aeruginosa. L-phenylalanyl-L-arginyl-β-naphthylamide did not interfere with the proton gradients and it did not behave as a proton uncoupler.

Example 8

In vivo Evaluation of Hit Compounds

Inhibitors of the bacterial efflux pumps are initially characterized in vitro. Those which show effective inhibition of the pump(s) and which show synergistic activity with antibiotics are selected for evaluation in vivo. Efficacy testing will be done using standard procedures. Primary efficacy evaluation may be done using the murine septicemia model (M. G. Bergeron, 1978, Scand. J. Infect. Dis. Suppl. 14:189–206; S. D. Davis, 1975, Antimicrob. Agents, Chemother. 8:50–53). in this model a supra-lethal dose of bacteria is used to challenge the rodents. Treatment is initiated, varying either or both time(s) of treatment and dose of antibiotic. In these experiments both the antibiotic and the efflux pump inhibitor doses are varied. A positive result is indicated by significant increase in protection from the lethal infection by the combination of the potentiator (the efflux pump inhibitor) and the antibiotic vs. the antibiotic alone.

A second efficacy model which is used is the mouse soft tissue infection model (Vogelman et al., 1988, J. Infect. Dis. 157:287–298). In this model anesthetized mice are infected with an appropriate titer of bacteria in the muscle of the hind thigh. Mice are either neutropenic (cytoxan treated at 125 mg/kg on days −4, −2, and 0) or immunocompetent. The infecting dose is commonly $10^5$–$10^6$ colony forming units per animal. Treatment with the combination of the efflux pump inhibitor and/or antibiotics follows infection, or can occur before infection. The proliferation (or death) of the bacteria within the thigh muscle is monitored over time. Effective combinations show greater activity than the antibiotic alone. Activity is defined as reduction in growth rate of the test bacteria in the murine tissue.

Another model useful for assessing the effectiveness of the efflux pump inhibitors is the diffusion chamber model (Malouin et al., 1990, Infect. Immun. 58:1247–1253; Day et al., J. Infect. 2:39–51; Kelly et al., 1989, Infect. Immun. 57:344–350). In this model rodents have a diffusion chamber surgically placed in their peritoneal cavity. The chamber can consist of a polypropylene cylinder with semipermeable membranes covering the cylinder ends. Diffusion of peritoneal fluid into and out of the chamber provides nutrients for the microbes. The proliferation of the bacteria in the presence and absence of the antibiotic/efflux pump inhibitor is compared to the antibiotic alone. Dose ranging of the combination and the antibiotic alone are done to assess effectiveness of the antimicrobial/combinations.

A tertiary model useful as a stringent test of the efflux pump inhibitor/antibiotic combination is the endocarditis model (J. Santoro and M. E. Levinson, 1978, Infect. Immun. 19:915–918). Either rats or rabbits are effectively used in this model. The effectiveness of combinations of efflux inhibitor and antibiotic are compared to antibiotic alone. The end point is usually viable cells remaining in the cardiac vegetations at the end of treatment.

The examples of infection models provided are not limiting, other models can be utilized as appropriate for a specific infecting microbe. In particular, cell-based infection models may be used in some circumstances instead of animal models.

The embodiments described herein are not meant to be limiting to the invention. Those of skill in the art will appreciate that the invention can be practiced using numerous bacterial strains and species, or other cell types.

Other embodiments are within the following claims.

What we claim is:

1. A method for screening for a non-tetracycline-specific efflux pump inhibitor, comprising determining whether a potential said non-tetracycline-specific efflux pump inhibitor inhibits the growth of a bacterium in the presence of subinhibitory concentrations of an antibacterial agent wherein said bacterium overproduces a non-tetracycline-specific efflux pump and said bacterium is grown in the presence of a said subinhibitory concentration of said antibacterial agent sufficient to inhbibit said bacterium if allowed to accumulate intracellularly; and wherein said determining comprises comparing the growth of said bacterium which overproduces said efflux pump, with the growth of a second bacterium which does not produce said efflux pump, wherein said first and second bacteria are grown in the presence of said potential non-tetracycline specific efflux pump inhibitor, and wherein said test compound is a non-tetracycline-specific efflux pump inhibitor if the growth of said bacterium which overproduces said efflux pump is inhibited to a greater degree than the growth of said second bacterium.

2. The method of claim 1, wherein said non-tetracycline-specific efflux pump is a *Pseudomonas aeruginosa*-type efflux pump.

3. The method of claim 2, wherein said efflux pump is a *Pseudomonas aeruginosa* efflux pump.

4. The method of claim 3, wherein said bacterium is *Pseudomonas aeruginosa*.

5. The method of claim 3, wherein said *Pseudomonas aeruginosa* is Strain K385 or PAO4098E.

6. The method of claim 1, wherein said bacterium is selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Acinetobacter calcoaceticus,* and *Acinetobacter haemolyticus*.

7. The method of claim 1, wherein said bacterium is selected from the group consisting of *Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Morganella morganii, Escherichia coli, Citrobacter freundii, Proteus mirabilis, Proteus vulgaris, Providencia alcalifaciens, Providencia rettgeri, Providencia stuartii, Aeromonas hydrophilia, Francisella tularensis, Yersinia enterocolitica, Yersinia pestis, Yersinia pseudotuberculosis,* and *Yersinia intermedia*.

8. The method of claim 1, wherein said bacterium is selected from the group consisting of *Bordetella pertussis, Bordetella parapertussis, Bordetella bronchiseptica. Neisseria gonorrhoeae, Neisseria meningitidis,* and *Moraxella Branhamella catarrhalis. Haemophilus influenzae, Haemophilus parainfluenzae, Haemophilus haemolyticus, Haemophilus parahaemolyticus, Haemophilus decreyi, Pasteurella multocida, Pasteurella haemolytica, Neisseria gonorrhoeae, Neisseria meningitidis,* and *Moraxella* (Branhamela) *catarrhalis*.

9. The method of claim 1, wherein said bacterium is selected from the group consisting of *Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes,* and *Gardnerella vaginalis*.

10. The method of claim 1, wherein said bacterium is selected from the group consisting of *Bacteroides fragilis, Bacteroides distasonis,* Bacteroides 3452A homology group, *Bacteroides vulgatus, Bacteroides ovalus, Bacteroides thetaiotaomicron, Bacteroides uniformis, Bacteroides eggerthii, Bacteroides splanchnicus,* and *Clostridium difficile*.

11. The method of claim 1, wherein said bacterium is selected from the Igroup consisting of *Mycobacterium tuberculosis, Mycobacterium avium, Mycobacterium intracellulare, Mycobacterium leprae, Corynebacterium diphtheriae,* and *Corynebacterium ulcerans*.

12. The method of claim 1, wherein said bacterium is selected from the group consisting of *Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis, Staphylococcus saccharolyticus*.

13. A method for screening for a non-tetracycline-specific efflux pump inhibitor, comprising determining whether the intracellular concentration of a second compound, in a recombinant bacterium expressing a non-tetracycline-specific efflux pump, is elevated in the presence of a test compound and a subinhibitory concentration of said second compound, wherein said determining comprises detecting the expression of a reporter gene controlled by a regulatory sequence inducible by an elevated concentration of said second compound, and wherein said test compound is a non-tetracycline specific efflux pump inhibitor if the level of expression of the reporter gene is higher in the presence of said test compound than in its absence.

14. The method of claim 13, wherein said second compound is an antibacterial agent.

15. The method of claim 14, wherein said regulatory sequence is inducible by an elevated concentration of tetracycline.

16. The method of claim 15, wherein said regulatory sequence is a tetA regulatory sequence, which contains an operator site which binds TetR.

17. The method of claim 13, wherein said non-tetracycline-specific efflux pump is a *Pseudomonas aeruginosa*-type efflux pump.

18. The method of claim 17, wherein said efflux pump is a *Pseudomonas aeruginosa* efflux pump.

19. The method of claim 18, wherein said recombinant bacterium is derived from *Pseudomonas aeruginosa* Strain PAO1, strain K385 or strain PAO4098E.

20. The method of claim 13, wherein said bacterium is selected from the group consisting of *Pseudomonas* aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus subsp. hyicus, Staphylococcus haemolyticus, Staphylococcus hominis, Staphylococcus saccharolyticus.

21. The method of claim 13 or 18, wherein said reporter gene expresses an enzyme.

22. The method of claim 21, wherein said reporter gene is a β-galactosidase gene.

23. The method of claim 21, wherein said reporter gene provides a colorimetric report.

24. The method of claim 3 or 18, wherein the efflux pump is selected from the group consisting of mexA/mexB/oprM and the efflux pump overexpressed by Pseudomonas aeruginosa Strain K385.

25. A method of testing for an efflux pump inhibitor, comprising the steps of:
  a. contacting recombinant microbial cells which express an efflux pump with a test compound, an inducing agent, and a concentration of an antimicrobial agent above the uninduced MIC of said recombinant microbial cells, and
  b. determining whether the intracellular level of said inducing agent is elevated in the presence of said test compound by determining whether said recombinant microbial cells grow better in the presence of said test compound than in the absence of said test compound, wherein an elevated intracellular concentration of said inducing agent induces an inactivator of said antimicrobial agent, and wherein said microbial cells will exhibit greater growth if an efflux pump is inhibited, than if an efflux pump is not inhibited,
  wherein greater growth of said recombinant microbial cells in the presence of said test compound than in the absence of said test compound is indicative that said test compound is an efflux pump inhibitor.

26. The method of claim 25, wherein said recombinant microbial cells are recombinant bacterial cells and said antimicrobial agent is an antibacterial agent.

27. The method of claim 26, wherein said recombinant bacterial cells are derived from a bacterium selected from the group consisting of Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus subsp. hyicus, Staphylococcus haemolyticus, Staphylococcus hominis, Staphylococcus saccharolyticus.

28. The method of claim 27, wherein said recombinant bacterium is derived from Pseudomonas aeruginosa Strain, strain K385, or strain PAO4098E.

29. The method of claim 26, wherein said recombinant bacterial cells contain artificially-inserted DNA constructs comprising a promoter inducible by an elevated intracellular concentration of said inducing agent, transcriptionally linked with a sequence coding for an inactivator of said antibacterial agent,
  wherein said elevated intracellular concentration of said inducing agent induces the expression of said sequence coding for an inactivator of said antibacterial agent.

30. The method of claim 29, wherein said inducing agent induces the expression of a β-lactamase gene and said antibacterial agent is a β-lactam.

31. The method of claim 30, wherein said inducing agent is tetracycline, said β-lactamase gene is the blaS gene, and said β-lactam is a carbapenem.

32. The method of claim 26 or 31, wherein said promoter is the tetA promoter, and wherein said recombinant bacterial cells express the tetR gene.

33. The method of claim 30 or 31, wherein said β-lactamase gene is chromosomally-inserted.

34. The method of claim 25, wherein said bacterium is selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia Acinetobacter calcoaceticus,* and *Acinetobacter haemolyticus.*

35. The method of claim 25, wherein said bacterium is selected from the group consisting of *Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Escherichia coli, Citrobacter freundii, Proteus mirabilis, Proteus vulgaris,* and *Yersinia enterocolitica.*

36. The method of claim 25, wherein said bacterium is selected from the group consisting of *Neisseria gonorrhoeae, Neisseria meningitidis,* Moraxella (*Branhamella catarrhalis*), *Haemophilus influenzae, Haemophilus parainfluenzae, Pasteurella multocida,* and *Pasteurella haemolytica.*

37. The method of claim 25, wherein said bacterium is selected from the group consisting of *Helicobacter pylori, Campylobacter fetus, Campylobacter jejuni, Campylobacter coli, Borrelia burgdorferi, Vibrio cholerae, Vibrio parahaemolyticus, Legionella pneumophila,* and *Gardnerella vaginalis.*

38. The method of claim 25, wherein said bacterium is selected from the group consisting of *Bacteroides fragilis, Bacteroides distasonis,* Bacteroides 3452A homology group, *Bacteroides vulgatus, Bacteroides ovalus, Bacteroides thetaiotaomicron, Bacteroides uniformis, Bacteroides eggerthii, Bacteroides splanchnicus,* and *Clostridium difficile.*

39. The method of claim 25, wherein said bacterium is selected from the group consisting of *Mycobacterium tuberculosis, Mycobacterium avium, Mycobacterium intracellulare, Mycobacterium leprae, Corynebacterium diphteriae,* and *Corynebacterium ulcerans.*

40. The method of claim 25, wherein said bacterium is selected from the group consisting of *Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis, Staphylococcus saccharolyticus.*

41. A method for screening for a non-tetracycline-specific efflux pump inhibitor, comprising the steps of:
   contacting a bacterium with a test compound in the presence of an antibacterial agent effluxed by a non-tetracycline specific efflux pump, wherein said bacterium produces said efflux pump at a level sufficient to maintain the intracellular level of said antibacterial agent at a level such that said antibacterial agent does not inhibit growth of a population of said bacterium by more than 50% in the absence of an efflux pump inhibitor; and
   determining whether said contacting with said test compound inhibits the growth of said bacterium,
   wherein inhibition of the growth of said bacterium by said contacting with said test compound is indicative that said test compound is a said efflux pump inhibitor.

42. The method of claim 41, wherein said antibacterial agent does not inhibit growth of a population of said bacterium by more than 30% in the absence of an efflux pump inhibitor.

43. The method of claim 41, wherein said antibacterial agent does not inhibit growth of a population of said bacterium by more than 10% in the absence of an efflux pump inhibitor.

44. The method of claim 41, 42, or 43, further comprising the step of determining whether there is greater inhibition of growth of said microbe in the presence of said test compound and said antibacterial agent than in the presence of said test compound and absence of said antibacterial agent,
   wherein said greater inhibition is indicative that said test compound is a said efflux pump inhibitor.

45. The method of claim 41, 42, or 43, further comprising comparing the growth of said bacterium with the growth of a second bacterium grown in the presence of said test compound and a subinhibitory concentration of said antibacterial agent, wherein said bacterium does not produce said efflux pump; and
   wherein greater inhibition of growth by said test compound of said bacterium which produces said efflux pump than of said second bacterium is indicative that said test compound is a said efflux pump inhibitor.

46. The method of claim 41, 42, or 43, wherein said bacterium is selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Acinetobacter calcoaceticus,* and *Acinetobacter haemolyticus.*

47. The method of claim 41, 42, or 43, wherein said bacterium is selected from the group consisting of *Salmonella typhimurium, Salmonella typhi, Salmonella paratyphi, Salmonella enteritidis, Shigella dysenteriae, Shigella flexneri, Shigella sonnei, Entetobacter cloacae, Enterobacter aerogenes, Klebsiella pneumoniae, Klebsiella oxytoca, Serratia marcescens, Morganella morganii, Escherichia coli, Citrobacter freundii, Proteus mirabilis, Proteus vulgaris, Providencia alcalifaciens, Providencia rettgeri, Providencia stuartii, Aeromonas hydrophilia, Francisella tularensis, Yersinia enterocolitica, Yersinia pestis, Yersinia pseudotuberculosis,* and *Yersinia intermedia.*

48. The method of claim 41, 42, or 43, wherein said bacterium is selected from the group consisting of *Bordetella pertussis, Bordetella parapertussis, Bordetella bronchiseptica, Neisseria gonorrhoeae, Neisseria meningitidis,* and *Moraxella* (Branhamella) *catarrhalis, Haemophilus influenzae, Haemophilus parainfluenzae, Haemophilus haemolyticus, Haemophilus parahaemolyticus, Haemophilus ducreyi, Pasteurella multocida,* and *Pasteurella haemolytica.*

49. The method of claim 41, 42, or 43, wherein said bacterium is selected from the group consisting of *Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes,* and *Gardnerella vaginalis.*

50. The method of claim 41, 42, or 43, wherein said bacterium is selected from the group consisting of *Bacteroides fragilis, Bacteroides distasonis,* Bacteroides 3452A homology group, *Bacteroides vulgatus, Bacteroides ovalus, Bacteroides thetaiotaomicron, Bacteroides uniformis, Bacteroides eggerthii, Bacteroides splanchnicus* and *Clostridium difficile.*

51. The method of claim 41, 42, or 43, wherein said bacterium is selected from the group consisting of *Myco-*

47

*bacterium tuberculosis, Mycobacterium avium, Mycobacterium intracellulare, Mycobacterium leprae, Corynebacterium diphtheriae,* and *Corynebacterium ulcerans.*

52. The method of claim 41, 42, or 43, wherein said bacterium is selected from the group consisting of *Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis, Staphylococcus saccharolyticus.*

53. A method of enhancing the antimicrobial effect of an antimicrobial agent against a microbe, comprising contacting said microbe with said antimicrobial agent and a non-tetracycline-specific efflux pump inhibitor in an amount effective to inhibit an efflux pump in said microbe, wherein said microbe is a bacterium and said antimicrobial agent is a quinolone antibacterial agent, and wherein said efflux pumnp inhibitor has a structure of any of structures 1, 2, 3, or 4, namely:

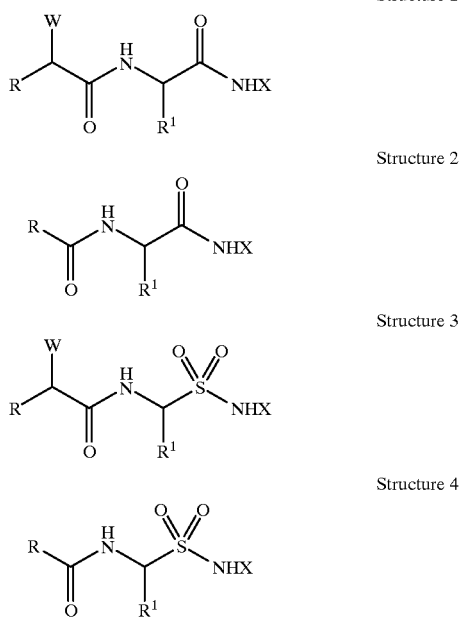

Structure 1

Structure 2

Structure 3

Structure 4 wherein

R is alkyl $(C_1-C_4)$; fluoroalkyl $(C_1-C_4)$; perfluoroalkyl $(C_1-C_4)$; alkoxy $(C_1-C_4)$; alkylthio $(C_1-C_4)$; halogen (Br, Cl, F or I); aryl $(C_6-C_{10})$; monosubstituted aryl $(C_6-C_{10})$, substituted with alkyl $(C_1-C_4)$, alkoxy $(C_1-C_4)$, alkylthio $(C_1-C_4)$, halogen (Br, Cl, F or I), amino, monosubstituted amino wherein the substituent is alkyl $(C_1-C_4)$, disubstituted amino wherein the substituents are any combination of alkyl $(C_1-C_4)$], or hydroxyl; disubstituted aryl $(C_6-C_{10})$ substituted with any combination of alkyl $(C_1-C_4)$, alkoxy $(C_1-C_4)$, alkylthio $(C_1-C_4)$, halogen (Br, Cl, F or I) and amino, 2-(or 3-)-thienyl, 2-(or 3-)-furanyl, or 2-(3- or 4-)-pyridyl;

W is H; $NH_2$; monosubstitited amino wherein the substituent is alkyl $(C_1-C_4)$; disubstituted amino substituted with any combination of alkyl $(C_1-C_4)$; an aza-heterocycle; halogen (Br, Cl, F, I); hydroxyl; alkoxy $(C_1-C_4)$; or alkylthio $(C_1-C_4)$;

48

$R^1$ is $(CH_2)_nNR^aR_b$; $(CH_2)_nNR^bR^c$; $(CH_2)_nNHC=(NR^a)NR^bR^c$; $(CH_2)_nSNHC=(NR^a)NR^bR^c$; $(CH_2)_nC=(NR^a)NR^bR^c$; $(CH_2)_nN=CNR^bR^c$, wherein (n is 2–4) and $R^a$ ($R^b$ or $R^c$) are independently H, alkyl $(C_1-C_4)$, aryl $(C_6)$, substituted aryl, benzyl, substituted benzyl substituted with alkyl $(C_1-C_4)$, alkoxy $(C_1-C_4)$, alkylthio $(C_1-C_4)$, halogen (Br, Cl, F or I), or amino, or $R^a+R^b$ is $(CH_2)_{2-3}$ or —CH=CH—, X is aryl $(C_6-C_{10})$; $—(CH_2)_{0-2}$aryl $(C_6-C_{10})$; substituted aryl $(C_6-C_{10})$ substituted with alkyl $(C_1-C_4)$, alkoxy $(C_1-C_4)$, alkylthio $(C_1-C_4)$, halogen (Br, Cl, F or I), or amino; substituted $—(CH_2)_{0-2}$aryl $(C_6-C_{10})$ with substitution on the aryl unit with alkyl $(C_1-C_4)$, alkoxy $(C_1-C_4)$, alkylthio $(C_1-C_4)$, halogen (Br, Cl, F or I), or amino; 2-(or 3-)-thienyl; 2-(or 3-)-furyl; 2-(3- or 4-)-pyridyl; benzofuranyl with attachment at any position on the benzofuran ring; or benzothienyl with attachment at any position on the benzothiophene ring; and where there are centers of asymmetry, the absolute stereochemistry can be either R or S-configuration, or there can be a racemic mixture.

54. The method of claim 53, wherein said bacterium is selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Acinetobacter calcoaceticus,* and *Acinetobacter haemolyticus.*

55. The method of claim 53, wherein said bacterium is selected from the group consisting of *Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Morganella morganii, Escherichia coli, Citrobacter freundii, Proteus mirabilis Proteus vulgaris, Providencia alcalifaciens, Providencia rettgeri, Providencia stuartii, Aeromonas hydrophilia, Francisella tularensis, Yersinia enterocolitica, Yersinia pestis, Yersinia pseudotuberculosis,* and *Yersinia intermedia.*

56. The method of claim 53, wherein said bacterium is selected from the group consisting of *Neisseria gonorrhoeae, Neisseria meningitidis,* Moraxella (*Branhamella catarrhalis*), *Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida* and *Pasteurella haemolytica.*

57. The method of claim 53, wherein said bacterium is selected from the group consisting of *Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes,* and *Gardnerella vaginalis.*

58. The method of claim 53, wherein said bacterium is selected from the group consisting of *Bacteroides fragilis, Bacteroides distasonis,* Bacteroides 3452A homology group, *Bacteroides vulgatus, Bacteroides ovalus, Bacteroides thetaiotaomicron, Bacteroides uniformis, Bacteroides eggerthii, Bacteroides splanchnicus,* and *Clostridium difficile.*

59. The method of claim 53, wherein said bacterium is selected from the group consisting of *Mycobacterium tuberculosis, Mycobacterium avium, Mycobacterium intracellulare, Mycobacterium leprae, Corynebacterium diphtheriae,* and *Corynebacterium ulcerans.*

60. The method of claim 53, wherein said bacterium is selected from the group consisting of *Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis, Staphylococcus saccharolyticus.*

61. A method of enhancing the antimicrobial effect of an antimicrobial agent against a microbe, comprising contacting said microbe with said antimicrobial agent and a non-tetracycline-specific efflux pump inhibitor in an amount effective to inhibit an efflux pump in said microbe, wherein said microbe is a bacterium and said antimicrobial agent is a tetracycline antibacterial agent, and wherein said efflux pump inhibitor has a structre of any of structures 1, 2, 3, or 4, namely:

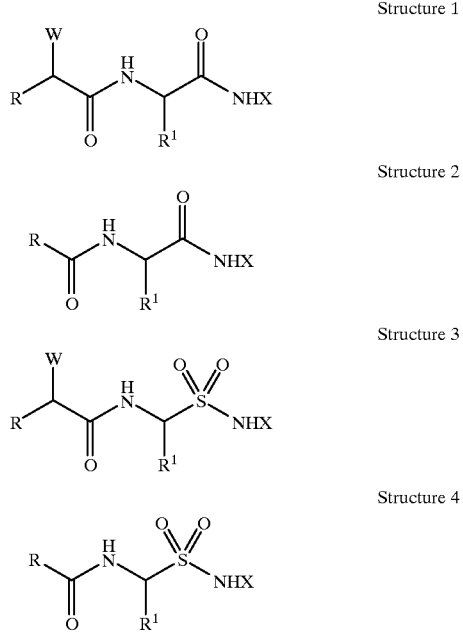

Structure 1

Structure 2

Structure 3

Structure 4 wherein

R is alkyl ($C_1$–$C_4$); fluoroalkyl ($C_1$–$C_4$); perfluoroalkyl ($C_1$–$C_4$); alkoxy ($C_1$–$C_4$); alkylthio ($C_1$–$C_4$); halogen (Br, Cl, F or I); aryl ($C_6$–$C_{10}$); monosubstituted aryl ($C_6$–$C_{10}$), substituted with alkyl ($C_1$–$C_4$), alkoxy ($C_1$–$C_4$), alkylthio ($C_1$–$C_4$), halogen (Br, Cl, F or I), amino, monosubstituted amino wherein the substituent is alkyl ($C_1$–$C_4$), disubstituted amino wherein the substituents are any combination of alkyl ($C_1$–$C_4$)], or hydroxyl; disubstituted alkyl ($C_6$–$C_{10}$) substituted with any combination of alkyl ($C_1$–$C_4$), alkoxy ($C_1$–$C_4$), alkylthio ($C_1$–$C_4$), halogen (Br, Cl, F or I) and amino, 2-(or 3-)-thienyl, 2-(or 3-)-furanyl, or 2-(3- or 4-)-pyridyl;

W is H; $NH_2$; monosubstituted amino wherein the substituent is alkyl ($C_1$–$C_4$); disubstituted amino substituted with any combination of alkyl ($C_1$–$C_4$); an aza-heterocycle; halogen (Br, Cl, F, I); hydroxyl; alkoxy ($C_1$–$C_4$); or alkylthio ($C_1$–$C_4$);

$R^1$ is $(CH_2)_n NR^a R_b$; $(CH_2)_n NR^b R^c$; $(CH_2)_n NHC=(NR^a) NR^b R^c$; $(CH_2)_n SNHC=(NR^a) NR^b R^c$; $(CH_2)_n C=(NR^a) NR^b R^c$; $(CH_2)_n N=CNR^b R^c$, wherein (n is 2–4)

and $R^a$ ($R^b$ or $R^c$) are independently H, alkyl ($C_1$–$C_4$), aryl ($C_6$), substituted aryl, benzyl, substituted benzyl substituted with alkyl ($C_1$–$C_4$), alkoxy ($C_1$–$C_4$), alkylthio ($C_1$–$C_4$), halogen (Br, Cl, F or I), or amino, or $R^a+R^b$ is $(CH_2)_{2-3}$ or —CH=CH—;

X is aryl ($C_6$–$C_{10}$); —$(CH_2)_{0-2}$aryl ($C_6$–$C_{10}$); substituted aryl ($C_6$–$C_{10}$) substituted with alkyl ($C_1$–$C_4$), alkoxy ($C_1$–$C_4$), alkylthio ($C_1$–$C_4$), halogen (Br, Cl, F or I), or amino; substituted —$(CH_2)_{0-2}$aryl ($C_6$–$C_{10}$) with substitution on the aryl unit with alkyl ($C_1$–$C_4$), alkoxy ($C_1$–$C_4$), alkylthio ($C_1$–$C_4$), halogen (Br, Cl, F or I), or amino; 2-(or 3-)-thienyl; 2-(or 3-)-furyl; 2-(3- or 4-)-pyridyl; benzofuranyl with attachment at any position on the benzofuran ring; or benzothienyl with attachment at any position on the benzothiophene ring; and where there are centers of asymmetry, the absolute stereochemistry can be either R or S-configuration, or there can be a racemic mixture.

62. The method of claim 61, wherein said bacterium is selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkolderia cepacia, Acinetobacter calcoaceticus,* and *Acinetobacter haemolyticus.*

63. The method of claim 61, wherein said bacterium is selected from the group consisting of *Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Morganella morganii, Escherichia coli, Citrobacter freundii, Proteus mirabilis, Proteus vulgaris, Providencia alcalifaciens, Providencia rettgeri, Providencia stuartii, Aeromonas hydrophilia, Francisella tularensis, Yersinia enterocolitica, Yersinia pestis, Yersinia pseudotuberculosis,* and *Yersinia intermedia.*

64. The method of claim 61, wherein said bacterium is selected from the group consisting of *Neisseria gonorrhoeae, Neisseria meningitidis, Moraxella* (Branhamella) *catarrhalis, Bordetella pertussis, Bordetella parapertussis, Bordelella bronchiseptica, Haemophilus influenzae, Haemophilus parainfluenzae, Haemophilus haemolyticus, Haemophilus parahaemolyticus, Haemophilus ducreyi, Pasteurella multocida,* and *Pasteurella haemolytica.*

65. The method of claim 61, wherein said bacterium is selected from the group consisting of *Campylobacter fetus, Campylobacter jejuni, Campylobacter coli, Borrelia burgdorferi, Vibrio cholerae, Vibrio parahaemolyticus, Legionella pneumophila, Listeria monocytogenes,* and *Gardnerella vaginalis.*

66. The method of claim 61, wherein said bacterium is selected from the group consisting of *Mycobacterium tuberculosis, Mycobacterium avium, Mycobacterium intracellulare, Mycobacterium leprae, Corynebacterium diphtheriae,* and *Corynebacterium ulcerans.*

67. The method of claim 61, wherein said bacterium is selected from the group consisting of *Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis, Staphylococcus saccharolyticus.*

68. A method of enhancing the antimicrobial effect of an antimicrobial agent against a microbe, comprising contacting said microbe with said antimicrobial agent and a non-tetracycline-specific efflux pump inhibitor in an amount effective to inhibit an efflux pump in said microbe, wherein said microbe is a bacterium and said antimicrobial agent is a β-lactam antibacterial agent, and wherein said efflux pump inhibitor has a structure of any of structures 1, 2, 3, or 4, namely:

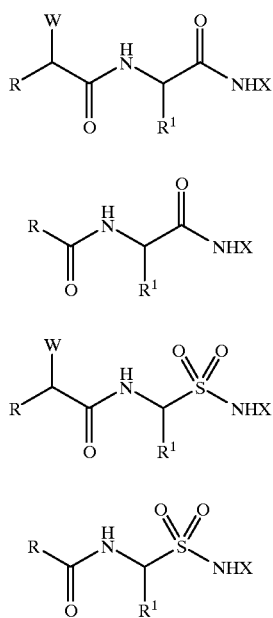

Structure 1

Structure 2

Structure 3

Structure 4 wherein

R is alkyl ($C_1$–$C_4$); fluoroalkyl ($C_1$–$C_4$); perfluoroalkyl ($C_1$–$C_4$); alkoxy ($C_1$–$C_4$), alkylthio ($C_1$–$C_4$); halogen (Br, Cl, F or I); aryl ($C_6$–$C_{10}$); monosubstituted aryl ($C_6$–$C_{10}$), substituted with alkyl ($C_1$–$C_4$), alkoxy ($C_1$–$C_4$), alkylthio ($C_1$–$C_4$), halogen (Br, Cl, F or I), amino, monosubstituted amino wherein the substituent is alkyl ($C_1$–$C_4$), disubstituted amino wherein the substituents are any combination of alkyl ($C_1$–$C_4$)], or hydroxyl; disubstituted aryl ($C_6$–$C_{10}$) substituted with any combination of alkyl ($C_1$–$C_4$), alkoxy ($C_1$–$C_4$), alkylthio ($C_1$–$C_4$), halogen (Br, Cl, F or I) and amino, 2-(or 3-)-thienyl, 2-(or 3-)-furanyl, or 2-(3- or 4-)-pyridyl;

W is H; $NH_2$; monosubstituted amino wherein the substituent is alkyl ($C_1$–$C_4$); disubstituted amino substituted with any combination of alkyl ($C_1$–$C_4$); an azeheterocycle; halogen (Br, Cl, F, I); hydroxyl; alkoxy ($C_1$–$C_4$); or alkylthio ($C_1$–$C_4$);

$R^1$ is $(CH_2)_n NR^a R_b$; $(CH_2)_n NR^b R^c$; $(CH_2)_n NHC=(NR^a)NR^b R^c$; $(CH_2)_n SNHC=(NR^a)NR^b R^c$; $(CH_2)_n C=(NR^a)NR^b R^c$; $(CH_2)_n N=CNR^b R^c$, wherein (n is 2–4) and $R^a$ ($R^b$ or $R^c$) are independently H, alkyl ($C_1$–$C_4$), aryl ($C_6$), substituted aryl, benzyl, substituted benzyl substituted with alkyl ($C_1$–$C_4$), alkoxy ($C_1$–$C_4$), alkylthio ($C_1$–$C_4$), halogen (Br, Cl, F or I), or amino, or $R^a + R^b$ is $(CH_2)_{2-3}$ or —CH=CH—;

X is aryl ($C_6$–$C_{10}$); —$(CH_2)_{0-2}$aryl ($C_6$–$C_{10}$); substituted aryl ($C_6$–$C_{10}$) substituted with alkyl ($C_1$–$C_4$), alkoxy ($C_1$–$C_4$), alkylthio ($C_1$–$C_4$), halogen (Br, Cl, F or I), or amino; substituted —$(CH_2)_{0-2}$aryl ($C_6$–$C_{10}$) with substitution on the aryl unit with alkyl ($C_1$–$C_4$), alkoxy ($C_1$–$C_4$), alkylthio ($C_1$–$C_4$), halogen (Br, Cl, F or I), or amino; 2-(or 3-)-thienyl; 2-(or 3-)-furyl; 2-(3- or 4-)-pyridyl; benzofuryl with attachment at any position on the benzofuran ring; or benzothienyl with attachment at any position on the benzothiophene ring; and where there are centers of asymmetry, the absolute stereochemistry can be either R or S-configuration, or there can be a racemic mixture.

69. The method of claim 68, wherein said bacterium is selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Acinetobacter calcoaceticus,* and *Acinetobacter haemolyticus.*

70. The method of claim 68, wherein said bacterium is selected fron the group consisting of *Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Morganella morganii, Escherichia coli, Citrobacter freundii, Proteus mirabilis, Proteus vulgaris, Providencia alcalifaciens, Providencia rettgeri, Providencia stuartii, Aeromonas hydrophilia, Francisella tularensis, Yersinia enterocolitica, Yersinia pestis, Yersinia pseudotuberculosis,* and *Yersinia intermedia.*

71. The method of claim 68, wherein said bacterium is selected from the group consisting of *Bordetella pertussis, Bordetella parapertussis, Bordetella bronchiseptica, Neisseria gonorrhoeae, Neisseria meningitidis, Moraxella (Branhamella) catarrhalis, Haemophilus influenzae, Haemophilus parainfluenzae, Haemophilus haemolyticus, Haemophilus parahaemolyticus, Haemophilus ducreyi, Pasteurella multocida,* and *Pasteurella haemolytica.*

72. The method of claim 68, wherein said bacterium is selected from the group consisting of *Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes,* and *Gardnerella vaginalis.*

73. The method of claim 68, wherein said bacterium is selected from the group consisting of *Bacteroides fragilis, Bacteroides distasonis,* Bacteroides 3452A homology group, *Bacteroides vulgatus, Bacteroides ovalus, Bacteroides thetaiotaomicron, Bacteroides uniformis, Bacteroides eggerthii, Bacteroides splanchnicus,* and *Clostridium difficile.*

74. The method of claim 68, wherein said bacterium is selected from the group consisting of *Mycobacterium tuberculosis, Mycobacterium avium, Mycobacterium intracellulare, Mycobacterium leprae, Corynebacterium diphtheriae,* and *Corynebacterium ulcerans.*

75. A method of enhancing the antimicrobial effect of an antimicrobial agent against a microbe, comprising contacting said microbe with said antimicrobial agent and a non-tetracycline-specific efflux pump inhibitor in an amount effective to inibit an efflux pump in said microbe, wherein said microbe is a bacterium and said antimicrobial agent is a coumermycin antibacterial agent, and wherein said efflux pump inhibitor has a structure of any of structures 1, 2, 3, or 4, namely:

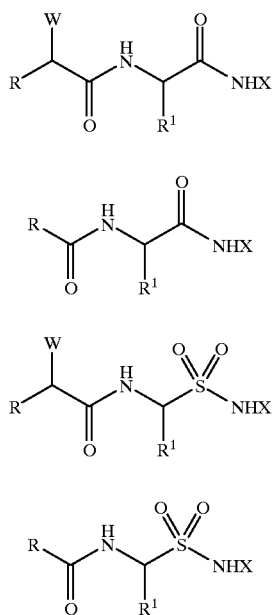

Structure 1

Structure 2

Structure 3

Structure 4 wherein

R is alkyl ($C_1$–$C_4$); fluoroalkyl ($C_1$–$C_4$); perfluoroalkyl ($C_1$–$C_4$); alkoxy ($C_1$–$C_4$); alkylthio ($C_1$–$C_4$); halogen (Br, Cl, F or I); aryl ($C_6$–$C_{10}$); monosubstituted aryl ($C_6$–$C_{10}$), substituted with alkyl ($C_1$–$C_4$), alkoxy ($C_1$–$C_4$), alkylthio ($C_1$–$C_4$), halogen (Br, Cl, F or I), amino, monosubstituted amino wherein the substituent is alkyl ($C_1$–$C_4$), disubstituted amino wherein the substituents are any combination of alkyl ($C_1$–$C_4$)], or hydroxyl; disubstituted aryl ($C_6$–$C_{10}$) substituted with any combination of alkyl ($C_1$–$C_4$), alkoxy ($C_1$–$C_4$), alkylthio ($C_1$–$C_4$), halogen (Br, Cl, F or I) and amino, 2-(or 3-)-thienyl, 2-(or 3-)-furanyl, or 2-(3- or 4-)-pyridyl;

W is H; $NH_2$; monosubstituted amino wherein the substituent is alkyl ($C_1$–$C_4$); disubstituted amino substituted with any combination of alkyl ($C_1$–$C_4$); an aza-heterocycle; halogen (Br, Cl, F, I); hydroxyl; alkoxy ($C_1$–$C_4$); or alkylthio ($C_1$–$C_4$);

$R^1$ is $(CH_2)_n NR^a R_b$; $(CH_2)_n NR^b R^c$; $(CH_2)_n NHC = (NR^a) NR^b R^c$; $(CH_2)_n SNHC = (NR^a) NR^b R^c$; $(CH_2)_n C = (NR^a) NR^b R^c$; $(CH_2)_n N = CNR^b R^c$, wherein (n is 2–4) and $R^a$ ($R^b$ or $R^c$) are independently H, alkyl ($C_1$–$C_4$), aryl ($C_6$), substituted aryl, benzyl, substituted benzyl substituted with alkyl ($C_1$–$C_4$), alkoxy ($C_1$–$C_4$), alkylthio ($C_1$–$C_4$), halogen (Br, Cl, F or I), or amino, or $R^a + R^b$ is $(CH_2)_{2-3}$ or —CH=CH—;

X is aryl ($C_6$–$C_{10}$); —$(CH_2)_{0-2}$aryl ($C_6$–$C_{10}$); substituted aryl ($C_6$–$C_{10}$) substituted with alkyl ($C_1$–$C_4$), alkoxy ($C_1$–$C_4$), alkylthio ($C_1$–$C_4$), halogen (Br, Cl, F or I), or amino; substituted —$(CH_2)_{0-2}$aryl ($C_6$–$C_{10}$) with substitution on the aryl unit with alkyl ($C_1$–$C_4$), alkoxy ($C_1$–$C_4$), alkylthio ($C_1$–$C_4$), halogen (Br, Cl, F or I), or amino; 2-(or 3-)-thienyl; 2-(or 3-)-furyl; 2-(3- or 4-)-pyridyl; benzofurnyl with attachment at any position on the benzofuran ring; or benzothienyl with attachment at any position on the benzothiophene ring; and where there are centers of asymmetry, the absolute stereochemistry can be either R or S-confguration, or there can be a racemic mixture.

76. The method of claim 75, wherein said bacterium is selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Acinetobacter calcoaceticus*, and *Acinetobacter haemolyticus*.

77. The method of claim 75, wherein said bacterium is selected from the group consisting of *Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Morganella morganii, Escherichia coli, Citrobacter freundii, Proteus mirabilis, Proteus vulgaris, Providencia alcalifaciens, Providencia rettgeri, Providencia stuartii, Aeromonas hydrophilia, Francisella tularensis, Yersinia enterocolitica, Yersinia pestis, Yersinia pseudotuberculosis*, and *Yersinia intermedia*.

78. The method of claim 75, wherein said bacterium is selected from the group consisting of *Neisseria gonorrhoeae, Neisseria meningitidis, Moraxella* (Branhamella) *catarrhalis, Bordetella pertussis, Bordetella parapertussis, Bordetella bronchiseptica, Haemophilus influenzae, Haemophilus parainfluenzae, Haemophilus haemolyticus, Haemophilus parahaemolyticus*, and *Haemophilus ducreyi, Pasteurella multocida, Pasteurella haemolytica*.

79. The method of claim 75, wherein said bacterium is selected from the group consisting of *Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes*, and *Gardnerella vaginalis*.

80. The method of claim 75, wherein said bacterium is selected from the group consisting of *Bacteroides fragilis, Bacteroides distasonis*, Bacteroides 3452A homology group, *Bacteroides vulgatus, Bacteroides ovalus, Bacteroides thetaiotaomicron, Bacteroides uniformis, Bacteroides eggerthii, Bacteroides splanchnicus*, and *Clostridium difficile*.

81. The method of claim 75, wherein said bacterium is selected from the group consisting of *Mycobacterium tuberculosis, Mycobacterium avium, Mycobacterium intracellulare, Mycobacterium leprae, Corynebacterium diphtheriae*, and *Corynebacterium ulcerans*.

82. The method of claim 75, wherein said bacterium is selected from the group consisting of *Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis, Staphylococcus saccharolyticus*.

83. The method of enhancing the antimicrobial effect of an antimicrobial agent against a microbe, comprising contacting said microbe with said antimicrobial agent and a noon-tetracycline-specific efflux pump inhibitor in an amount effective to inhibit an efflux pump in said microbe, wherein said microbe is a bacterium and said antimicrobial agent is chloramphenicol, and wherein said efflux pump inhibitor has a stucture of any of structures 1, 2, 3, or 4, namely:

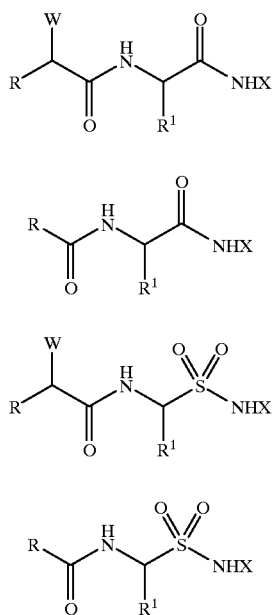

Structure 1
Structure 2
Structure 3
Structure 4 wherein

R is alkyl ($C_1$–$C_4$); fluoroalkyl ($C_1$–$C_4$); perfluoroalkyl ($C_1$–$C_4$); alkoxy ($C_1$–$C_4$); alkylthio ($C_1$–$C_4$); halogen (Br, Cl, F or I); aryl ($C_6$–$C_{10}$); monosubstituted aryl ($C_6$–$C_{10}$), substituted with alkyl ($C_1$–$C_4$), alkoxy ($C_1$–$C_4$), alkylthio ($C_1$–$C_4$), halogen (Br, Cl, F or I), amino, monosubstituted amino wherein the substituent is alkyl ($C_1$–$C_4$), disubstituted amino wherein the substituents are any combination of alkyl ($C_1$–$C_4$)], or hydroxyl; disubstituted aryl ($C_6$–$C_{10}$) substituted with any combination of alkyl ($C_1$–$C_4$), alkoxy ($C_1$–$C_4$), alkylthio ($C_1$–$C_4$), halogen (Br, Cl, F or I) and amino, 2-(or 3-)-thienyl, 2-(or 3-)-furanyl, or 2-(3- or 4-)-pyridyl;

W is H; $NH_2$; monosubstituted amino wherein the substituent is alkyl ($C_1$–$C_4$); disubstituted amino substituted with any combination of alkyl ($C_1$–$C_4$); an azaheterocycle; halogen (Br, Cl, F, I); hydroxyl; alkoxy ($C_1$–$C_4$); or alkylthio ($C_1$–$C_4$);

$R^1$ is $(CH_2)_n NR^a R_b$; $(CH_2)_n NR^b R^c$; $(CH_2)_n NHC=(NR^a)NR^b R^c$; $(CH_2)_n SNHC=(NR^a)NR^b R^c$; $(CH_2)_n C=(NR^a)NR^b R^c$; $(CH_2)_n N=CNR^b R^c$, wherein (n is 2–4) and $R^a$ ($R^b$ or $R^c$) are independently H, alkyl ($C_1$–$C_4$), aryl ($C_6$), substituted aryl, benzyl, substituted benzyl substituted with alkyl ($C_1$–$C_4$), alkoxy ($C_1$–$C_4$), alkylthio ($C_1$–$C_4$), halogen (Br, Cl, F or I), or amino, or $R^a + R^b$ is $(CH_2)_{2-3}$ or —CH=CH—;

X is aryl ($C_6$–$C_{10}$); —$(CH_2)_{0-2}$aryl ($C_6$–$C_{10}$); substituted aryl ($C_6$–$C_{10}$) substituted with alkyl ($C_1$–$C_4$), alkoxy ($C_1$–$C_4$), alkylthio ($C_1$–$C_4$), halogen (Br, Cl, F or I), or amino, substituted —$(CH_2)_{0-2}$aryl ($C_6$–$C_{10}$) with substitution on the aryl unit with alkyl ($C_1$–$C_4$), alkoxy ($C_1$–$C_4$), alkylthio ($C_1$–$C_4$), halogen (Br, Cl, F or I), or amino; 2-(or 3-)-thienyl; 2-(or 3-)-furyl; 2-(3- or 4-)-pyridyl; benzofuranyl with attachment at any position on the benzofuran ring; or benzothienyl with attachment at any position on the benzothiophene ring; and where there are centers of asymmetry, the absolute stereochemistry can be either R or S-configuration, or there can be a racemic nixture.

84. The method of claim 83, wherein said bacterium is selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Acinetobacter calcoaceticus,* and *Acinetobacter haemolyticus.*

85. The method of claim 83, wherein said bacterium is selected from the group consisting of *Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Morganella morganii, Escherichia coli, Citrobacter freundii, Proteus mirabilis Proteus vulgaris, Providencia alcalifaciens, Providencia rettgeri, Providencia stuartii, Aeromonas hydrophilia, Francisella tularensis, Yersinia enterocolitica, Yersinia pestis, Yersinia pseudotuberculosis,* and *Yersinia intermedia.*

86. The method of claim 83, wherein said bacterium is selected from the group consisting of *Neisseria gonorrhoeae, Neisseria meningitidis, Moraxella (Branhamella) catarrhalis, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida,* and *Pasteurella haemolytica.*

87. The method of claim 83, wherein said bacterium is selected from the group consisting of *Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes,* and *Gardnerella vaginalis.*

88. The method of claim 83, wherein said bacterium is selected from the group consisting of *Bacteroides fragilis, Bacteroides distasonis,* Bacteroides 3452A homology group, *Bacteroides vulgatus, Bacteroides ovalus, Bacteroides thetaiotaomicron, Bacteroides uniformis, Bacteroides eggerthii, Bacteroides splanchnicus,* and *Clostridium difficile.*

89. The method of claim 83, wherein said bacterium is selected from the group consisting of *Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis, Staphylococcus saccharolyticus.*

90. A method of enhancing the antimicrobial effect of an antimicrobial agent against a microbe, comprising contacting said microbe with said antimicrobial agent and a non-tetracycline-specific efflux pump inhibitor in an amount effective to inhibit an efflux pump in said microbe, wherein said microbe is a bacterium and said antimicrobial agent is a glycopeptide antibacterial agent, and wherein said efflux pump inhibitor has a structure of any of structures 1, 2, 3, or 4, namely:

Structure 1

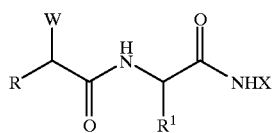

Structure 2

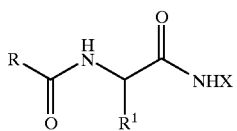

Structure 3

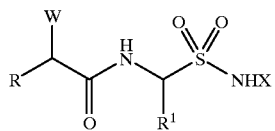

Structure 4

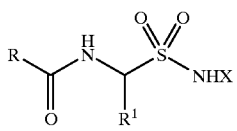

wherein
- R is alkyl ($C_1$–$C_4$); fluoroalkyl ($C_1$–$C_4$); perfluoroalkyl ($C_1$–$C_4$); alkoxy ($C_1$–$C_4$) alkylthio ($C_1$–$C_4$); halogen (Br, Cl, F or I); aryl ($C_6$–$C_{10}$); monosubstituted aryl ($C_6$–$C_{10}$), substituted with alkyl ($C_1$–$C_4$), alkoxy ($C_1$–$C_4$), alkylthio ($C_1$–$C_4$), halogen (Br, Cl, F or I), amino, monosubstituted amino wherein the substituent is alkyl ($C_1$–$C_4$), disubstituted amino wherein the substituents are any combination of alkyl ($C_1$–$C_4$)], or hydroxyl; disubstituted aryl ($C_6$–$C_{10}$) substituted with any combination of alkyl ($C_1$–$C_4$), alkoxy ($C_1$–$C_4$), alkylthio ($C_1$–$C_4$), halogen (Br, Cl, F or I) and amino, 2-(or 3-)-thienyl, 2-(or 3-)-furanyl, or 2-(3- or 4-)-pyridyl;
- W is H; $NH_2$; monosubstituted amino wherein the substituent is alkyl ($C_1$–$C_4$); disubstituted amino substituted with any combination of alkyl ($C_1$–$C_4$); an aza-heterocycle; halogen (Br, Cl, F, I); hydroxyl; alkoxy ($C_1$–$C_4$); or alkylthio ($C_1$–$C_4$);
- $R^1$ is $(CH_2)_n NR^a R_b$; $(CH_2)_n NR^b R^c$; $(CH_2)_n NHC=(NR^a) NR^b R^c$; $(CH_2)_n SNHC=(NR^a) NR^b R^c$; $(CH_2)_n C=(NR^a) NR^b R^c$; $(CH_2)_n N=CNR^b R^c$, wherein (n is 2–4) and $R^a$ ($R^b$ or $R^c$) are independently H, alkyl ($C_1$–$C_4$), aryl ($C_6$), substituted aryl, benzyl, substituted benzyl substituted with alkyl ($C_1$–$C_4$), alkoxy ($C_1$–$C_4$), alkylthio ($C_1$–$C_4$), halogen (Br, Cl, F or I), or amino, or $R^a+R^b$ is $(CH_2)_{2-3}$ or —CH=CH—;
- X is aryl ($C_6$–$C_{10}$); —$(CH_2)_{0-2}$aryl ($C_6$–$C_{10}$); substituted aryl ($C_6$–$C_{10}$), substituted with alkyl ($C_1$–$C_4$), alkoxy ($C_1$–$C_4$), alkylthio ($C_1$–$C_4$), halogen (Br, Cl, F or I), or amino; substituted —$(CH_2)_{0-2}$aryl ($C_6$–$C_{10}$) with substitution on the aryl unit with alkyl ($C_1$–$C_4$), alkoxy ($C_1$–$C_4$), alkylthio ($C_1$–$C_4$), halogen (Br, Cl, F or I), or amino; 2-(or 3-)thienyl; 2-(or 3-)-furyl; 2-(3- or 4-)-pyridyl; benzofuranyl with attachment at any position on the benzofuran ring; or benzothienyl with attachment at any position on the benzothiophene ring; and
- where there are centers of asymmetry, the absolute stereochemistry can be either R or S-configuration, or there can be a racemic mixture.

91. The method of claim 90, wherein said bacterium is selected from the group consisting of *Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis, Staphylococcus saccharolyticus, Listeria monocytogenes, Clostridium difficile, Corynebacterium diphtheriae*, and *Corynebacterium ulcerans*.

92. A method of enhancing the antimicrobial effect of an antimicrobial agent against a microbe, comprising contacting said microbe with said antimicrobial agent and a non-tetracycline-specific efflux pump inhibitor in an amount effective to inhibit an efflux pump in said microbe,
wherein said microbe is a bacterium and said antimicrobial agent is an aminoglycoside antibacterial agent, and
wherein said efflux pump inhibitor has a structure of any of structures 1, 2, 3, or 4, namely:

Structure 1

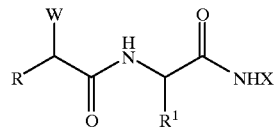

Structure 2

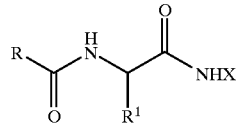

Structure 3

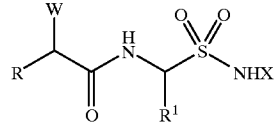

Structure 4

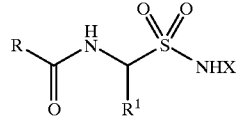

wherein
- R is alkyl ($C_1$–$C_4$); fluoroalkyl ($C_1$–$C_4$); perfluoroalkyl ($C_1$–$C_4$); alkoxy ($C_1$–$C_4$); alkylthio ($C_1$–$C_4$); halogen (Br, Cl, F or I); aryl ($C_6$–$C_{10}$); monosubstituted aryl ($C_6$–$C_{10}$), substituted with alkyl ($C_1$–$C_4$), alkoxy ($C_1$–$C_4$), alkylthio ($C_1$–$C_4$), halogen (Br, Cl, F or I), amino, monosubstituted amino wherein the substituent is alkyl ($C_1$–$C_4$), disubstituted amino wherein the substituents are any combination of alkyl ($C_1$–$C_4$)], or hydroxyl; disubstituted aryl ($C_6$–$C_{10}$) substituted with any combination of alkyl ($C_1$–$C_4$), alkoxy ($C_1$–$C_4$), alkylthio ($C_1$–$C_4$), halogen (Br, Cl, F or I) and amino, 2-(or 3-)-thienyl, 2-(or 3-)-furanyl, or 2-(3- or 4-)-pyridyl;
- W is H; $NH_2$; monosubstituted amino wherein the substituent is alkyl ($C_1$–$C_4$); disubstituted amino substituted with any combination of alkyl ($C_1$–$C_4$); an aza-heterocycle; halogen (Br, Cl, F, I); hydroxyl; alkoxy ($C_1$–$C_4$); or alkylthio ($C_1$–$C_4$);
- $R^1$ is $(CH_2)_n NR^a R_b$; $(CH_2)_n NR^b R^c$; $(CH_2)_n NHC=(NR^a) NR^b R^c$; $(CH_2)_n SNHC=(NR^a) NR^b R^c$; $(CH_2)_n C=$ (NR$^a$)NR$^b$R$^c$; (CH$_2$)$_n$N=CNR$^b$R$^c$, wherein (n is 2–4) and R$^a$ (R$^b$ or R$^c$) are independently H, alkyl (C$_1$–C$_4$), aryl (C$_6$), substituted aryl, benzyl, substituted benzyl substituted with alkyl (C$_1$–C$_4$), alkoxy (C$_1$–C$_4$), alkylthio (C$_1$–C$_4$), halogen (Br, Cl, F or I), or amino, or R$^a$+R$^b$ is (CH$_2$)$_{2-3}$ or —CH=CH—;

X is aryl (C$_6$–C$_{10}$); —(CH$_2$)$_{0-2}$aryl (C$_6$–C$_{10}$); substituted aryl (C$_6$–C$_{10}$) substituted with alkyl (C$_1$–C$_4$), alkoxy (C$_1$–C$_4$), alkylthio (C$_1$–C$_4$), halogen (Br, Cl, F or I), or amino; substituted —(CH$_2$)$_{0-2}$aryl (C$_6$–C$_{10}$) with substitution on the aryl unit with alkyl (C$_1$–C$_4$), alkoxy (C$_1$–C$_4$), alkylthio (C$_1$–C$_4$), halogen (Br, Cl, F or I), or amino, 2-(or 3-)-thienyl; 2-(or 3-)-furyl; 2-(3- or 4-)-pyridyl; benzofuranyl with attachment at any position on the benzofuran ring; or benzothienyl with attachment at any position on the benzothiophene ring; and where there are centers of asymmetry, the absolute stereochemistry can be either R or S-configuration, or there can be a racemic mixture.

93. The method of claim 92, wherein said bacterium is selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Acinetobacter calcoaceticus,* and *Acinetobacter haemolyticus.*

94. The method of claim 92, wherein said bacterium is selected from the group consisting of *Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Morganella morganii, Escherichia coli, Citrobacter freundii, Proteus mirabilis Proteus vulgaris, Providencia alcalifaciens, Providencia rettgeri, Providencia stuartii, Aeromonas hydrophilia, Francisella tularensis, Yersinia enterocolitica, Yersinia pestis, Yersinia pseudotuberculosis,* and *Yersinia intermedia.*

95. The method of claim 92, wherein said bacterium is selected fom the group consisting of *Neisseria gonorrhoeae, Neisseria meningitidis, Moraxella* (Branhamella) *catarrhalis, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida,* and *Pasteurella haemolytica.*

96. The method of claim 92, wherein said bacterium is selected from the group consisting of *Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes,* and *Gardnerella vaginalis.*

97. The method of claim 92, wherein said bacterium is selected from the group consisting of *Mycobacterium tuberculosis, Mycobacterium avium, Mycobacterium intracellulare, Mycobacterium leprae, Corynebacterium diphtheriae,* and *Corynebacterium ulcerans.*

98. The method of claim 92, wherein said bacterium is selected from the group consisting of *Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis, Staphylococcus saccharolyticus.*

99. A method of enhancing the antimicrobial effect of an antimicrobial agent against a microbe, comprising contacting said microbe with said antimicrobial agent and a non-tetracycline-specific efflux pump inhibitor in an amount effective to inhibit an efflux pump in said microbe, wherein said microbe is a bacteriuxn and said antimicrobial agent is a rifamycin antibacterial agent, and wherein said efflux pump inhibitor has a structure of any of structures 1, 2, 3, or 4, namely:

Structure 1
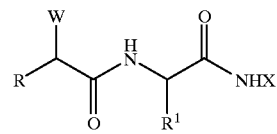

Structure 2
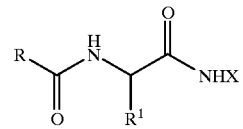

Structure 3
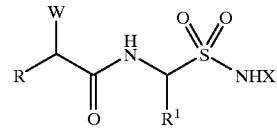

Structure 4
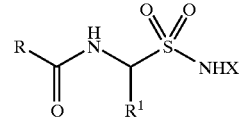

wherein

R is alkyl (C$_1$–C$_4$); fluoroalkyl (C$_1$–C$_4$); perfluoroalkyl (C$_1$–C$_4$); alkoxy (C$_1$–C$_4$); alkylthio (C$_1$–C$_4$); halogen (Br, Cl, F or I); aryl (C$_6$–C$_{10}$); monosubstituted aryl (C$_6$–C$_{10}$), substituted with alkyl (C$_1$–C$_4$), alkoxy (C$_1$–C$_4$), alkylthio (C$_1$–C$_4$), halogen (Br, Cl, F or I), amino, monosubstituted amino wherein the substituent is alkyl (C$_1$–C$_4$), disubstituted amino wherein the substituents are any combination of alkyl (C$_1$–C$_4$)], or hydroxyl; disubstituted aryl (C$_6$–C$_{10}$) substituted with any combination of alkyl (C$_1$–C$_4$), alkoy (C$_1$–C$_4$), alkylthio (C$_1$–C$_4$), halogen (Br, Cl, F or I) and amino, 2-(or 3-)-thienyl, 2-(or 3-)-furanyl, or 2-(3- or 4-)-pyridyl;

W is H; NH$_2$; monosubstituted amino wherein the substituent is alkyl (C$_1$–C$_4$); disubstituted amino substituted with any combination of alkyl (C$_1$–C$_4$); an aza-heterocycle; halogen (Br, Cl, F, I); hydroxyl; alkoxy (C$_1$–C$_4$); or alkylthio (C$_1$–C$_4$);

R$^1$ is (CH$_2$)$_n$NR$^a$R$_b$; (CH$_2$)$_n$NR$^b$R$^c$; (CH$_2$)$_n$NHC=(NR$^a$)NR$^b$R$^c$; (CH$_2$)$_n$SNHC=(NR$^a$)NR$^b$R$^c$; (CH$_2$)$_n$C=(NR$^a$)NR$^b$R$^c$; (CH$_2$)$_n$N=CNR$^b$R$^c$, wherein (n is 2–4) and R$^a$ (R$^b$ or R$^c$) are independently H, alkyl (C$_1$–C$_4$), aryl (C$_6$), substituted aryl, benzyl, substituted benzyl substituted with alkyl (C$_1$–C$_4$), alkoxy (C$_1$–C$_4$), alkylthio (C$_1$–C$_4$), halogen (Br, Cl, F or I), or amino, or R$^a$+R$^b$ is (CH$_2$)$_{2-3}$ or —CH=CH—;

X is aryl (C$_6$–C$_{10}$); —(CH$_2$)$_{0-2}$aryl (C$_6$–C$_{10}$); substituted aryl (C$_6$–C$_{10}$) substituted with alkyl (C$_1$–C$_4$), alkoxy (C$_1$–C$_4$), alkylthio (C$_1$–C$_4$), halogen (Br, Cl, F or I), or amino; substituted —(CH$_2$)$_{0-2}$aryl (C$_6$–C$_{10}$) with substitution on the aryl unit with alkyl (C$_1$–C$_4$), alkoxy (C$_1$–C$_4$), alkylthio (C$_1$–C$_4$), halogen (Br, Cl, F or I), or amino; 2-(or 3-)-thienyl; 2-(or 3-)-furyl; 2-(3- or 4-)-pyridyl; benzofuranyl with attachment at any position on the benzofuran ring; or benzothienyl with attachment at any position on the benzothiophene ring; and where there are centers of asymmetry, the absolute stereochemistry can be either R or S-configuration, or there can be a racemic mixture.

100. The method of claim 99, wherein said bacterium is selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Acinetobacter calcoaceticus,* and *Acinetobacter haemolyticus.*

101. The method of claim 99, wherein said bacterium is selected from the group consisting of *Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Morganella morganii, Escherichia coli, Citrobacter freundii, Proteus mirabilis Proteus vulgaris, Providencia alcalifaciens, Providencia rettgeri, Providencia stuartii, Aeromonas hydrophilia, Francisella tularensis, Yersinia enterocolitica, Yersinia pestis, Yersinia pseudotuberculosis,* and *Yersinia intermedia.*

102. The method of claim 99, wherein said bacterium is selected from the group consisting of *Neisseria gonorrhoeae, Neisseria meningitidis, Moraxella* (Branhamella) *catarrhalis, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida,* and *Pasteurella haemolytica.*

103. The method of claim 99, wherein said bacterium is selected from the group consisting of *Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes,* and *Gardnerella vaginalis.*

104. The method of claim 99, wherein said bacterium is selected from the group consisting of *Mycobacterium tuberculosis, Mycobacterium avium, Mycobacterium intracellulare, Mycobacterium leprae, Corynebacterium diphtheriae,* and *Corynebacterium ulcerans.*

105. The method of claim 99, wherein said bacterium is selected from the group consisting of *Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* and *Staphylococcus saccharolyticus.*

106. A method of enhancing the antimicrobial effect of an antimicrobial agent against a microbe, comprising contacting said microbe with said antimicrobial agent and a non-tetracycline-specific efflux pump inhibitor in an amount effective to inhibit an efflux pump in said microbe, wherein said microbe is a bacterium and said antimicrobial agent is a macrolide antibacterial agent, and wherein said efflux pump inhibitor has a structure of any of structures 1, 2, 3, or 4, namely:

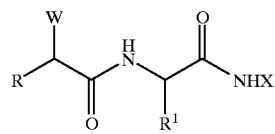

Structure 1

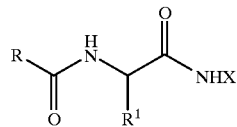

Structure 2

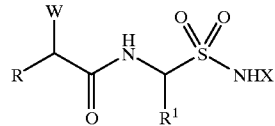

Structure 3

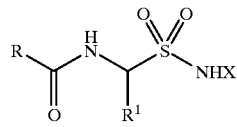

Structure 4 wherein

R is alkyl ($C_1$–$C_4$); fluoroalkyl ($C_1$–$C_4$); perfluoroalkyl ($C_1$–$C_4$); alkoxy ($C_1$–$C_4$); alkylthio ($C_1$–$C_4$); halogen (Br, Cl, F or I); aryl ($C_6$–$C_{10}$), monosubstituted aryl ($C_6$–$C_{10}$), substituted with alkyl ($C_1$–$C_4$), alkoxy ($C_1$–$C_4$), alkylthio ($C_1$–$C_4$), halogen (Br, Cl, F or I), amino, monosubstituted amino wherein the substituent is alkyl ($C_1$–$C_4$), disubstituted amino wherein the substituents are any combination of alkyl ($C_1$–$C_4$)], or hydroxyl; disubstituted aryl ($C_6$–$C_{10}$) substituted with any combination of alkyl ($C_1$–$C_4$), alkoxy ($C_1$–$C_4$), alkylthio ($C_1$–$C_4$), halogen (Br, Cl, F or I) and amino, 2-(or 3-)-thienyl, 2-(or 3-)-furanyl, or 2-(3- or 4-)-pyridyl;

W is H; $NH_2$; monosubstituted amino wherein the substituent is alkyl ($C_1$–$C_4$); disubstituted amino substituted with any combination of alkyl ($C_1$–$C_4$); an aza-heterocycle; halogen (Br, Cl, F, I); hydroxyl; alkoxy ($C_1$–$C_4$); or alkylthio ($C_1$–$C_4$);

$R^1$ is $(CH_2)_nNR^aR_b$; $(CH_2)_nNR^bR^c$; $(CH_2)_nNHC=(NR^a)NR^bR^c$; $(CH_2)_nSNHC=(NR^a)NR^bR^c$; $(CH_2)_nC=(NR^a)NR^bR^c$; $(CH_2)_nN=CNR^bR^c$, wherein (n is 2–4) and $R^a$ ($R^b$ or $R^c$) are independently H, alkyl ($C_1$–$C_4$), aryl ($C_6$), substituted aryl, benzyl, substituted benzyl substituted with alkyl ($C_1$–$C_4$), alkoxy ($C_1$–$C_4$), alkylthio ($C_1$–$C_4$), halogen (Br, Cl, F or I), or amino, or $R^a+R^b$ is $(CH_2)_{2-3}$ or —CH=CH—;

X is aryl ($C_6$–$C_{10}$); —$(CH_2)_{0-2}$aryl ($C_6$–$C_{10}$); substituted aryl ($C_6$–$C_{10}$) substituted with alkyl ($C_1$–$C_4$), alkoxy ($C_1$–$C_4$), alkylthio ($C_1$–$C_4$), halogen (Br, Cl, F or I), or amino; substituted —$(CH_2)_{0-2}$aryl ($C_6$–$C_{10}$) with substitution on the aryl unit with alkyl ($C_1$–$C_4$), alkoxy ($C_1$–$C_4$), alkylthio ($C_1$–$C_4$), halogen (Br, Cl, F or I), or amino; 2-(or 3-)-thienyl; 2-(or 3-)-furyl; 2-(3- or 4-)-pyridyl; benzofuranyl with attachment at any position on the benzofuran ring; or benzothienyl with attachment at any position on the benzothiophene ring; and where there are centers of asymmetry, the absolute stereochemistry can be either R or S-configuration, or there can be a racemic mixture.

107. The method of claim 106, wherein said bacterium is selected from the group consisting of *Streptococcus pneumoniae, Streptococcus aagalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* and *Staphylococcus saccharolyticus.*

108. The method of claim 106, wherein said bacterium is selected from the group consisting of *Neisseria gonorrhoeae, Neisseria meningitidis, Moraxella* (Branhamella) *catarrhalis, Nocardia asteroides, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida,* and *Pasteurella haemolytica.*

109. The method of claim 106, wherein said bacterium is selected from the group consisting of *Heliobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes,* and *Gardnerella vaginalis.*

110. The method of claim 106, wherein said bacterium is selceted from the group consisting of *Mycobacterium tuberculosis, Mycobacterium avium, Mycobacterium intracellulare,* and *Mycobacterium leprae.*

* * * * *